US008735657B2

(12) United States Patent
Fernandes

(10) Patent No.: US 8,735,657 B2
(45) Date of Patent: *May 27, 2014

(54) METHODS FOR ENHANCING STRESS TOLERANCE IN PLANTS AND COMPOSITIONS THEREOF

(75) Inventor: Mary Fernandes, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/821,846

(22) Filed: Jun. 23, 2010

(65) Prior Publication Data

US 2011/0035835 A1  Feb. 10, 2011

Related U.S. Application Data

(63) Continuation of application No. 10/953,856, filed on Sep. 29, 2004, now Pat. No. 7,786,353.

(60) Provisional application No. 60/506,717, filed on Sep. 29, 2003, provisional application No. 60/530,453, filed on Dec. 17, 2003.

(51) Int. Cl.
  *A01H 5/00*    (2006.01)
  *A01H 1/00*    (2006.01)
  *C12N 15/09*   (2006.01)
  *C12N 15/82*   (2006.01)

(52) U.S. Cl.
  USPC ........... 800/289; 800/298; 800/288; 800/278; 800/320.1; 800/320.2; 800/312; 800/306; 435/468

(58) Field of Classification Search
  None
  See application file for complete search history.

(56) References Cited

FOREIGN PATENT DOCUMENTS

| WO | WO 9705165 | * | 2/1997 |
| WO | 2010019838 |   | 2/2010 |

OTHER PUBLICATIONS

Guo et al. PNAS (2004) 101: 9205-9210.*
Keskin et al. Protein Science (2004) 13:1043-1055.*
WO 9705165.*
Lee et al., "Family of the Major Cold-Shock Proteinm CspA (CS7.4), of *Escherichia coli*, whose Members Show a High Sequence Similarity with the Eukaryotic Y-Box Binding Proteins", Molecular Microbiology, 1994, pp. 833-839, vol. 11, No. 5.
Kandror et al., "Trehalose Synthesis is Induced Upon Exposure of *Escherichia coli* to Cold and is Essential for Viability at Low Temperatures", Proceedings of the National Academy of Sciences of the USA, Jul. 23, 2002, pp. 9727-9732, vol. 99, No. 15.
Phadtare, "Recent Developments in Bacterial Cold-Shock Response", Curr. Issues Mol. Biol., 2004, pp. 125-136, vol. 6.
Graumann et al., "A superfamily of proteins that contain the cold-shock domain", Reviews, Aug. 1998, pp. 286-290, TIBS 23.
Sigrist et al., "PROSITE: A documented database using patterns and profiles as motif descriptors", Briefings in Bioinformatics, Sep. 2002, pp. 265-274, vol. 3 No. 3.
Yamanaka et al., "The CspA family in *Escherichia coli*: multiple gene duplication for stress adaptation", Molecular Microbiology, 1998, pp. 247-255, vol. 27 No. 2.
Xia et al., "Acquirement of cold sensitivity by quadruple deletion of the cspA family and its suppression by PNPase 51 domain in *Escherichia coli*", Molecular Microbiology, 2001, pp. 179-188, vol. 40 No. 1.
Office Action for Indian Patent Application No. 2407/DELNP/2006 dated Sep. 11, 2008.
Refusal from Indian Patent Office regarding Patent Application No. 2407/DELNP/2006 dated Jun. 22, 2011.
Indian Intellectual Property Appellate Board decision regarding Patent Application No. 2407/DELNP/2006 dated Jul. 5, 2013.
Monsanto Data Summary dated Nov. 4, 2013.

* cited by examiner

*Primary Examiner* — Medina A Ibrahim
(74) *Attorney, Agent, or Firm* — Thompson Coburn LLP; Charles P. Romano

(57) ABSTRACT

Increased tolerance to abiotic stress in a plant is provided by introducing DNA expressing a cold shock protein, e.g. bacterial cold shock protein.

28 Claims, 19 Drawing Sheets

METHODS FOR ENHANCING STRESS TOLERANCE IN PLANTS AND COMPOSITIONS THEREOF

CROSS REFERENCE TO RELATED APPLICATIONS

This application is a continuation of U.S. non-provisional patent application Ser. No. 10/953,856, filed Sep. 29, 2004 now U.S. Pat. No. 7,786,353 and incorporated herein by reference in its entirety and which claims benefit under 35 USC §119(e) of U.S. provisional application Ser. No. 60/506,717 filed Sep. 29, 2003 and Ser. No. 60/530,453, filed Dec. 17, 2003.

INCORPORATION OF SEQUENCE LISTING

A copy of the sequence listing in a computer-readable form and named (47-21)51768D CSP.ST25.txt, which is approximately 100,393 bytes (measured in MS-Windows) and was created on Nov. 13, 2012, was filed via the USPTO EFS system on Jan. 4, 2013 and is hereby incorporated by reference.

FIELD OF THE INVENTION

This invention relates to cold, drought, salt, cold germination, heat, and other abiotic stress tolerance in plants and viral, fungal, bacterial and other abiotic stress tolerance in plants. Specifically this invention relates to a method of increasing the biotic and abiotic stress tolerance of plants by expressing a cold shock protein(s) within the cells of said plant.

BACKGROUND

Seed and fruit production are multi-billion dollar commercial industries and primary sources of income for numerous states in the United States and for many countries around the world. Commercially valuable seeds include, for example, canola, cottonseeds and sunflower seeds, which are prized for the vegetable oil that can be pressed from the seed. The seeds of leguminous plants such as peas, beans, and lentils also are commercially valuable as they are rich in proteins, with soybeans, for example, consisting of 40-45% protein and 18% fats and oils. In addition, coffee is a valuable crop made from the dried and roasted seeds of *Coffea arabica* plants, while chocolate is made from the cacao seed or "bean." Similarly, many fruits and seeds are commercially valuable, including, for example, corn, rice, wheat, barley and other cereals, nuts, legumes, tomatoes, and citrus fruits. For example, corn seeds are made into many food items or items used in cooking, such as taco shells, corn oil, tortillas, corn flakes, corn meal, and many others. Corn is also used as raw material in many production processes, including but not limited to, feed and ethanol production.

Seed and fruit production are both limited inherently due to biotic and abiotic stress. Soybean (*Glycine max*), for instance, is a crop species that suffers from loss of seed germination during storage and fails to germinate when soil temperatures are cool (Zhang et al., *Plant Soil* 188: (1997)). This is also true in corn and other plants of agronomic importance. Improvement of abiotic stress tolerance in plants would be an agronomic advantage to growers allowing increasing growth and/or germination in cold, drought, flood, heat, UV stress, ozone increases, acid rain, pollution, salt stress, heavy metals, mineralized soils, and other abiotic stresses. Biotic stress, such as fungal and viral infection, also cause large crop losses world wide.

Traditional breeding (crossing specific alleles of one genotype into another) has been used for centuries to increase biotic stress tolerance, abiotic stress tolerance, and yield. Traditional breeding is limited inherently to the limited number of alleles present in the parental plants. This in turn limits the amount of genetic variability that can be added in this manner. Molecular biology has allowed the inventors of the instant invention to look far and wide for genes that will improve stress tolerance in plants. Our inventors sought to determine how other organisms react to and tolerate stressful conditions. The cold shock proteins are part of a system used by bacteria and other organisms to survive cold and stressful conditions. It was posited by the inventors that placing genes encoding the cold shock proteins, and proteins related to them, into plants and expressing them would increase the cold, drought, heat, water, and other abiotic stress tolerance of plants as well as fungal, viral, and other biotic stress tolerance of plants. They also believe that using genes that are homologous to cold shock proteins, or have sequence similarity, would also increase biotic and abiotic stress tolerance.

This invention is useful to farmers to limit their losses due to biotic and abiotic stress.

SUMMARY OF THE INVENTION

The present invention provides a plant expressing a cold shock protein (Csp) in the cells of the plant. The expression of this csp leads to greater abiotic stress tolerance within said plant. In one embodiment, a polynucleotide encoding a csp is expressed by an operably linked promoter that functions in plants, and a terminator that functions in plants.

More specifically the invention provides a recombinant DNA molecule that comprises, in to the 5' to 3' direction, a first DNA polynucleotide that comprises a promoter that functions in plants, operably linked to a second DNA polynucleotide that encodes a cold shock protein, operably linked to a 3' transcription termination DNA polynucleotide providing a polyadenylation site. The first DNA polynucleotide is often advantageously heterologous to the second DNA polynucleotide. The invention also provides a recombinant DNA molecule having an intron inserted between the first DNA polynucleotide and the second DNA polynucleotide. The invention also provides a recombinant DNA molecule where the second DNA polynucleotide encodes a protein comprising the motif in SEQ ID NO: 3. In specific embodiments of the recombinant DNA of this invention the second DNA polynucleotide encodes a protein selected from the group consisting of (a) a protein with an amino acid sequence of substantial identity to an amino acid sequence of a cold shock protein from gram positive bacteria,
(b) a cold shock protein from *Bacillus subtilis*,
(c) a homologue of *Bacillus subtilis* cold shock protein B (CspB),
(d) a protein with an amino acid sequence of substantial identity to SEQ ID NO: 2,
(e) a protein with an amino acid sequence of substantial identity to an amino acid sequence of a cold shock protein from a gram negative bacteria,
(f) a protein comprising a cold shock protein from *Escherichia coli*,
(g) a homologue of *Escherichia coli* cold shock protein A (CspA), (h) a protein with an amino acid sequence that has substantial identity to SEQ ID NO:1,
(i) a cold shock protein from *Agrobacterium tumefaciens*, and
(j) a protein having an amino acid sequence of substantial identity to any of SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, or 65.

The invention also provides a recombinant DNA molecule wherein the promoter is selected from the group consisting of inducible promoters, constitutive promoters, temporal-regulated promoters, developmentally-regulated promoters, tissue-preferred promoters, cold enhanced promoters, cold-specific promoters, stress enhanced promoters, stress specific promoters, drought inducible promoters, water deficit inducible promoters, and tissue-specific promoters.

The invention also provides plant cells and plants containing in their genome recombinant DNA molecules as described and the propagules and progeny produced therefrom. Plants include, but are not limited to crop plants, monocots, and dicots. More specifically these could include soybean, corn, canola, rice, cotton, barley, oats, turf grasses, cotton, and wheat.

The invention also provides abiotic stress-tolerant, transgenic plants that have been transformed with a recombinant DNA molecule that expresses a cold shock protein. Such plants and their cells and propagules such as seeds contain in their genome recombinant DNA molecules that expresses a cold shock protein. Such plants exhibit one or more of the following enhanced properties: a higher growth rate under conditions where cold temperature would be limiting for growth for a non-transformed plant of the same species, (a) a higher growth rate under conditions where high temperature would be limiting for growth for a non-transformed plant of the same species,
(b) a higher growth rate under conditions where water would be limiting for growth for a non-transformed plant of the same species,
(c) a higher growth rate under conditions where increased salts or ions in the soil and/or water would be limiting for growth of a non-transformed plant of the same species,
(d) has a greater percentage of plants surviving after a cold shock than a non-transformed plant of the same species,
(e) an increased yield when compared to a non-transformed plant of the same species, or
(f) resistance to drought compared to a non-transformed plant of the same species.

A method of the invention comprises propagating plants of this invention, e.g. for the purpose of generating seeds, by simply planting such seeds in soil and allowing them to grow, e.g. under stress conditions. More specifically, this invention provides a method of producing a plant that has enhanced trait such as abiotic stress tolerance, increased yield or increased root mass. The method comprises the steps of a) inserting into the genome of a plant cell or cells a recombinant DNA molecule comprising DNA encoding a cold shock protein,
b) obtaining a transformed plant cell or cells,
c) regenerating plants from said transformed plant cell(s); and
d) selecting plants which exhibit the enhance trait.

In one aspect of the invention plants are selected which exhibit enhanced abiotic stress tolerance selected from the group consisting of heat tolerance, salt tolerance, drought tolerance, and survival after cold shock.

The invention also provided isolated proteins which are at least 40% identity to a protein having an amino acid sequence selected from the group consisting of SEQ ID NOS: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, and 65. In certain aspects comparable traits can be achieved by substituting a cold shock protein with a protein having higher homology than 40% identity, e.g. with a protein that is at least 50%, 60%, 70%, 80%, 90% or at least 95% identical to a cold shock protein specifically disclosed herein. Likewise, this invention also provides an isolated nucleic acid encoding a cold shock protein motif which hybridizes to a nucleic acids with a DNA sequence selected from the group comprising SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 90 and 92.

The invention also specifically provides isolated nucleic acids encoding a cold shock protein which has a DNA sequence that is substantially identical to a sequence in the group consisting of SEQ ID NOs: 5, 7, 9, 29, 31, 33, 35, 37, 39, 41, 43, 53, 55, 57, 59, 61, 63, and 65.

The invention also provides propagules containing the above recombinant DNA molecules, when they are planted or otherwise caused to germinate, and a field of plants germinated from said propagules, e.g. where such propagule are seeds.

A method of producing a transgenic plant is also provided, the method comprising the steps of: (i) introducing into the genome of a plant cell a DNA molecule comprising a DNA polynucleotide at least 40% homologous to a protein having an amino acid sequence selected from the group consisting of SEQ ID NOs: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, and 65, or fragment, or cis element thereof, wherein said DNA polynucleotide is operably linked to a promoter and operably linked to a 3' transcription termination DNA polynucleotide; and (ii) selecting said transgenic plant cell; and (iii) regenerating said transgenic plant cell into a transgenic plant; also provided are the plants made by this method.

DETAILED DESCRIPTION OF SPECIFIC EMBODIMENTS

Figure 1:
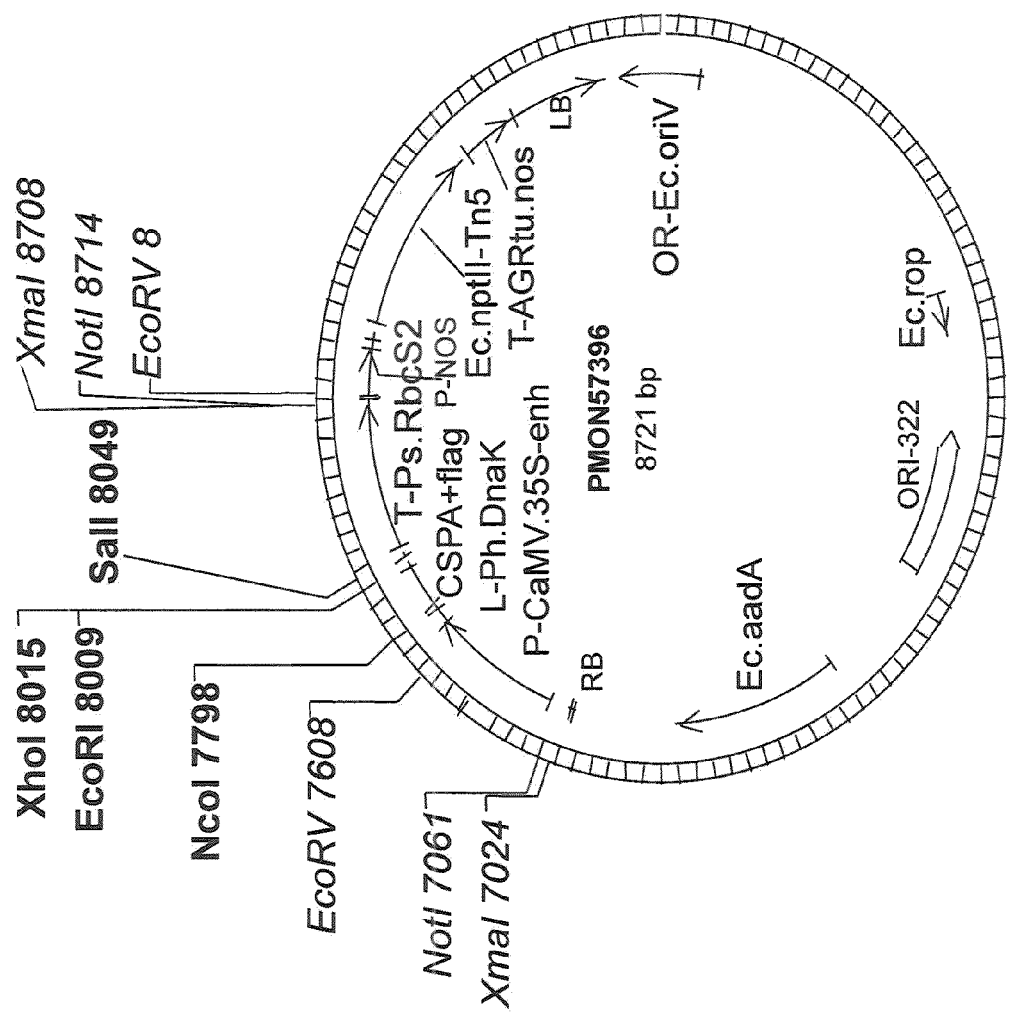
FIG. 1 shows a plasmid map of pMON57396.

The instant invention provides a plant with increased tolerance to biotic and abiotic stress. The plant provided has increased stress tolerance due to the expression of cold shock protein (csp) in the cells of said plant. The invention provides examples of several embodiments and contemplates other embodiments that are expected to function in the invention.

The following definitions and methods are provided to better define the current invention and to guide those of ordinary skill in the art in the practice of the present invention. Unless otherwise noted, terms are to be understood according to conventional usage by those of ordinary skill in the art. For example, definitions of common terms used in molecular biology and molecular genetics can be found in Lewin, *Genes VII*, Oxford University Press and Cell Press, New York, 2000; Buchanan, et al., *Biochemistry and Molecular Biology of Plants*, Courier Companies, USA, 2000; Lodish, et al., *Molecular Cell Biology*, W.H. Freeman and Co., New York, 2000. Common terms in genetics can be found in the prior references as well as Lynch, et al., *Genetics and Analysis of Quantitative Traits*, Sinauer and Associates, Sunderland, Mass., 1998; Hartwell, et al., *Genetics: From Genes to Genomes*, McGraw-Hill Companies, Boston, Mass., 2000; Hartl, et al., *Genetics: Analysis of Genes and Genomes*, Jones and Bartlett Publishers, Sudbury, Mass.; Strachan, et al., *Human Molecular Genetics*, John Wiley and Sons, New York, 1999.

The nomenclature for DNA bases as set forth in 37 CFR §1.822 is used. The standard one- and three-letter nomenclature for amino acid residues is used.

Many agronomic traits can affect "yield". For example, these could include, without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. For example, these could also include, without limitation, efficiency of germination (including germination in stressed conditions), growth rate of any or all plant parts (including growth rate in stressed conditions), ear number, seed number per ear, seed size, composition of seed (starch, oil, protein), characteristics of seed fill. Yield can be measured in many ways, these might include test weight, seed weight, seed number per plant, seed weight per plant, seed number or weight per unit area (i.e. seeds, or weight of seeds, per acre), bushels per acre, tonnes per acre, tons per acre, kilo per hectare. In an embodiment, a plant of the present invention exhibits an enhanced trait that is a component of yield.

"Nucleic acid (sequence)" or "polynucleotide (sequence)" refers to single- or double-stranded DNA (deoxyribonucleic acid) or RNA (ribonucleic acid) of genomic or synthetic origin, i.e., a polymer of deoxyribonucleotide or ribonucleotide bases, respectively, read from the 5' (upstream) end to the 3' (downstream) end. The nucleic acid can represent the sense or complementary (antisense) strand.

"Native" refers to a naturally occurring ("wild-type") nucleic acid sequence.

"Heterologous" sequence refers to a sequence which originates from a foreign source or species or, if from the same source, is modified from its original form. For example, a native promoter could be used to cause the transcription of a heterologous gene from the same or from a different species.

"Parts" of a plant include all parts or pieces of a plant including, but not limited to, roots, shoots, leaves, stems, pollen, seeds, flowers, stamen, pistils, eggs, embryos, petal, filaments, carpels (including stigma, ovary, and style), cell(s) or any piece of the above.

"Propagule" includes all products of meiosis and mitosis, including but not limited to, seed and parts of the plant able to propogate a new plant. For example, propagule includes a shoot, root, or other plant part that is capable of growing into an entire plant. Propagule also includes grafts where one portion of a plant is grafted to another portion of a different plant (even one of a different species) to create a living organism. Propagule also includes all plants and seeds produced by cloning or by bringing together meiotic products, or allowing meiotic products to come together to form an embryo or fertilized egg (naturally or with human intervention).

An "isolated" nucleic acid sequence is substantially separated or purified away from other nucleic acid sequences with which the nucleic acid is normally associated in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids.

"Identity" or "identical" as used herein, when referring to comparisons between protein(s) or nucleic acid(s) means 98% or greater identity.

A first nucleic acid or protein sequence displays "substantial identity" or "substantial similarity" to a reference nucleic acid sequence or protein if, when optimally aligned (with appropriate nucleotide or amino acid insertions or deletions totaling less than 20 percent of the reference sequence over the window of comparison) with the other nucleic acid (or its complementary strand) or protein, there is at least about 60% nucleotide sequence equivalence, even better would be 70%, preferably at least about 80% equivalence, more preferably at least about 85% equivalence, and most preferably at least about 90% equivalence over a comparison window of at least 20 nucleotide or amino acid positions, preferably at least 50 nucleotide or amino acid positions, more preferably at least 100 nucleotide or amino acid positions, and most preferably over the entire length of the first nucleic acid or protein. Optimal alignment of sequences for aligning a comparison window may be conducted by the local homology algorithm(s), preferably by computerized implementations of these algorithms (which can be found in, for example, Wisconsin Genetics Software Package Release 7.0, Genetics Computer Group, 575 Science Dr., Madison, Wis.). The reference nucleic acid may be a full-length molecule or a portion of a longer molecule. Alternatively, two nucleic acids have substantial identity if one hybridizes to the other under stringent conditions. Appropriate hybridization conditions can be determined empirically, or can be estimated based, for example, on the relative G+C content of the probe and the number of mismatches between the probe and target sequence, if known. Hybridization conditions can be adjusted as desired by varying, for example, the temperature of hybridizing or the salt concentration (Sambrook et al., *Molecular Cloning: A Laboratory Manual, 2$^{nd}$ Edition*, Cold Spring Harbor Press, 1989).

A first nucleic acid sequence is "operably linked" with a second nucleic acid sequence when the sequences are so arranged that the first nucleic acid sequence affects the function of the second nucleic acid sequence. Preferably, the two sequences are part of a single contiguous nucleic acid molecule and more preferably are adjacent. For example, a promoter is operably linked to a gene if the promoter regulates or mediates transcription of the gene in a cell. For example, a transcriptional termination region (terminator) is operably linked to a gene when said terminator leads to a RNA polymerase ending a transcript containing said gene at or near the terminator. For example, an enhancer is often not adjacent to the promoter that it is exhibiting its effect on, but is generally in the same nucleic acid molecule.

A "recombinant" nucleic acid or DNA, or RNA molecule is made by an artificial combination of two otherwise separated segments of sequence, e.g., by chemical synthesis or by the manipulation of isolated segments of nucleic acids by genetic engineering techniques. Techniques for nucleic-acid manipulation are well-known (see, e.g., Sambrook et al., *Molecular Cloning: A Laboratory Manual, 2nd Edition*, Cold Spring Harbor Press, 1989). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers.

"Expression" of a gene refers to the transcription of a gene to produce the corresponding mRNA and translation of this mRNA to produce the corresponding gene product, i.e., a peptide, polypeptide, or protein. Gene expression is controlled or modulated by regulatory elements including 5' regulatory elements such as promoters.

The terms "recombinant DNA construct", "recombinant vector", "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner.

"Complementary" refers to the natural association of nucleic acid sequences by base-pairing. Complementarity between two single-stranded molecules may be partial, if only some of the nucleic acids pair are complementary; or complete, if all bases pair are complementary. The degree of complementarity affects the efficiency and strength of hybridization and amplification reactions.

"Homology" refers to the level of similarity between nucleic acid or amino acid sequences in terms of nucleotide or amino acid identity or similarity, respectively, i.e., sequence similarity or identity. Homology, homologue, and homologous also refers to the concept of similar functional properties among different nucleic acids or proteins. Homologues include genes that are orthologous and paralogous. Homologues can be determined by using the coding sequence for a gene, disclosed herein or found in appropriate database (such as that at NCBI or others) in one or more of the following ways. For a protein sequence, the sequences should be compared using algorithms (for instance see section on "identity" and "substantial identity"). For nucleotide sequences the sequence of one DNA molecule can be compared to the sequence of a known or putative homologue in much the same way. Homologues are at least 20% identical, more preferably 30%, more preferably 40%, more preferably 50% identical, more preferably 60%, more preferably 70%, more preferably 80%, more preferably 88%, more preferably 92%, most preferably 95%, across any substantial (25 nucleotide or amino acid, more preferably 50 nucleotide or amino acid, more preferably 100 nucleotide or amino acid, or most preferably the entire length of the shorter sequence) region of the molecule (DNA, RNA, or protein molecule).

Alternatively, two sequences, or DNA or RNA molecules that encode, or can encode, amino acid sequences, are homologous, or homologues, or encode homologous sequences, if the two sequences, or the complement of one or both sequences, hybridize to each other under stringent conditions and exhibit similar function. Thus if one were to determine whether two protein sequences were homologues, one would both do the computer exercises described herein, and create degenerate coding sequences of all possible nucleic acid sequences that could encode the proteins and determine whether they could hybridize under stringent conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to the high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In one preferred embodiment, a nucleic acid encoding a protein described in the present invention will specifically hybridize to one or more of the nucleic acid molecules or complements thereof or fragments of either under highly stringent conditions, for example at about 2.0×SSC and about 65° C. The hybridization of the probe to the target DNA molecule can be detected by any number of methods known to those skilled in the art, these can include, but are not limited to, fluorescent tags, radioactive tags, antibody based tags, and chemiluminescent tags.

"Cold shock protein(s)" (Csp(s) or CSP(s)) are proteins that have greater than 40% identity to *Escherichia coli* CspA protein (SEQ ID NO: 1) or *Bacillus subtilis* CspB protein (SEQ ID NO: 2), or, alternatively, cold shock proteins can be found by using the conserved domain as determined in the literature. For example, as used herein a cold shock protein is 40% identical, more preferably 50% identical, more preferably 60% identical, more preferably 70% identical, more preferably 80% identical, more preferably 90% identical, more preferably 95% identical to *E. coli* CspA or *B. subtilis* CspB across the entire length of *E. coli* CspA or *B. subtilis* CspB. Several databases are available that allow one skilled in the art to determine whether a new or existing protein contains a cold shock domain or is a cold shock protein, from Genbank to protein databases designed to allow the determination of protein relationships, and/or find related proteins. Included herein within the definition are all known cold shock proteins, including but not limited to CspA, CspB, CspC, CspD, CspE, CspF, CspG, CspH, and CspI (U.S. Pat. No. 6,610,533) from *Escherichia coli*.

The conserved cold shock domain is shown in SEQ ID NO: 3 ([FY]-G-F-I-x(6,7)-[DER]-[LIVM]-F-x-H-x-[STKR]-x-[LIVMFY]) (Prosite motif PS00352; Bucher and Bairoch, (In) ISMB-94; Proceedings 2nd International Conference on Intelligent Systems for Molecular Biology, Altman R., Brutlag D., Karp P., Lathrop R., Searls D., Eds., pp 53-61, AAAIPress, Menlo Park, 1994; Hofmann et al., Nucleic Acids Res. 27:215, 1999). Alternatively, cold shock proteins can be found using the Sprint database (a relational protein fingerprint database) (Attwood et al., Nucleic Acids Res. 28(1):225, 2000; Attwood, et al., Nucleic Acids Research, 30(1), in press, 2002). Alternatively, cold shock proteins can be found using a matrix based description, or Pfam. Pfam is a large collection of multiple sequence alignments and hidden Markov models covering many common protein domains (Bateman et al., Nucleic Acids Research 28:263, 2000). At this writing (November 2001; Pfam release 6) there are 3071 families. Cold shock proteins are included as PF00313. The species tree showing the distribution of cold shock proteins as determined in the Pfam database.

"Cold shock proteins" as used herein also include, but are not limited to, any protein that is found in a search, using a Cold shock protein as a query sequence, of a database using the "Blink" (Blast Link) function that can be found at the National Center for Biotechonology Information. "Blink" is a quick search function used to find proteins with similar sequences. This definition of "cold shock protein" or "cold shock domain" is in addition to those used above, and does not replace said definition. Cold shock proteins or proteins containing cold shock domains include, but are not limited to, all currently known proteins in public and private databases as well as those that have yet to be discovered that are similar enough to the claimed proteins (for example, *E. coli* CspA and *B. subtilis* CspB) to be "hits" under the standard blast search settings currently used in Blast Link (as of Nov. 1, 2001). As of this writing Blast 2 is being run, and Blast Link ("Blink") is running the default parameters for protein-protein blast searches. As of this writing we believe the default settings used in Blink are as follows; a BLOSUM62 matrix is being run, using the "nr" database, CD search is selected, as are composition based statistics, with the complexity selected as "low complexity", expect is 10, with a word size of 3, the gap costs are; existence 11, and extension 1. The list in Table I shows the first 200 hits for *E. coli* CspA using these standard settings, but we do not limit our claim to the first 200 hits. One skilled in the art would note that under these fairly stringent criteria 167 proteins of bacterial origin are found, but also 28 Metazoan and 5 plant proteins. These proteins include a broad range of proteins that, do to their homology to CspA, would be expected by the inventors to function in the present invention. This is by no means an all inclusive list, and other proteins would be expected to function in the present invention.

Table 20. Some cold shock proteins and proteins containing a cold shock domain found by similarity to *E. Coli* CspA. This list was compiled using the standard Blast Link settings at the National Center for Biotechnology information. The Genbank ID and name of each protein is shown. Note: Due to the way proteins are named, some proteins and sequences will have several entries, as proteins, cDNAs, alleles, etc. Genbank ID can be considered to be specific identifiers of each entry. Entries are in the approximate order of highest to lowest identity, in comparison with the query sequence.

| Genbank ID # | Gene Name |
|---|---|
| 576191 | Major Cold Shock Protein 7.4 (Cspa (Cs 7.4)) Of (*Escherichia Coli*) |
| 349561 | DNA-binding protein [*Salmonella typhimurium*] |
| 3891780 | Chain A, Major Cold-Shock Protein From *Escherichia Coli* Solution Nm |
| 479003 | cold-shock protein [*Escherichia coli*] |
| 1778828 | major cold shock protein CSPA2 [*Yersinia enterocolitica*] |
| 6073870 | major cold shock protein CSPA1 [*Yersinia enterocolitica*] |
| 1468921 | cold shock potein CspG [*Escherichia coli*] |
| 2275140 | hypothetical protein [*Yersinia pestis*] |
| 12514257 | homolog of *Salmonella* cold shock protein [*Escherichia coli* O157:H7 |
| 15981565 | major cold shock protein Cspa1 [*Yersinia pestis*] |
| 3249024 | cold shock protein CspB [*Yersinia enterocolitica*] |
| 15979692 | cold shock protein [*Yersinia pestis*] |
| 1742550 | Cold shock-like protein CspB. [*Escherichia coli*] |
| 16419141 | RNA chaperone, negative regulator of cspA transcription [*Salmonella* |
| 10039151 | cold shock-like protein cspE [*Buchnera* sp. APS] |
| 9957540 | cold shock protein B [*Yersinia enterocolitica*] |
| 1778540 | cold shock-like protein [*Escherichia coli*] |
| 471099 | CspE (MsmC) [*Escherichia coli*] |
| 2961317 | cspB [*Salmonella typhimurium*] |
| 16503235 | cold shock protein [*Salmonella enterica* subsp. *enterica* serovar |
| 9658370 | cold shock domain family protein [*Vibrio cholerae*] |
| 460698 | CspC (MsmB) [*Escherichia coli*] |
| 15980582 | putative cold shock protein [*Yersinia pestis*] |
| 10038996 | cold shock-like protein cspC [*Buchnera* sp. APS] |
| 15979774 | cold shock protein [*Yersinia pestis*] |
| 9657556 | cold shock transcriptional regulator CspA [*Vibrio cholerae*] |
| 4454361 | cold shock protein, CSPA [*Vibrio cholerae*] |
| 2970685 | cold shock protein C [*Salmonella typhimurium*] |
| 1402743 | major cold-shock protein [*Citrobacter freundii*] |
| 5869509 | CspG [*Shewanella violacea*] |
| 5869504 | CspA [*Shewanella violacea*] |
| 9968446 | cold shock protein [*Lactobacillus plantarum*] |
| 1405474 | CspC protein [*Bacillus cereus*] |
| 3850776 | cold shock protein D [*Lactococcus lactis*] |
| 10176234 | cold-shock protein [*Bacillus halodurans*] |
| 1869948 | cold shock protein [*Lactobacillus plantarum*] |
| 729220 | COLD SHOCK PROTEIN CSPC |
| 7379745 | putative transcriptional regulator [*Neisseria meningitidis* Z2491] |
| 1620431 | csp [*Lactobacillus plantarum*] |
| 1405472 | CspB protein [*Bacillus cereus*] |
| 3892590 | cold shock protein E [*Lactococcus lactis*] |
| 7226073 | cold-shock domain family protein [*Neisseria meningitidis* MC58] |
| 2493766 | COLD SHOCK-LIKE PROTEIN CSPLA (CSPL) |
| 1001878 | CspA protein [*Listeria monocytogenes*] |
| 13623066 | putative cold shock protein [*Streptococcus pyogenes* M1 GAS] |
| 758663 | cold shock protein [*Arthrobacter globiformis*] |
| 4468119 | cold shock protein A; CspA protein [*Bordetella pertussis*] |

-continued

| Genbank ID # | Gene Name |
|---|---|
| 2370256 | cold shock protein [*Lactococcus lactis*] |
| 1405470 | CspA protein [*Bacillus cereus*] |
| 2226349 | CspC [*Staphylococcus aureus*] |
| 1405476 | CspD protein [Bacillus cereus] |
| 1513079 | cold acclimation protein A [*Pseudomonas fragi*] |
| 7242722 | cold shock protein [*Streptomyces coelicolor* A3(2)] |
| 2425105 | major cold-shock protein [*Micrococcus luteus*] |
| 2105046 | cspA [*Mycobacterium tuberculosis* H37Rv] |
| 15023696 | Cold shock protein [*Clostridium acetobutylicum*] |
| 12720931 | MsmB [*Pasteurella multocida*] |
| 8101860 | major cold shock protein CspA [*Staphylococcus aureus*] |
| 1513081 | cold acclimation protein B [*Pseudomonas fragi*] |
| 3097243 | small cold-shock protein [*Mycobacterium leprae*] |
| 9587215 | cold-shock protein CspA [*Mycobacterium smegmatis*] |
| 9107526 | cold shock protein [*Xylella fastidiosa* 9a5c] |
| 1256629 | cold-shock protein [*Bacillus subtilis*] |
| 12054789 | cold shock protein (CspLB) [*Listeria monocytogenes*] |
| 1864167 | major cold-shock protein homolog CspB [*Listeria monocytogenes*] |
| 1421212 | Major Cold Shock Protein (Cspb) |
| 297761 | cold shock protein (CspB) [*Bacillus subtilis*] |
| 13625473 | cold acclimation protein CapB [*Pseudomonas* sp. 30/3] |
| 9657576 | cold shock DNA-binding domain protein [*Vibrio cholerae*] |
| 11933043 | cold-shock like protein [*Streptomyces nodosus*] |
| 11933034 | cold-shock like protein [*Streptomyces hygroscopicus*] |
| 8248794 | cold shock protein [*Streptomyces coelicolor* A3(2)] |
| 1778825 | major cold shock protein CspA [*Pseudomonas aeruginosa*] |
| 740006 | cold shock protein |
| 2226347 | CspB [*Staphylococcus aureus*] |
| 1616777 | cold shock-like protein [*Stigmatella aurantiaca*] |
| 7210998 | cold-shock protein [*Streptomyces coelicolor* A3(2)] |
| 729217 | COLD SHOCK PROTEIN CSPB |
| 1067201 | cold shock protein [*Streptomyces coelicolor*] |
| 7321274 | cold shock protein [*Streptomyces coelicolor* A3(2)] |
| 1402789 | major cold-shock protein [*Yersinia enterocolitica*] |
| 1513086 | temperature acclimation protein B [*Pseudomonas fragi*] |
| 16411332 | similar to cold shock protein [*Listeria monocytogenes*] |
| 5732895 | F40 [*Streptomyces coelicolor* A3(2)] |
| 4193390 | CspA [*Myxococcus xanthus*] |
| 4193394 | CspC [*Myxococcus xanthus*] |
| 1405478 | CspE protein [*Bacillus cereus*] |
| 1402753 | major cold-shock protein [*Klebsiella pneumoniae*] |
| 2983729 | cold shock protein [*Aquifex aeolicus*] |
| 2815334 | cold-shock domain protein [*Streptomyces coelicolor* A3(2)] |
| 4193398 | CspE [*Myxococcus xanthus*] |
| 4193396 | CspD [*Myxococcus xanthus*] |
| 2894098 | cold shock protein [*Thermotoga maritima*] |
| 15074838 | PUTATIVE COLD SHOCK-LIKE TRANSCRIPTION REGULATOR PROTEIN |
| 1402731 | major cold-shock protein [*Aeromonas hydrophila*] |
| 46789 | 7 kDa cold shock like protein [*Streptomyces clavuligerus*] |
| 9946316 | probable cold-shock protein [*Pseudomonas aeruginosa*] |
| 1402769 | major cold-shock protein [*Proteus vulgaris*] |
| 456240 | major cold shock protein (CspB) [*Sporosarcina globispora*] |
| 19743 | nsGRP-2 [*Nicotiana sylvestris*] |
| 15026046 | Cold shock protein [*Clostridium acetobutylicum*] |
| 11493820 | cold shock protein C [*Yersinia enterocolitica*] |
| 4982460 | cold shock protein [*Thermotoga maritima*] |
| 15979415 | cold shock-like protein [*Yersinia pestis*] |
| 16419455 | similar to CspA but not cold shock induced [*Salmonella typhimurium*] |
| 14523127 | putative cold shock protein [*Sinorhizobium meliloti*] |
| 9107847 | temperature acclimation protein B [*Xylella fastidiosa* 9a5c] |
| 3036806 | glycine-rich protein [*Arabidopsis thaliana*] |
| 2182333 | Y4cH [*Rhizobium* sp. NGR234] |
| 1402733 | major cold-shock protein [*Aeromonas salmonicida*] |
| 9655615 | cold shock-like protein CspD [*Vibrio cholerae*] |
| 3831556 | major cold shock protein [*Enterococcus faecalis*] |
| 3821915 | major cold shock protein [*Lactococcus lactis* subsp. *cremoris*] |
| 15160284 | AGR_L_3376p [*Agrobacterium tumefaciens*] |
| 6458627 | cold shock protein, CSD family [*Deinococcus radiodurans*] |
| 3821923 | major cold shock protein [*Lactobacillus helveticus*] |
| 3821911 | major cold shock protein [*Lactococcus lactis* subsp. *lactis*] |
| 15157349 | AGR_C_4003p [*Agrobacterium tumefaciens*] |
| 15154976 | AGR_C_161p [*Agrobacterium tumefaciens*] |
| 3831558 | major cold shock protein [*Pediococcus pentosaceus*] |
| 456238 | cold shock protein [*Bacillus subtilis*] |
| 117574 | COLD SHOCK-LIKE PROTEIN CSPD (CSP-D) |
| 12620649 | ID534 [*Bradyrhizobium japonicum*] |
| 13424521 | cold-shock domain family protein [*Caulobacter crescentus*] |

-continued

| Genbank ID # | Gene Name |
|---|---|
| 3776223 | CspA [*Sinorhizobium meliloti*] |
| 15075353 | PUTATIVE COLD SHOCK TRANSCRIPTION REGULATOR PROTEIN [*Sinorhizobium* |
| 15075133 | PROBABLE COLD SHOCK TRANSCRIPTION REGULATOR PROTEIN [*Sinorhizobium* |
| 3821913 | major cold shock protein [*Lactococcus lactis* subsp. *lactis*] |
| 13476765 | cold shock protein [*Mesorhizobium loti*] |
| 3821925 | major cold shock protein [*Streptococcus thermophilus*] |
| 3821921 | major cold shock protein [*Lactobacillus acidophilus*] |
| 729222 | COLD SHOCK-LIKE PROTEIN CSPJ |
| 15162334 | AGR_pAT_762p [*Agrobacterium tumefaciens*] |
| 13475232 | cold shock protein [*Mesorhizobium loti*] |
| 9947082 | probable cold-shock protein [*Pseudomonas aeruginosa*] |
| 13424199 | cold-shock domain family protein [*Caulobacter crescentus*] |
| 9948689 | cold-shock protein CspD [*Pseudomonas aeruginosa*] |
| 4193392 | CspB [*Myxococcus xanthus*] |
| 13488430 | cold shock protein [*Mesorhizobium loti*] |
| 12720739 | CspD [*Pasteurella multocida*] |
| 3831560 | major cold shock protein [*Bifidobacterium animalis*] |
| 1513084 | temperature acclimation protein A [*Pseudomonas fragi*] |
| 1169113 | COLD SHOCK-LIKE PROTEIN CSPD |
| 5714745 | cold shock protein 7.4 [*Rhodococcus* sp. 7/1] |
| 1402767 | major cold-shock protein [*Photobacterium phosphoreum*] |
| 14523160 | probable CspA5 cold shock protein transcriptional regulator |
| 15979447 | cold shock-like protein [*Yersinia pestis*] |
| 13488214 | cold-shock protein [*Mesorhizobium loti*] |
| 5714743 | cold shock protein A [*Rhodococcus* sp. 5/14] |
| 3861208 | COLD SHOCK-LIKE PROTEIN (cspA) [*Rickettsia prowazekii*] |
| 81624 | glycine-rich protein 2 - *Arabidopsis thaliana* |
| 15156913 | AGR_C_3315p [*Agrobacterium tumefaciens*] |
| 15074652 | PUTATIVE COLD SHOCK TRANSCRIPTION REGULATOR PROTEIN [*Sinorhizobium* |
| 7295442 | CG17334 gene product [*Drosophila melanogaster*] |
| 3850772 | cold shock protein A [*Lactococcus lactis*] |
| 14334920 | putative glycine-rich zinc-finger DNA-binding protein [*Arabidopsis* |
| 3892588 | cold shock protein C [*Lactococcus lactis*] |
| 2708747 | putative glycine-rich, zinc-finger DNA-binding protein [*Arabidopsis* |
| 2739396 | Y-box protein [*Drosophila melanogaster*] |
| 1402763 | major cold-shock protein [*Photobacterium mondopomensis*] |
| 15620137 | cold shock-like protein [*Rickettsia conorii*] |
| 1402755 | major cold-shock protein [*Lactobacillus casei*] |
| 409419 | Y-Box factor [*Aplysia californica*] |
| 14039811 | Y-box binding protein [*Schistosoma japonicum*] |
| 9946868 | probable cold-shock protein [*Pseudomonas aeruginosa*] |
| 1483311 | Y-box protein [*Dugesia japonica*] |
| 1477478 | Y-box binding protein [*Schistosoma mansoni*] |
| 1402759 | major cold-shock protein [*Listeria innocua*] |
| 15159048 | AGR_L_1288p [*Agrobacterium tumefaciens*] |
| 2228815 | major cold-shock protein CspH [*Salmonella typhimurium*] |
| 6911694 | cold-shock protein A [*Streptococcus thermophilus*] |
| 2970679 | Y box protein [*Drosophila silvestris*] |
| 14602477 | Similar to cold shock domain protein A [*Homo sapiens*] |
| 10727970 | yps gene product [*Drosophila melanogaster*] |
| 1402757 | major cold-shock protein [*Listeria grayi*] |
| 1402751 | major cold-shock protein [*Enterococcus faecalis*] |
| 1083796 | RYB-a protein - rat |
| 505133 | RYB-a [*Rattus norvegicus*] |
| 14523481 | probable CspA6 cold shock protein transcriptional regulator |
| 8100512 | Y-box protein ZONAB-B [*Canis familiaris*] |
| 8100510 | Y-box protein ZONAB-A [*Canis familiaris*] |
| 15306095 | hypothetical protein XP_053028 [*Homo sapiens*] |
| 10185725 | Y-box protein 3 short isoform [*Mus musculus*] |
| 10185723 | Y-box protein 3 long isoform [*Mus musculus*] |
| 7385223 | RNA binding protein MSY4 [*Mus musculus*] |
| 6166110 | DNA-BINDING PROTEIN A (COLD SHOCK DOMAIN PROTEIN A) |
| 1402783 | major cold-shock protein [*Streptococcus pyogenes*] |
| 1167838 | DNA-binding protein [*Homo sapiens*] |
| 1160331 | dbpA murine homologue [*Mus musculus*] |
| 1101884 | YB2 [*Rattus norvegicus*] |
| 950340 | DNA-binding protein A [*Homo sapiens*] |
| 532211 | Y-box binding protein [*Mus musculus*] |
| 87332 | DNA-binding protein A - human (fragment) |

| GenBank ID # | Gene Name |
|---|---|
| 14742409 | hypothetical protein XP_046353 [*Homo sapiens*] |
| 14270385 | cold-shock domain protein [*Takifugu rubripes*] |
| 9653686 | TSH receptor suppressor element-binding protein-1; TSEP-1 |
| 8249978 | cold shock protein B [*Streptomyces coelicolor* A3(2)] |
| 3695368 | zfY1 [*Danio rerio*] |

*Bacillus subtilis* (*B. subtilis*) CspB is a protein that accumulates in response to cold shock (Willimsky, et al. *Journal of Bacteriology* 174:6326 (1992)). It has homology to CspA from *E. coli* (see Table I) and contains a single stranded nucleic acid binding domain (Lopez, et al., The Journal of Biological Chemistry 276:15511 (2001)). Using the same basic Blast search at NCBI (Blink) the following proteins are designated as "hits". The number of hits shown here is limited to 200, but many other proteins would be expected function in the invention.

Table 21. Some cold shock proteins and proteins containing cold shock domains found searching with *B. subtilis* CspB. This list was compiled using the standard Blast Link (Blink) settings at the National Center for Biotechnology Information. The Genbank ID and name of each protein is shown. Note: Due to the way proteins are named, some proteins and sequences will have several entries, as proteins, cDNAs, alleles, etc. Genbank ID can be considered to be specific identifiers of each entry. Entries are in the approximate order of highest to lowest identity to the query sequence.

| GenBank ID # | Gene Name |
|---|---|
| 1421212 | Major Cold Shock Protein (Cspb) |
| 1405476 | CspD protein [*Bacillus cereus*] |
| 729217 | COLD SHOCK PROTEIN CSPB |
| 456240 | major cold shock protein (CspB) [*Sporosarcina globispora*] |
| 1256629 | cold-shock protein [*Bacillus subtilis*] |
| 740006 | cold shock protein |
| 456238 | cold shock protein [*Bacillus subtilis*] |
| 12054789 | cold shock protein (CspLB) [*Listeria monocytogenes*] |
| 1864167 | major cold-shock protein homolog CspB [*Listeria monocytogenes*] |
| 1405472 | CspB protein [*Bacillus cereus*] |
| 8101860 | major cold shock protein CspA [*Staphylococcus aureus*] |
| 16411332 | similar to cold shock protein [*Listeria monocytogenes*] |
| 10176234 | cold-shock protein [*Bacillus halodurans*] |
| 2493766 | COLD SHOCK-LIKE PROTEIN CSPLA (CSPL) |
| 1001878 | CspA protein [*Listeria monocytogenes*] |
| 1405470 | CspA protein [*Bacillus cereus*] |
| 1405474 | CspC protein [*Bacillus cereus*] |
| 13623066 | putative cold shock protein [*Streptococcus pyogenes* M1 GAS] |
| 729220 | COLD SHOCK PROTEIN CSPC |
| 2226349 | CspC [*Staphylococcus aureus*] |
| 9968446 | cold shock protein [*Lactobacillus plantarum*] |
| 1402739 | major cold-shock protein [*Bacillus subtilis*] |
| 3892590 | cold shock protein E [*Lactococcus lactis*] |
| 2226347 | CspB [*Staphylococcus aureus*] |
| 3850776 | cold shock protein D [*Lactococcus lactis*] |
| 1402741 | major cold-shock protein [*Bacillus subtilis*] |
| 15979774 | cold shock protein [*Yersinia pestis*] |
| 10039151 | cold shock-like protein cspE [*Buchnera* sp. APS] |
| 8248794 | cold shock protein [*Streptomyces coelicolor* A3(2)] |
| 460698 | CspC (MsmB) [*Escherichia coli*] |
| 11933043 | cold-shock like protein [*Streptomyces nodosus*] |
| 11933034 | cold-shock like protein [*Streptomyces hygroscopicus*] |
| 1620431 | csp [*Lactobacillus plantarum*] |
| 16419141 | RNA chaperone, negative regulator of cspA transcription [*Salmonella typhimurium* LT2] |
| 15979692 | cold shock protein [*Yersinia pestis*] |
| 2894098 | cold shock protein [*Thermotoga maritima*] |
| 1869948 | cold shock protein [*Lactobacillus plantarum*] |
| 2370256 | cold shock protein [*Lactococcus lactis*] |
| 2970685 | cold shock protein C [*Salmonella typhimurium*] |
| 1778540 | cold shock-like protein [*Escherichia coli*] |
| 471099 | CspE (MsmC) [*Escherichia coli*] |
| 10038996 | cold shock-like protein cspC [*Buchnera* sp. APS] |
| 7242722 | cold shock protein [*Streptomyces coelicolor* A3(2)] |
| 15026046 | Cold shock protein [*Clostridium* acetobutylicum] |
| 15980582 | putative cold shock protein [*Yersinia pestis*] |
| 9657576 | cold shock DNA-binding domain protein [*Vibrio cholerae*] |
| 349561 | DNA-binding protein [*Salmonella typhimurium*] |
| 4982460 | cold shock protein [*Thermotoga maritima*] |
| 1405478 | CspE protein [*Bacillus cereus*] |
| 9946316 | probable cold-shock protein [*Pseudomonas aeruginosa*] |

| GenBank ID # | Gene Name |
|---|---|
| 9658370 | cold shock domain family protein [*Vibrio cholerae*] |
| 5869509 | CspG [*Shewanella violacea*] |
| 1067201 | cold shock protein [*Streptomyces coelicolor*] |
| 9948689 | cold-shockprotein CspD [*Pseudomonas aeruginosa*] |
| 3891780 | Chain A, Major Cold-Shock Protein From *Escherichia Coli* Solution Nmr Structure |
| 576191 | Major Cold Shock Protein 7.4 (Cspa (Cs 7.4)) Of (*Escherichia Coli*) |
| 72232 | major cold shock protein cspA - *Escherichia coli* |
| 9657556 | cold shock transcriptional regulator CspA [*Vibrio cholerae*] |
| 6458627 | cold shock protein, CSD family [*Deinococcus radiodurans*] |
| 3831556 | major cold shock protein [*Enterococcus faecalis*] |
| 15023696 | Cold shock protein [*Clostridium acetobutylicum*] |
| 2425105 | major cold-shock protein [*Micrococcus luteus*] |
| 1402737 | major cold-shock protein [*Bacillus cereus*] |
| 9587215 | cold-shock protein CspA [*Mycobacterium smegmatis*] |
| 7226073 | cold-shock domain family protein [*Neisseria meningitidis* MC58] |
| 4454361 | cold shock protein, CSPA [*Vibrio cholerae*] |
| 479003 | cold-shock protein [*Escherichia coli*] |
| 3097243 | small cold-shock protein [*Mycobacterium leprae*] |
| 1778828 | major cold shock protein CSPA2 [*Yersinia enterocolitica*] |
| 758663 | cold shock protein [*Arthrobacter globiformis*] |
| 2105046 | cspA [*Mycobacterium tuberculosis* H37Rv] |
| 7379745 | putative transcriptional regulator [*Neisseria meningitidis* Z2491] |
| 3249024 | cold shock protein CspB [*Yersinia enterocolitica*] |
| 7210998 | cold-shock protein [*Streptomyces coelicolor* A3(2)] |
| 1513081 | cold acclimation protein B [*Pseudomonas fragi*] |
| 5869504 | CspA [*Shewanella violacea*] |
| 1778825 | major cold shock protein CspA [*Pseudomonas aeruginosa*] |
| 1513086 | temperature acclimation protein B [*Pseudomonas fragi*] |
| 12514257 | homolog of *Salmonella* cold shock protein [*Escherichia coli* O157:H7 EDL933] |
| 5732895 | F40 [*Streptomyces coelicolor* A3(2)] |
| 3831558 | major cold shock protein [*Pediococcus pentosaceus*] |
| 1468921 | cold shock potein CspG [*Escherichia coli*] |
| 13625473 | cold acclimation protein CapB [*Pseudomonas* sp. 30/3] |
| 6073870 | major cold shock protein CSPA1 [*Yersinia enterocolitica*] |
| 1402771 | major cold-shock protein [*Staphylococcus aureus*] |
| 1402761 | major cold-shock protein [*Lactococcus lactis* subsp. *cremoris*] |
| 15981565 | major cold shock protein Cspa1 [*Yersinia pestis*] |
| 9107847 | temperature acclimation protein B [*Xylella fastidiosa* 9a5c] |
| 7321274 | cold shock protein [*Streptomyces coelicolor* A3(2)] |
| 2815334 | cold-shock domain protein [*Streptomyces coelicolor* A3(2)] |
| 2275140 | hypothetical protein [*Yersinia pestis*] |
| 9947082 | probable cold-shock protein [*Pseudomonas aeruginosa*] |
| 2983729 | cold shock protein [*Aquifex aeolicus*] |
| 2961317 | cspB [*Salmonella typhimurium*] |
| 46789 | 7 kDa cold shock like protein [*Streptomyces clavuligerus*] |
| 9107526 | cold shock protein [*Xylella fastidiosa* 9a5c] |
| 1513079 | cold acclimation protein A [*Pseudomonas fragi*] |
| 4193394 | CspC [*Myxococcus xanthus*] |
| 4193392 | CspB [*Myxococcus xanthus*] |
| 3821911 | major cold shock protein [*Lactococcus lactis* subsp. *lactis*] |
| 16503235 | cold shock protein [*Salmonella enterica* subsp. *enterica* serovar *Typhi*] |
| 9957540 | cold shock protein B [*Yersinia enterocolitica*] |
| 3821921 | major cold shock protein [*Lactobacillus acidophilus*] |
| 1616777 | cold shock-like protein [*Stigmatella aurantiaca*] |
| 1402759 | major cold-shock protein [*Listeria innocua*] |
| 4468119 | cold shock protein A; CspA protein [*Bordetella pertussis*] |
| 1742550 | Cold shock-like protein CspB. [*Escherichia coli*] |
| 12720739 | CspD [*Pasteurella multocida*] |
| 3821915 | major cold shock protein [*Lactococcus lactis* subsp. *cremoris*] |
| 1402765 | major cold-shock protein [*Pediococcus pentosaceus*] |
| 1513084 | temperature acclimation protein A [*Pseudomonas fragi*] |
| 4193396 | CspD [*Myxococcus xanthus*] |
| 4193398 | CspE [*Myxococcus xanthus*] |
| 3831560 | major cold shock protein [*Bifidobacterium animalis*] |
| 4193390 | CspA [*Myxococcus xanthus*] |
| 3821923 | major cold shock protein [*Lactobacillus helveticus*] |
| 12720931 | MsmB [*Pasteurella multocida*] |
| 3850772 | cold shock protein A [*Lactococcus lactis*] |
| 9655615 | cold shock-like protein CspD [*Vibrio cholerae*] |
| 9946868 | probable cold-shock protein [*Pseudomonas aeruginosa*] |
| 1402757 | major cold-shock protein [*Listeria grayi*] |
| 3821913 | major cold shock protein [*Lactococcus lactis* subsp. *lactis*] |
| 1402735 | major cold-shock protein [*Bacillus atrophaeus*] |
| 1402751 | major cold-shock protein [*Enterococcus faecalis*] |
| 3892588 | cold shock protein C [*Lactococcus lactis*] |
| 1169113 | COLD SHOCK-LIKE PROTEIN CSPD |
| 15979415 | cold shock-like protein [*Yersinia pestis*] |

-continued

| GenBank ID # | Gene Name |
|---|---|
| 117574 | COLD SHOCK-LIKE PROTEIN CSPD (CSP-D) |
| 15075133 | PROBABLE COLD SHOCK TRANSCRIPTION REGULATOR PROTEIN [*Sinorhizobium meliloti*] |
| 16419455 | similar to CspA but not cold shock induced [*Salmonella typhimurium* LT2] |
| 11493820 | cold shock protein C [*Yersinia enterocolitica*] |
| 1402783 | major cold-shock protein [*Streptococcus pyogenes*] |
| 3821925 | major cold shock protein [*Streptococcus thermophilus*] |
| 1402775 | major cold-shock protein [*Streptococcus dysgalactiae*] |
| 8249978 | cold shock protein B [*Streptomyces coelicolor* A3(2)] |
| 15160284 | AGR_L_3376p [*Agrobacterium tumefaciens*] |
| 81624 | glycine-rich protein 2 - *Arabidopsis thaliana* |
| 19743 | nsGRP-2 [*Nicotiana sylvestris*] |
| 2916930 | cspB [*Mycobacterium tuberculosis* H37Rv] |
| 13475232 | cold shock protein [*Mesorhizobium loti*] |
| 3861208 | COLD SHOCK-LIKE PROTEIN (cspA) [*Rickettsia prowazekii*] |
| 2182333 | Y4cH [*Rhizobium* sp. NGR234] |
| 13476765 | cold shock protein [*Mesorhizobium loti*] |
| 3776223 | CspA [*Sinorhizobium meliloti*] |
| 1402755 | major cold-shock protein [*Lactobacillus casei*] |
| 15620137 | cold shock-like protein [*Rickettsia conorii*] |
| 15154976 | AGR_C_161p [*Agrobacterium tumefaciens*] |
| 15074838 | PUTATIVE COLD SHOCK-LIKE TRANSCRIPTION REGULATOR PROTEIN [*Sinorhizobium meliloti*] |
| 14548150 | RNA-binding cold-shock protein [uncultured crenarchaeote 4B7] |
| 2440094 | small cold-shock protein [*Mycobacterium leprae*] |
| 14523127 | putative cold shock protein [*Sinorhizobium meliloti*] |
| 12620649 | ID534 [*Bradyrhizobium japonicum*] |
| 1063684 | AtGRP2b [*Arabidopsis thaliana*] |
| 13424521 | cold-shock domain family protein [*Caulobacter crescentus*] |
| 3036806 | glycine-rich protein [*Arabidopsis thaliana*] |
| 1402731 | major cold-shock protein [*Aeromonas hydrophila*] |
| 214642 | p54 [*Xenopus laevis*] |
| 15075353 | PUTATIVE COLD SHOCK TRANSCRIPTION REGULATOR PROTEIN [*Sinorhizobium meliloti*] |
| 13424199 | cold-shock domain family protein [*Caulobacter crescentus*] |
| 14602477 | Similar to cold shock domain protein A [*Homo sapiens*] |
| 1175535 | CYTOPLASMIC RNA-BINDING PROTEIN P56 (Y BOX BINDING PROTEIN-2) (Y-BOX TRANSCRIPTION FACTOR) (MRNP4) |
| 104266 | Y box-binding protein 2 - African clawed frog |
| 15157349 | AGR_C_4003p [*Agrobacterium tumefaciens*] |
| 8100512 | Y-box protein ZONAB-B [*Canis familiaris*] |
| 8100510 | Y-box protein ZONAB-A [*Canis familiaris*] |
| 1483311 | Y-box protein [*Dugesia japonica*] |
| 1402767 | major cold-shock protein [*Photobacterium phosphoreum*] |
| 1402733 | major cold-shock protein [*Aeromonas salmonicida*] |
| 15306095 | hypothetical protein XP_053028 [*Homo sapiens*] |
| 14742409 | hypothetical protein XP_046353 [*Homo sapiens*] |
| 14270385 | cold-shock domain protein [*Takifugu rubripes*] |
| 10185725 | Y-box protein 3 short isoform [*Mus musculus*] |
| 10185723 | Y-box protein 3 long isoform [*Mus musculus*] |
| 9653686 | TSH receptor suppressor element-binding protein-1; TSEP-1 [*Rattus* sp.] |
| 7385223 | RNA binding protein MSY4 [*Mus musculus*] |
| 6166110 | DNA-BINDING PROTEIN A (COLD SHOCK DOMAIN PROTEIN A) (SINGLE-STRAND DNA BINDING PROTEIN NF-GMB) |
| 3695368 | zfY1 [*Danio rerio*] |
| 2745892 | Y box transcription factor [*Mus musculus*] |
| 2073109 | Y box protein 1 [*Carassius auratus*] |
| 1353778 | Y-Box binding protein [*Columba livia*] |
| 1167838 | DNA-binding protein [*Homo sapiens*] |
| 1160331 | dbpA murine homologue [*Mus musculus*] |
| 1101884 | YB2 [*Rattus norvegicus*] |
| 1083796 | RYB-a protein - rat |
| 988283 | mYB-1b [*Mus musculus*] |
| 988281 | mYB-1a [*Mus musculus*] |
| 950340 | DNA-binding protein A [*Homo sapiens*] |
| 608518 | p50 [*Oryctolagus cuniculus*] |
| 532211 | Y-box binding protein [*Mus musculus*] |
| 516701 | similar to dbpB/YB-1 of mouse [*Gallus gallus*] |
| 505133 | RYB-a [*Rattus norvegicus*] |
| 457262 | nuclease sensitive element binding protein-1 [*Homo sapiens*] |
| 423015 | nuclease sensitive element-binding protein 1 - human |
| 289797 | YB-1 protein [*Gallus gallus*] |
| 203398 | putative [*Rattus norvegicus*] |
| 199821 | Y box transcription factor [*Mus musculus*] |
| 189299 | DNA-binding protein [*Homo sapiens*] |
| 162983 | transcription factor EF1(A) [*Bos taurus*] |

-continued

| GenBank ID # | Gene Name |
|---|---|
| 115848 | Y BOX BINDING PROTEIN-1 (Y-BOX TRANSCRIPTION FACTOR) (YB-1) (CCAAT-BINDING TRANSCRIPTION FACTOR I SUBUNIT A) (CBF-A) (ENHANCER FACTOR I SUBUNIT A) (EFI-A) (DNA-BINDING PROTEIN B) (DBPB) |
| 112410 | Y box-binding protein 1 - rat |

CSPs are a group of proteins that may or may not be increased in amount when the temperature is lowered or other stress is applied. In fact, in the best studied organism with respect to the cold shock proteins, E. coli, some cold shock proteins are constitutively expressed while others are induced by cold, still others seem to be specific for specific stresses and/or growth conditions or stages. A review of this is Yamanaka, et al., Molecular Microbiology, 27:247 (1998). In this review Yamanaka and colleagues detail how the nine cold shock proteins in E. coli (CspA through CspI) are expressed. CspA, CspB, and CspG are cold inducible. CspD is induced at the stationary phase of the cell cycle and during starvation. CspC and E have been implicated in cell division.

CspA is the major cold shock protein from Escherichia coli (E. coli) (SEQ ID NO:1). CspA is also called Major Cold Shock Protein 7.4. CspA is highly induced in response to cold shock (Goldstein, et al., Proceedings of the National Academy of Science (USA) 87:283 (1990)). In some conditions of slower growth, ribosomes are slowed due to RNA or DNA secondary structure formation, and this may act as a signal for the increased synthesis of CSPs in their native organism. CSPs bind to ssDNA and RNA under in-vitro conditions (Phadtare, et al., Molecular Microbiology 33:1004 (1999)). CSPs are thought to bind to RNA in a relatively non-specific manner during translation and prevent secondary structure formation and stabilize the RNA (this function is sometimes referred as an RNA chaperone). The ribosome can then easily displace the CSPs and initiate translation on a linear RNA template. We believe that the present invention might involve the single stranded nucleic acid binding function of these proteins, and this function can come from any cold shock protein or protein containing a cold shock domain, which includes, for example, prokaryotic cold shock proteins, eukaryotic Y-Box containing genes, some glycine rich proteins (GRP), and other proteins containing the cold shock domain. These proteins include, but are not limited to, those shown in FIG. 4, Trends in Biochemical Science, 23(8):289 (1998) (paper included, herein incorporated by reference). This figure clearly shows the evolutionary relationship between these proteins. The origin of these proteins likely precedes the divergence of modern day bacteria and eukaryotes, and it has been postulated that these proteins may have been present at the advent of single cell evolution, 3.5 billion years ago. We have selected two proteins to transform into plants as examples, as shown in the figure cited above these proteins are more greatly divergent from each other than from many of their eukaryotic counterparts. We expect that the ectopic expression of these proteins may improve tolerance to biotic and abiotic stresses which could include but are not limited to the growth, vigor, yield, and health of plants under a variety of stressful conditions that may include cold, drought, salt stress, heat, survival after cold shock, fungal infection, viral infection, microbial infection, and cold germination.

Another possible explanation for the increased growth rate of plants under stress could be the elicitation of pathogen-associated molecular patterns (PAMP) provided by the expression of CSPs. In this model a plant would develop a PAMP response that would elicit a plant response somewhat like systemic acquired resistance (SAR) (much like SAR works for biotic stresses) as the plant would be "prepared" for the stress prior to its application. For this model to work the plant must be signaled that the CSP is present, this mechanism may have recently been provided through a plant receptor that binds CSP (Felix, et al, Journal of Biological Chemistry 278(8):6201-8 (2003)). This mechanism would mean that any gene that bound a receptor which elicited a PAMP-type response would function in the invention. Elicitation of PAMP-type responses has generally been studied for biotic stresses, and has often been elicited through exogenous administration of agents. Herein we could be eliciting the PAMP-type response to the CSP produced from the CSP transgene. The transgene transformed into a plant cell as part of a recombinant DNA construct, through a particle gun or agrobacterium mediated transformation. This in turn could be creating a systemic acquired resistance type response in the plant, in turn increasing resistance to abiotic stress. This response could work in both monocots and dicots, including but not limited to corn, soybean, wheat, rice, Arabidopsis, canola, and cotton. If the above PAMP method is the mode of action for the CSPs, then the CSP might be expected to provide biotic stress protection as well as abiotic stress protection. None of these mechanisms are meant to be limiting and one or both, or myriad others, could be involved in the phenotype manifested.

MF2, a Csp-like protein from Bacillus thuringensis, has been purported to give some protection against viral infection in a plant. U.S. Pat. No. 6,528,480 shows this tolerance to biotic stress via rubbing the leaves of a plant with an extract containing the protein and infecting the plant with a virus. They contemplate, but do not create, transgenic plants therein.

"Non-transformed plant of the same species" is meant to be inclusive of all plants of the same species as a transformed plant. In one embodiment the transformed plants is of the same species and strain as the transformed plant. In another embodiment the plant is as identical as possible to the transformed plant.

The "cold shock domain" (CSD) is a protein sequence that is homologous to the cold shock proteins. For the purposes of this invention, a cold shock domain containing protein is a "cold shock protein". Greater than 40%, 50%, 60%, 70%, 80%, 90%, 95%, or 98% amino acid identity is seen between E. coli CspA or B. subtilis CspB and the cold shock domains of cold shock domain containing proteins (Wistow, Nature 344:823 (1990); Yamanaka, et al., Mol. Micro., 27:247, specifically see FIG. 1B in the Yamanaka reference; Graumann, et al. TIBS 23:286).

As used herein "yeast" regularly refers to Saccharomyces cerevissiae but could also include Schizosacchoramyces pombe and other varieties (from the genus Pichia, for example). "Corn" refers to Zea Mays and all species and varieties that can be bred with it. "Wheat" refers to all of *Triticum aestivum* varieties including but not limited to spring, winter, and all facultative wheat varieties. "Wheat" includes any other wheat species, including but not limited to durum wheat (*Triticum durum*), spelt (*Triticum spelta*), emmer (*Triticum dicoccum*), and wild wheat (*Triticum monococcum*). "Wheat" also includes any species that can be bred with any of the aforementioned wheat species and offspring of said crosses (including triticale, a hybrid of wheat and rye). "Soybeans" refers to *Glycine max* or *Glycine soja* and any species or variety that can be bred with them. "Rice" refers to *Oryza sativa* and any species or variety that can be bred with it. "Barley" refers to *Hordeum vulgare* and any species or variety that can be bred with it. "Oats" refers to *Avena sativa* and any species or variety that can be bred with it. "Canola" is a coined name recently given to seed, oil, and meal produced by genetically modified rapeseed plants, oilseed rape (*Brassica napus* L.) and turnip rape (*B. campestris* L), herein canola includes all rapeseed plants and organisms that can be bred with them. *E. coli* and *Escherichia coli* as used herein includes organisms of the *Escherichia coli* species and all strains of that this organism; i.e. *E. coli* K12. *E. coli* and *Escherichia coli* as used herein can also includes any organism that can conjugate with any *E. coli* strain when one is an $F^+$ or Hfr strain, and the other is not. *B. subtilis* and *Bacillus subtilis* refers to all organism of the genus *Bacillus*, species *subtilis*.

*Agrobacterium tumifaciens* as used herein includes all strains and types of this species. "Turf grasses" include all species and strains of grass ever planted, or that could be planted, to produce a turf, including but not limited to; a lawn, a field for playing a game (i.e. football, baseball, or soccer), and all areas of a golf course (i.e. tee, fairway, green, rough, etc.). "Cotton" refers to all plants in the genus *Gossypium* and all plants that can be bred with them.

"Heat tolerance" is meant herein as a measure of a plants ability to grow under conditions where heat, or warmer temperature, would detrimentally affect the growth, vigor, yield, size, of the a plant of the same species. Heat tolerant plants grow better under conditions of heat stress than non heat tolerant plants of the same species.

"Salt tolerance" refers to the ability of some plants to grow under osmotic stress, or stress caused by salts or ions in the water and soil. For example, a plant with increased growth rate, compared to a plant of the same species and/or variety, when watered with a liquid, or planted in a media, containing a mix of water and ions that detrimentally affect the growth of another plant of the same species would be said to be salt tolerant. Some transformed plants have a greater tolerance for these types of conditions than non-transformed plants of the same species and strain.

All numbers used herein should be modified by the term "about", about means that the number can vary, in either direction, by up to 10 percent and still retain the same meaning. For example, a 1 M solution should include all solutions of that type less than, and including, 1.1 M and more than 0.9 M. For example, a percentage can also be modified, 10% is inclusive of all percentages from 9% to 11%. Terms defined by the adjective "exactly" are not defined by the term "about".

A "glycine rich protein" is defined as a protein in a eukaryote that is, or has substantial identity with, or is a homologue of, a protein containing a cold shock domain.

"Survival after cold shock" is defined as the ability of a plant to continue growth for a significant period of time after being placed at a temperature below that normally encountered by a plant of that species at that growth stage. It should be noted that some plants, even those of the same species, have been selected for growth under cold conditions. The inbred Wigor strain of corn can tolerate cold conditions and has a significantly higher survival rate when placed in those conditions than most commercial lines sold in the U.S. Wigor is sold commercially in Poland. Thus cold tolerance for transgenic plants must be compared within plants of the same strain at the same relative age, as well as plants of the same species, to gain meaningful scientific data. Plants would then be scored immediately, or some day(s) or week(s) later to determine their viability, growth rate, and other phenotypes after the shock.

"Drought" or "water would be limiting for growth" is defined as a period of dryness that, especially when prolonged, can cause damage to crops or prevent their successful growth. Again different plants of the same species, and those of different strains of the same species, may have different tolerance for drought, dryness, and/or lack of water. In the laboratory drought can be simulated by giving plants 95% or less water than a control plant and looking for differences in vigor, growth, size, root length, and myriad other physiologic and physical measures. Drought can also be simulated in the field by watering some plants, but not others, and comparing their growth rate, especially where water is severely limited for the growth of that plant.

Abiotic stress tolerance includes, but is not limited to, increased yield, growth, biomass, health, or other measure that indicates tolerance to a stress which includes but is not limited to heat stress, salt stress, cold stress (including cold stress during germination), water stress (including but not limited to drought stress), nitrogen stress (including high and low nitrogen).

Biotic stress tolerance includes, but is not limited to, increased yield, growth, biomass, health, or other measure that indicates tolerance to a stress which includes but is not limited to fungal infection, bacterial infection, and viral infection of a plant.

Certain of the gene sequences disclosed as part of the invention are bacterial in origin, for example, certain prokaryotic cold shock proteins. It is known to one skilled in the art that unmodified bacterial genes are sometimes poorly expressed in transgenic plant cells. Plant codon usage more closely resembles that of humans and other higher organisms than unicellular organisms, such as bacteria. Several reports have disclosed methods for improving expression of recombinant genes in plants. These reports disclose various methods for engineering coding sequences to represent sequences which are more efficiently translated based on plant codon frequency tables, improvements in codon third base position bias, using recombinant sequences which avoid suspect polyadenylation or A/T rich domains or intron splicing consensus sequences. While these methods for synthetic gene construction are notable, the inventors have contemplated creating synthetic genes for cold shock proteins or proteins containing cold shock domains according to the method of Brown et al. (U.S. Pat. No. 5,689,052 1997, which is herein incorporated in its entirety by reference) and/or by the above cited, as well as other methods. Thus, the present invention provides a method for preparing synthetic plant genes express in planta a desired protein product. Briefly, according to Brown et al., the frequency of rare and semi-rare monocotyledonous codons in a polynucleotide sequence encoding a desired protein are reduced and replaced with more preferred monocotyledonous codons. Enhanced accumulation of a desired polypeptide encoded by a modified polynucleotide sequence in a monocotyledonous plant is the result of increasing the frequency of preferred codons by analyzing the coding sequence in successive six nucleotide fragments and altering the sequence based on the frequency of appearance of the six-mers as to the frequency of appearance of the rarest 284, 484, and 664 six-mers in monocotyledonous plants. Furthermore, Brown et al. disclose the enhanced expression of a recombinant gene by applying the method for reducing the frequency of rare codons with methods for reducing the occurrence of polyadenylation signals and intron splice to sites in the nucleotide sequence, removing self-complementary sequences in the nucleotide sequence and replacing such sequences with nonself-complementary nucleotides while maintaining a structural gene encoding the polypeptide, and reducing the frequency of occurrence of 5'-CG-3' dinucleotide pairs in the nucleotide sequence. These steps are performed sequentially and have a cumulative effect resulting in a nucleotide sequence containing a preferential utilization of the more-preferred monocotyledonous codons for monocotyledonous plants for a majority of the amino acids present in the desired polypeptide. Specifically all the protein mentioned herein are contemplated to be made into synthetic genes as discussed above, or using similar methods, including but not limited to *Escherichia coli* CspA and *Bacillus subtilis* CspB.

The work described herein has identified methods of potentiating in planta expression of cold shock proteins and proteins containing cold shock domains, which may confer resistance to many plant stresses, which can include but are not limited to cold, heat, drought, salt, and other stresses, or stress related phenotypes (cold germination, survival after cold stress, and other abiotic stresses) when ectopically expressed after incorporation into the nuclear, plastid, or chloroplast genome of susceptible plants. U.S. Pat. No. 5,500,365 (specifically incorporated herein by reference) describes a method for synthesizing plant genes to optimize the expression level of the protein for which the synthesized gene encodes. This method relates to the modification of the structural gene sequences of the exogenous transgene, to make them more "plant-like" and therefore more likely to be translated and expressed by the plant, monocot or dicot. However, the method as disclosed in U.S. Pat. No. 5,689,052 provides for enhanced expression of transgenes, preferably in monocotyledonous plants.

In developing the nucleic acid constructs of this invention, the various components of the construct or fragments thereof will normally be inserted into a convenient cloning vector, e.g., a plasmid that is capable of replication in a bacterial host, e.g., *E. coli*. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

A double-stranded DNA molecule of the present invention containing, for example, a cold shock protein in an expression cassette can be inserted into the genome of a plant by any suitable method. Suitable plant transformation vectors include those derived from a Ti plasmid of *Agrobacterium tumefaciens*, as well as those disclosed, e.g., by Herrera-Estrella et al. (1983), Bevan (1984), Klee et al. (1985) and EPO publication 120,516. In addition to plant transformation vectors derived from the Ti or root-inducing (Ri) plasmids of *Agrobacterium*, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

A plasmid expression vector suitable for the introduction of a gene coding for a cold shock protein, or protein containing a cold shock domain in monocots using electroporation could be composed of the following: a promoter that functions in plants; an intron that provides a splice site to facilitate expression of the gene, such as the Hsp70 intron (PCT Publication WO93/19189); and a 3' polyadenylation sequence such as the nopaline synthase 3' sequence (NOS 3'). This expression cassette may be assembled on high copy replicons suitable for the production of large quantities of DNA.

An example of a useful Ti plasmid cassette vector for plant transformation is pMON-17227. This vector is described in PCT Publication WO 92/04449 and contains a gene encoding an enzyme conferring glyphosate resistance (denominated CP4), which is an excellent selection marker gene for many plants. The gene is fused to the *Arabidopsis* EPSPS chloroplast transit peptide (CTP2) and expressed from the FMV promoter as described therein. When an adequate numbers of cells (or protoplasts) containing the sedoheptulose-1,7-bisphosphatase gene or cDNA are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans.

Plants that can be made to express cold shock proteins by practice of the present invention include, but are not limited to, *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassaya, cauliflower, celery, cherry, cilantro, citrus, clementines, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, zucchini, or any other plant.

"Promoter" refers to a DNA sequence that binds an RNA polymerase (and often other transcription factors) and promotes transcription of a downstream DNA sequence. Promoters are often provide enhanced or reduced expression in some tissues when compared to others. Promoter selection, specifically selecting promoters that increase expression when a plant is undergoing abiotic stress could be particularly useful in the instant invention.

It has been observed in the art that some stress responses have similar effects on the plant, and resistance to one may provide resistance to another. This is seen, for example, between the responses to dehydration and low temperature (Shinozaki, et al., Current Opinions in Plant Biology 3(3): 217, 2000). Many other papers show the general interrelationship between different abiotic stresses, and might indicate that tolerance to one stress might lead to greater tolerance of several other abiotic stresses (Pernas, et al., FEBS Lett 467 (2-3):206, 2000; Knight, Int Rev Cytol 195:269, 2000; Didierjean, et al., Planta 199: 1, 1996; Jeong, et al., Mol Cells 12:185, 2001).

Expression cassettes and regulatory elements found in the DNA segment outside of the plant expression elements contained in the T-DNA are common in many plasmid DNA backbones and function as plasmid maintenance elements, these include, but are not limited to, the aad (Spc/Str) gene for bacterial spectinomycin/streptomycin resistance, the pBR322 on (ori322) that provides the origin of replication for maintenance in E. coli, the born site for the conjugational transfer into the Agrobacterium tumefaciens cells, and a DNA segment is the 0.75 kb oriV containing the origin of replication from the RK2 plasmid. In addition, those plasmids intended for transformation into plants often contain the elements necessary for the endogenous DNA integration proteins of Agrobacterium to function to insert the element. These include borders (right (RB) and left (LB) borders).

The laboratory procedures in recombinant DNA technology used herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y. (1989).

All publications and published patent documents cited in this specification are incorporated herein by reference to the same extent as if each individual publication or patent application is specifically and individually indicated to be incorporated by reference.

The following examples are included to demonstrate embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention, therefore all matter set forth or shown in the accompanying drawings and examples is to be interpreted as illustrative and not in a limiting sense.

EXAMPLES

Figure 2:
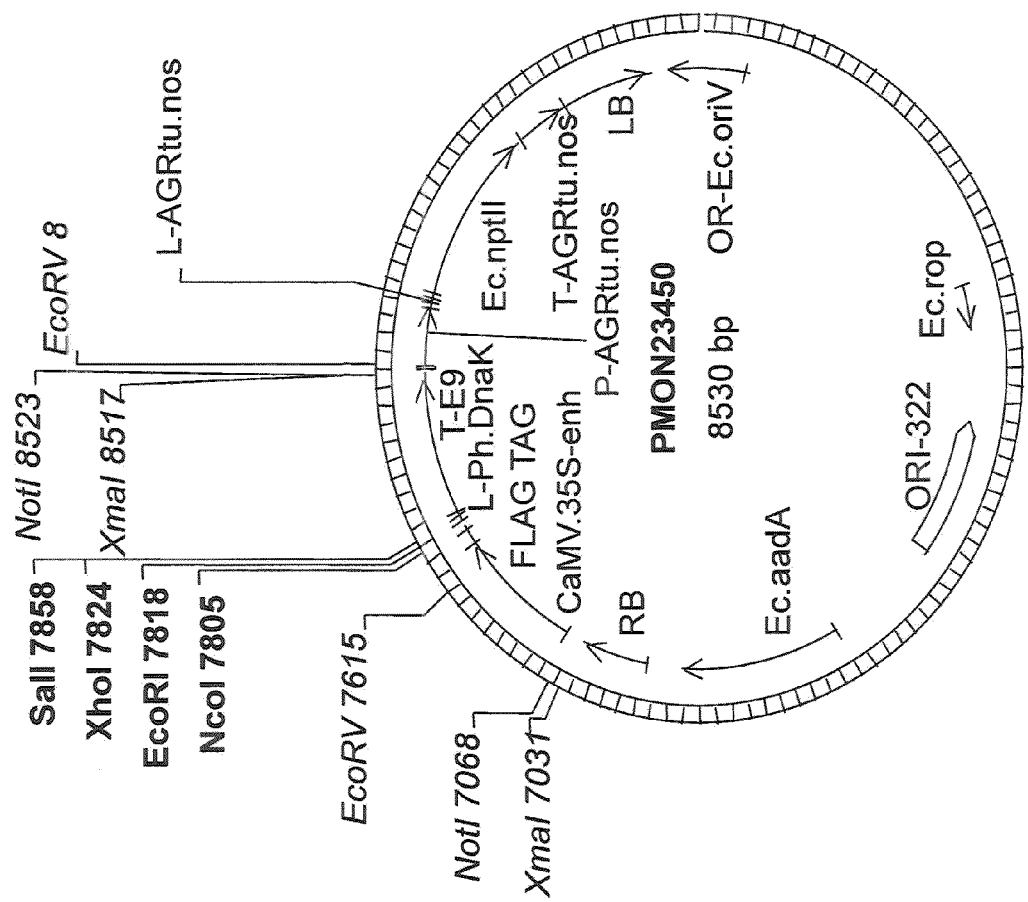
FIG. 2 shows a plasmid map of pMON23450.

Example 1 pMON57396 (FIG. 1) is a binary vector for Agrobacterium-mediated transformation and constitutive expression of a protein (SEQ ID NO: 56) similar to Escherichia coli CspA in Arabidopsis. To clone the E. coli CspA gene, two gene specific primers, MF1 and MF2, were designed based on the CspA sequence information (Genbank M30139, GI:409136) from the National Center for Biotechnology Information, which is part of the National Library of Medicine, in turn part of the National Institutes of Health (NCBI). The sequence for MF1 is AGGTAATACACCATGGCCGGTAA (SEQ ID NO: 66), which anneals at the translational start site of CspA and introduces an NcoI site at the 5' end, while the sequence of MF2 is TTAAGCAGAGAATTCAGGCTGGTT (SEQ ID NO: 67), which anneals at the last codon of CspA and introduces an EcoRI site at the end of the primer. PCR was performed to isolate E. coli CspA. Specifically, E. coli DH5α cells were lysed and a small amount of the lysate was used as a template to amplify the CspA gene using MF1 and MF2 primers, Taq polymerase and dNTPs from Roche Molecular Biochemicals (Indianapolis, Ind.). The thermal cycling conditions were as follows: 94° C., 1 min, followed by 30 cycles of 94° C., 16 seconds; 55° C., 1 min and 72° C., 1 min. The amplified CspA DNA was purified by gel-electrophoresis, digested with NcoI and EcoRI and ligated to a binary vector pMON23450 (FIG. 2) that had previously been linearized by digestion with NcoI and EcoRI. Ligation was performed using T4 ligase and following procedures recommended by the manufacturer (BRL/Life Technologies, Inc., Gaithersburg, Md.). The ligation mix was transformed into E. coli cells for plasmid propagation (Sambrook et al., Molecular Cloning: A Laboratory Manual, 2$^{nd}$ Edition, Cold Spring Harbor Press, 1989). The transformed cells were plated on appropriate selective media (Sambrook et al., Molecular Cloning: A Laboratory Manual, 2$^{nd}$ Edition, Cold Spring Harbor Press, 1989) and colonies were scored hours or days later. Plasmids were prepared from individual colonies and full-insert sequence was determined.

The resulting plasmid was also confirmed by restriction mapping (for example, see Griffiths, et al, An Introduction to Genetic Analysis, 6$^{th}$ Edition pp 449-451, ISBN 0-7167-2604-1, W.H. Freeman and Co., New York) and sequencing. As the chosen NcoI-EcoRI cloning site in the vector was flanked by a CaMV e35S promoter at the upstream (5') and an epitope tag (Flag, which encodes the oligopeptide DYKDDDK (SEQ ID NO: 68), SIGMA, St Louis) at the downstream (3'), the E. coli CspA in this construct is thus tagged at the C-terminus by the Flag epitope tag and will be driven transcriptionally by the CaMV e35S promoter upon transformation in Arabidopsis. The above cloning results in a plasmid encoding a protein similar to SEQ ID NO: 55. The resulting plasmid is called pMON57396.

Example 2 pMON57397 (FIG. 2) is a binary vector for Agrobacterium-mediated transformation and constitutive expression of a protein (SEQ ID NO: 57), like Escherichia coli CspA protein, in Arabidopsis. To create pMON57397, the binary vector pMON57396 containing the Escherichia coli CspA gene (see example above) tagged at the C-terminus by the Flag epitope tag, was digested with restriction enzymes XhoI and SalI to cleave these sites in the vector and release the FLAG epitope tag (The FLAG tag encodes the oligopeptide DYKDDDK, SIGMA, St Louis). The linearized plasmid was then purified and religated. Ligation was performed using T4 ligase and following procedures recommended by the manufacturer (BRL/Life Technologies, Inc., Gaithersburg, Md.). The ligation mix was transformed into E. coli cells for plasmid propagation (Sambrook et al., Molecular Cloning: A Laboratory Manual, 2$^{nd}$ Edition, Cold Spring Harbor Press, 1989). The transformed cells were plated on appropriate selective media (Sambrook et al., Molecular Cloning: A Laboratory Manual, 2$^{nd}$ Edition, Cold Spring Harbor Press, 1989) and colonies were scored hours or days later. Plasmids were prepared from individual colonies and full-insert sequence was determined. The cloning above results in the creation of a plasmid encoding a protein similar to SEQ ID NO: 57.

The resulting plasmid was also confirmed by restriction mapping to ensure that XhoI and SalI sites were absent (for example, see Griffiths, et al, An Introduction to Genetic Analysis, 6$^{th}$ Edition pp 449-451, ISBN 0-7167-2604-1, W.H.

Freeman and Co., New York) and sequencing. The *E. coli* CspA gene in this construct is untagged at the C-terminus and is driven transcriptionally by the CaMV e35S promoter.

Example 3 pMON57398 (FIG. 4) is a binary vector for *Agrobacterium*-mediated transformation and constitutive expression of a protein (SEQ ID NO: 59) like *Bacillus subtilis* CspB, in *Arabidopsis*. To clone the *B. subtilis* CspB gene, two gene-specific primers, MF3 and MF4a, were designed based on the CspB sequence information (Genbank U58859, gi:1336655) from the National Center for Biotechnology Information, which is part of the National Library of Medicine, in turn part of the National Institutes of Health (NCBI). The sequence for MF3 is AGGAGGAAATTCCATGGTAGAAG (SEQ ID NO: 69), which anneals at the translational start site of CspB and introduces an NcoI site at the 5' end, while the sequence of MF4a is TCAATTTATGAATTCGCTTCTTTAGT (SEQ ID NO: 70), which anneals at the last codon of CspB and introduces an EcoRI site at the end of the primer. PCR was performed to isolate *B. subtilis* CspB. *Bacills subtilis* cells were obtained from Carolina Biological Supply (Burlington, N.C.), the cells were lysed and a small amount of the lysate was used as a template to amplify the CspB gene using MF3 and MF4a primers, Taq polymerase and dNTPs from Roche Molecular Biochemicals. The thermal cycling conditions were as follows: 94° C., 1 min, followed by 30 cycles of 94° C., 16 seconds; 55° C., 1 min and 72° C., 1 min. The amplified CspB DNA was purified by gel-electrophoresis, digested with NcoI and EcoRI and ligated to a binary vector pMON23450 (FIG. 5) that had previously been linearized by digestion with NcoI and EcoRI. Ligation was performed using T4 ligase and following procedures recommended by the manufacturer (BRL/Life Technologies, Inc., Gaithersburg, Md.). The ligation mix was transformed into *E. coli* cells for plasmid propagation. The transformed cells were plated on appropriate selective media (Sambrook et al., *Molecular Cloning: A Laboratory Manual, 2nd Edition*, Cold Spring Harbor Press, 1989) and colonies were scored a day later. Plasmids were prepared from individual colonies and full-insert sequence was determined.

The resulting plasmid was also confirmed by restriction mapping (for example, see Griffiths, et al, *An Introduction to Genetic Analysis, 6th Edition* pp 449-451, ISBN 0-7167-2604-1, W.H. Freeman and Co., New York) and sequencing. As the chosen NcoI-EcoRI cloning site in the vector was flanked by a CaMV e35S promoter at the upstream (5') and an epitope tag (Flag, which encodes the oligopeptide DYKDDDK (SIGMA, St Louis) at the downstream (3'), the *B. subtilis* CspB like gene in this construct is thus tagged at the C-terminus by the Flag epitope tag and will be driven transcriptionally by the CaMV e35S promoter upon transformation in *Arabidopsis*. This cloning results in a plasmid with the sequence encoding a protein similar to SEQ ID NO: 59 being inserted into said plasmid.

Figure 6:
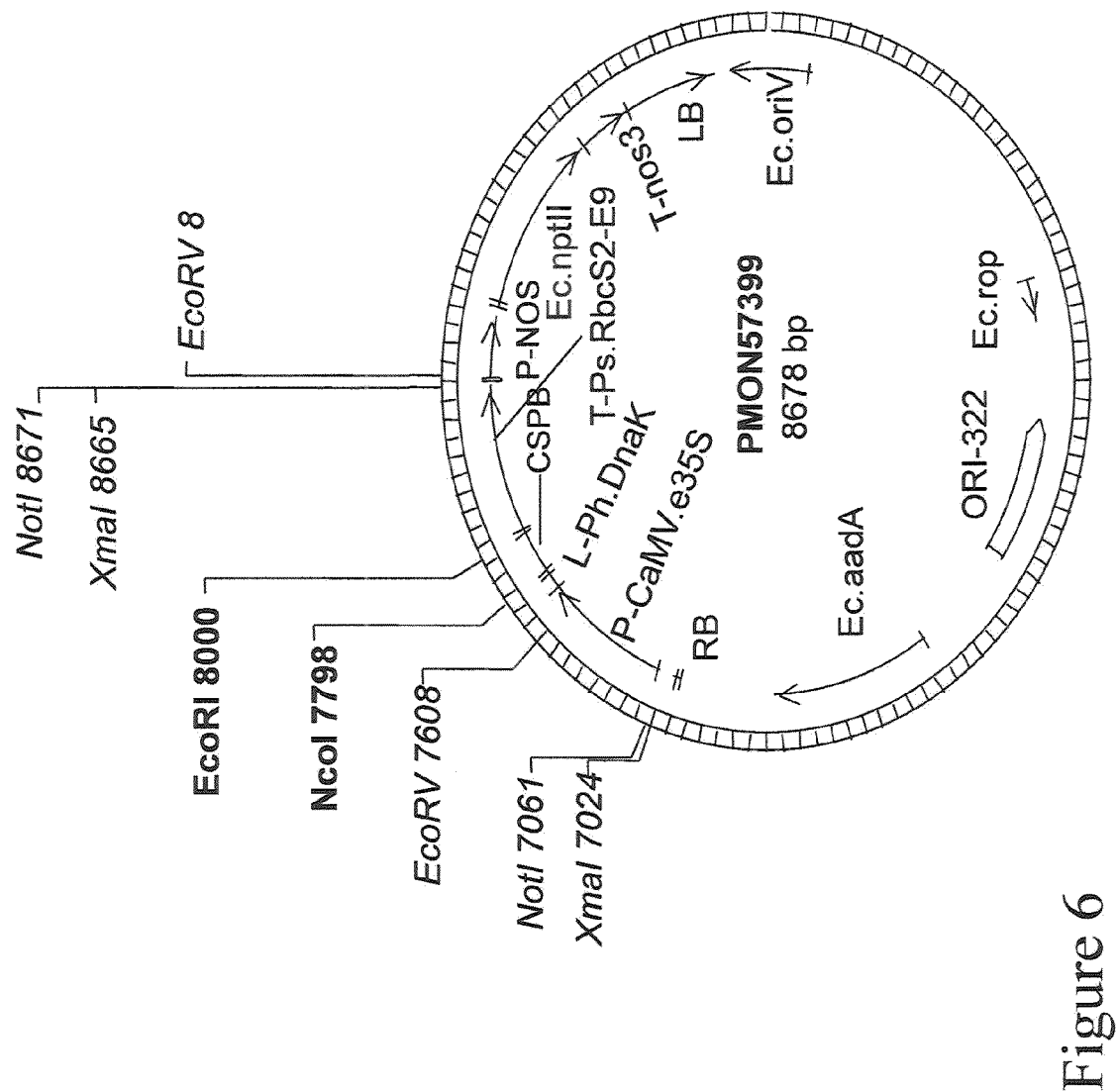
FIG. 6 shows a plasmid map of pMON57399.

Example 4 pMON57399 (FIG. 6) is a binary vector for *Agrobacterium*-mediated transformation and constitutive expression of a protein (SEQ ID NO: 61) like *Bacillus subtilis* CspB in *Arabidopsis*. To create pMON57399, the binary vector pMON57398 containing the *Bacillus subtilis* CspB gene (see example above) tagged at the C-terminus by the Flag epitope tag, was digested with restriction enzymes XhoI and SalI to cleave these sites in the vector and release the FLAG epitope tag (The FLAG tag encodes the oligopeptide DYKDDDK, SIGMA, St Louis). The linearized plasmid was then purified and religated. Ligation was performed using T4 ligase and following procedures recommended by the manufacturer (BRL/Life Technologies, Inc., Gaithersburg, Md.). The ligation mix was transformed into *E. coli* cells for plasmid propagation (Sambrook et al., *Molecular Cloning: A Laboratory Manual, 2nd Edition*, Cold Spring Harbor Press, 1989). The transformed cells were plated on appropriate selective media (Sambrook et al., *Molecular Cloning: A Laboratory Manual, 2nd Edition*, Cold Spring Harbor Press, 1989) and colonies were scored hours or days later. Plasmids were prepared from individual colonies and full-insert sequence was determined. This cloning results in a plasmid with a sequence encoding a protein similar to SEQ ID NO: 61 being inserted into said plasmid.

The resulting plasmid was also confirmed by restriction mapping to ensure that XhoI and SalI sites were absent (for example, see Griffiths, et al, *An Introduction to Genetic Analysis, 6th Edition* pp 449-451, ISBN 0-7167-2604-1, W.H. Freeman and Co., New York) and sequencing. As the chosen NcoI-EcoRI cloning site in the vector was flanked by a CaMV e35S promoter at the upstream (5') N-terminus, the *B. subtilis* CspB gene in this construct is untagged at the C-terminus and is driven transcriptionally by the CaMV e35S promoter upon transformation in *Arabidopsis*. Said plasmids were transformed into *Agrobacterium tumefaciens*.

Example 5

*Arabidopsis* plants may be transformed by any one of many available methods. For example, *Arabidopsis* plants may be transformed using In planta transformation method by vacuum infiltration (see, Bechtold et al., *In planta Agrobacterium* mediated gene transfer by infiltration of adult *Arabidopsis thaliana* plants. CR Acad. Sci. Paris Sciences de la vie/life sciences 316: 1194-1199 (1993). This example illustrates how *Arabidopsis* plants may be transformed.

Stock Plant Material and Growth Conditions

Prepare 2.5 inch pots with soil and cover them with a mesh screen, making sure that the soil is not packed too tightly and the mesh is in contact with the soil surface (this ensures that the germinating seedlings will be able to grow through the mesh). Sow seeds and cover with a germination dome. Vernalize seeds for 3-4 days. Grow plants under conditions of 16 hours light/8 hours dark at 20-22° C., 70% humidity. Water twice weekly, and fertilize from below with ½× (half of the strength recommended by the manufacturer) Peters 20-20-20 fertilizer (from Hummert International, Earth City, Mo.). Add micronutrients (Hummert's Dyna-grain Soluble Trace Elements) (in full strength recommended by the manufacturer) every other week. After about 1-2 weeks, remove the dome and thin the pots to one or two plants per pot. Clip the primary bolt, when it develops, to encourage more secondary bolt formation. In 5-7 days the plants will be ready for infiltration.

Agrobacterium Preparation (Small Scale and Large Scale Cultures):

*Agrobacterium* strain ABI is streaked onto an LB plate containing Spectinomycin 100 mg/L, Streptomycin 100 mg/L, Chloramphenicol 25 mg/L, and Kanamycin 50 mg/L (denoted SSCK). Two days prior to infiltration, a loop of *Agrobacterium* is placed into a tube containing 10 mls LB/SSCK and put on a shaker in the dark at 28° C. to grow overnight. The following day, the *Agrobacterium* is diluted 1:50 in 400 mls YEP/SSCK and put on a shaker at 28° C. to grow for 16-20 hours. (Note: we have found the transformation rate is significantly better when LB is used for the first overnight growth and YEP is used for the large scale overnight culture).

Infiltration

Harvest the *Agrobacterium* cells by pouring into a 500 ml centrifuge bottle and spinning at 3500 rpm for 20-25 minutes. Pour off the supernatant. Dry the pellet and then resuspend in 25 ml Infiltration Medium (MS Basal Salts 0.5%, Gamborg's B-5 Vitamins 1%, Sucrose 5%, MES 0.5 g/L, pH 5.7) with 0.44 nM benzylaminopurine (BAP) (10 μl of a 1.0 mg/L stock in DMSO per liter) and 0.02% Vac-In-Stuff (Silwet L-77) from Lehle Seeds (Round Rock, Tex.). The BAP and Silwet L-77 are added fresh the day of infiltration. Add 200 d of Silwet L-77, and 200 μl of BAP (0.5 mg/L stock). Using Infiltration Medium as your blank, take the ($OD_{600}$ of a 1:10 dilution of the *Agrobacterium* suspensions. Calculate the volume needed for 400 ml of *Agrobacterium* suspension/infiltration medium, OD600=0.6, for the vacuum infiltration.

$$\text{Equation: } \frac{(\text{final volume}) * (\text{final } OD600)}{OD600} =$$

Volume needed for final OD600 of 0.6

Place resuspended culture in a Rubbermaid container inside a vacuum dessicator. Invert pots containing plants to be infiltrated into the solution so that the entire plant is covered, including the rosette, but not too much of the soil is submerged. Soak the plants with water for at least 30 min. prior to infiltration. (This keeps the soil from soaking up the *Agrobacterium* suspension).

Draw a vacuum of ~23-27 in. Hg for 10 min. Quickly release the vacuum. Briefly drain the pots, place them on their sides in a diaper-lined tray, cover the tray with a dome to maintain humidity, and return to growth chamber. The following day, uncover the pots, set them upright, and remove the diaper. Do not water plants for ~5 days. After the 5 days are up, allow the plants to be watered and to continue to grow under the same conditions as before. (The leaves that were infiltrated may degenerate but the plant should survive until it is finished flowering).

Harvesting and Sterilizing Seed

Cone the plants, individually, by using the Lehle Aracons (Lehle Seeds, Round Rock, Tex.) approximately 2 weeks after infiltration. After all of the seed is matured and has set (~4 weeks post-infiltration), remove the plants from water to dry down the seeds. Approximately 2 weeks later harvest the seeds by cutting the branches below the cone. Clean the seed by using a sieve to catch the silique and branch material and allow the seed to go through. Place the seed in an envelope or in 15 ml conical tubes.

Transfer desired amount of seeds to 15 ml conical tubes prior to sterilization. Loosen the lid to the conicals and place them on their side in a vacuum dessicator with a beaker containing 400 ml of bleach Clorox (Clorox Company, Oakland, Calif.) and 4 ml of Hydrochloric Acid. (Add the HCl to the Clorox in a fume hood). Pull a vacuum just to seal the dessicator, and close the suction (i.e. so that the dessicator is still under a vacuum but the vacuum is not still being directly pulled) for ~16 hrs. After sterilization, release the vacuum and place tubes containing seed in a sterile hood (keep caps loose so gas can still be released).

Plate ("sprinkle") the seed on selection plates containing MS Basal Salts 4.3 g/L, Gamborg's B-5 (500×) 2.0 g/L, Sucrose 10 g/L, MES 0.5 g/L, and 8 g/L Phytagar (Life Technologies, Inc., Rockville, Md.) with Carbenicillin 250 mg/L, Cefotaxime 100 mg/L. Selection levels will either be kanamycin 60 mg/L, Glyphosate 60 μM, or Bialaphos 10 mg/L.

A very small amount of seed can be first plated out to check for contamination. If there is contamination, re-sterilized seeds for ~4 more hours and check for contamination again. The second sterilization is usually not necessary, but sometimes the seed harbors a fungal contaminant and repeat sterilizations are needed. (The sterilization duration generally is shorter than 16 hours because of significantly decreased germination rates starting at 24 hr. sterilization duration). Seal plates with parafilm and place in a cold room to vernalize for ~2-4 days. After seeds are vernalized, place in percival with cool white bulbs.

Transfer to Soil

After 5-10 days at ~26° C. and a 16/8 light cycle, the transformants will be visible as green plants. After another 1-2 weeks, plants will have at least one set of true leaves. Transfer plants to soil, cover with a germination dome, and move to a growth chamber with normal *Arabidopsis* growth conditions. Keep covered until new growth is apparent (usually 5-7 days).

Example 6

In order to compare the growth of wildtype non-transgenic and CspA or CspB transgenic *Arabidopsis* plants, vertical growth was allowed in sterile Petri dishes:

Wildtype or transgenic seeds were liquid sterilized using the following method:

5 minute incubation in 70% ethanol following vortex mixing 5 minute incubation in 30% Chlorox (6.15% sodium hypochlorite)+0.01% Triton X-100 following vortex mixing 5 consecutive sterile water washes Seeds were plated onto plastic, 100×15 mm square petri dishes (Becton Dickinson-Falcon #35-1112), each containing 40 ml of agar media made as follows:

0.5× Murashige and Skoog media with macronutrients, micronutrients and vitamins (Sigma #M5519), adjusted to pH 5.8 with ammonium hydroxide and containing 1% Phytagel (Sigma # P8169) for solid support.

Ten wild type *Arabidopsis* seeds were plated across one half of a petri dish, approximately 1 cm from the edge and evenly spaced. This was done with a Gilson P-200 Pipetteman using sterile tips. Ten CspA or CspB transgenic *Arabidopsis* seeds were similarly plated across the other half of the petri dish, evenly spaced. The plates were labeled with a marking pen to indicate which half contained the transgenic seeds.

Figure 16:
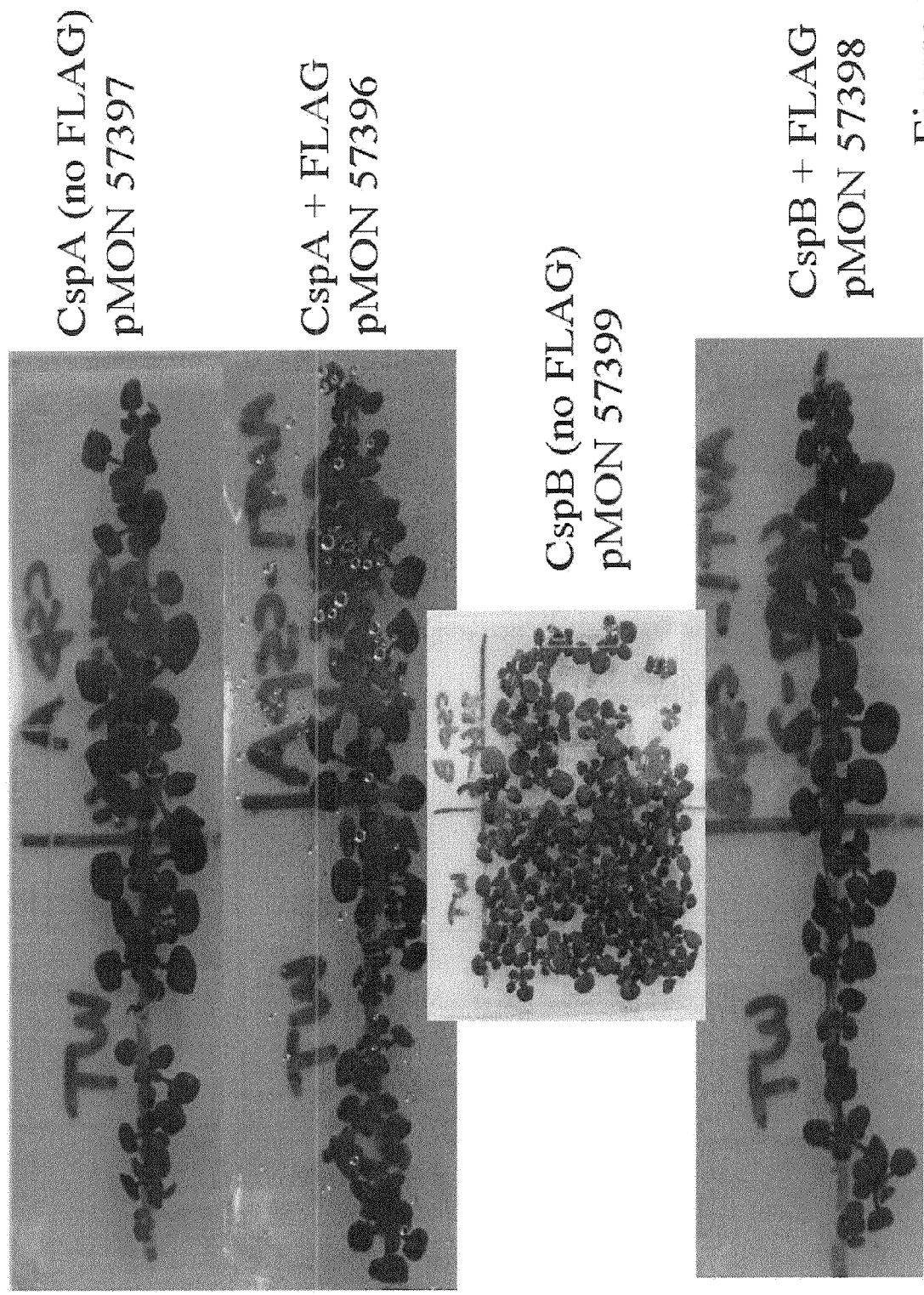
FIG. 16 shows the growth pattern of plants expressing the indicated gene, and controls, showing that the genes introduced provide abiotic stress tolerance.

The petri dishes were put at 4° C. for 3 days in the dark to stratify the seeds and then placed in a Percival incubator (model AR-36L) at 8° C. for 6 weeks at 24 hour constant light of 120 microeinsteins/square meter. At the end of this incubation, the size of the CspA and CspB rosettes were compared to that of wildtype and found to be larger. This can be seen in FIG. 16. This can be seen in the first, second, and last pictured plate where the above assay was used. In FIG. 16, the third picture (CspB+Flag, pMON57399) displays a plate wherein the plants were put through a cold shock assay similar to that described below.

Cold Shock Seedling Vigor Assessment of Transgenic *Arabidopsis thaliana* Seeds: Horizontal Plate Assay.

Introduction:

This is a procedure for assessing the ability of transgenic *Arabidopsis* seeds that have germinated at normal temperatures on media agar in horizontal petri plates to continue to grow upon a shift to chilling. In short, seeds from control plants and seeds from tester transgenic plants are sterilized, stratified, and plated in 6×8 grids on either half of a petri dish. The plate is incubated at normal temperature in a horizontal position for one week and then shifted to chilling temperature for two additional weeks, maintaining the horizontal position of the plate. The canopy area of seedlings is recorded by digital photography and quantitated using imaging software. The ratio of the total canopy area of the tester seedlings to that of the control seedlings can be used as a quantitative parameter to compare the cold tolerance potential of various genes of interest in transgenic tester lines.

Materials: the Following Assumes the Normal Capital Equipment Available in a Standard Biotechnology Laboratory (Autoclave, Balance, Laminar Flow Hood, Etc.)

- Arabidopsis seed: the protocols here have been used with Arabidopsis thaliana cv. Columbia, but ought to be suitable for other Arabidopsis species as well.
- Petri dishes:Falcon #35-1112 (100 mm square×15 mm deep)
- Media: Sigma M5519=Murashige & Skoog Basal Media
- Phytagel (Sigma #P-8169)
- 1-liter glass bottles in which to autoclave media agar and from which to pour plates. We use Corning glass bottles with the orange screw caps.
- Magnetic stirrers and magnetic stir bars
- Electric pipettor usable with 50 ml plastic pipettes.
- Small fluorescent light box with plastic magnifying lense for plating seeds.
- P1000 Gilson pipetor (or equivalent) and sterile tips
- P200 Gilson pipetor (or equivalent) and sterile tips
- 70% Ethanol, sterile
- 30% Chlorox bleach+0.1% Tween 20
- Sterile filtered deionized water
- Sterile microcentrifuge tubes and tube racks
- 4° C. cold room, cold box or refrigerator, preferably dark
- 22 degrees C. Percival plant growth chamber or equivalent with ~150 µE/m$^2$/sec light source
- 8 degress C. Percival plant growth chamber or equivalent with ~150 µE/m$^2$/sec light source
- Semipermeable surgical tape 3M Micropore tape (3M #1530-1)
- Black (Sharpie) marker
- Vacuum aspirator with trap
- Glassine balance weighing paper (VWR #12578-165)
- Calculator
- Notebook
- IBM compatible computer
- Image-Pro Plus software, version 4.1.0.0
- Microsoft Excel software Protocol:

1—Aliquot seeds for storage vials or envelopes to sterile microcentrifuge tubes
2—Label tubes with sharpie to retain identity of seeds
3—Surface sterilize seeds in tubes by successive washing with the following solutions and waiting times listed below. Note, invert tubes during washings at least twice to ensure good surface contact of solutions on seeds. Seeds will fall down to the bottom of the tube, making a soft pellet:
  a. 70% Ethanol, sterile, for 3 to 5 minutes
  b. 30% Chlorox bleach+0.1% Tween 20, for 3 to 5 minutes
  c. Sterile filtered deionized water, for 30 seconds
  d. Repeat c. four more times and on the last time, leave ~0.5 ml of sterile water remaining over the seed pellet.

1—Place microcentrifuge tubes in the dark at 4° C. for three days to stratify the seeds for more uniform germination upon plating.
[Alternatively, the seeds can be directly plated onto media agar petri dishes, taped sealed and the petri dish can be put at 4° C. in the dark for three days prior to the 8° C. cold incubation—see below.]
2—Make plates by preparing 1-liter aliquots of 0.5× Murashige and Skoog media in the glass bottles, adjust pH to 5.8 with ammonium hydroxide, then add 10 grams of Phytagel. Use a magnetic stirrer when adjusting the pH and to mix in the phytagel uniformly, then autoclave on liquid setting (slow exhaust) for 45 minutes.
3—Pour plates in the laminar flow hood using the electric pipettor with the 50 ml sterile pipette to deliver 40 ml of media to each plate, immediately covering the plate with the lid.
4—Allow plates to cool in laminar flow hood for at least 2 hours with the blower off and store in dated plastic bags at 4° C.
5—Label plates and plate seeds:
1—Tape all four edges of the plate with semipermeable micropore tape, label with the date and put plates in a Percival incubator set at 22 C and 16 hour day light cycle at ~100 µE/m$^2$ sec. Place the plates in a horizontal position only one layer thick and incubate for 7 days. Photograph each plate with a digital camera and store the data to a compact disk.
2—Transfer plates to a Percival incubator set at 8° C. and 24 hour day light cycle at ~100 µE/m$^2$ sec, Place the plates in a horizontal position only one layer thick and incubate for upto 3 additional weeks. Photograph each plate with a digital camera and store the data to a compact disk.
3—Observe plates every 2 to 3 days to see how tester germplasms are proceeding compared to controls and digitally photograph at times that are representative of the general performance of the germplasms. This should take less than 2 weeks (3 weeks at the most) of incubation at 8° C. Those germplasms that take longer to show a difference need to be plated at a lower seed density to avoid overcrowding at the time the digitial photograph is taken.
4—Measure rosette canopy area using digital camera photography and Image-Pro Plus software. Calculate the average seedling canopy for control and tester populations, eliminating seeds from the analysis that never germinated. Calculate the ratio between the average seedling canopy area post temperature shift for the control seedlings and the tester seedlings, the standard deviation and standard error for control and tester seedling sets. Ascertain if there is a statistical difference between the tester seedlings and the control seedlings. Record results in a notebook.
5—Discard plates and seedlings in appropriate disposal containers for transgenic plant materials (gray bins with clear plastic waste bags).

Example 7

Figure 7:
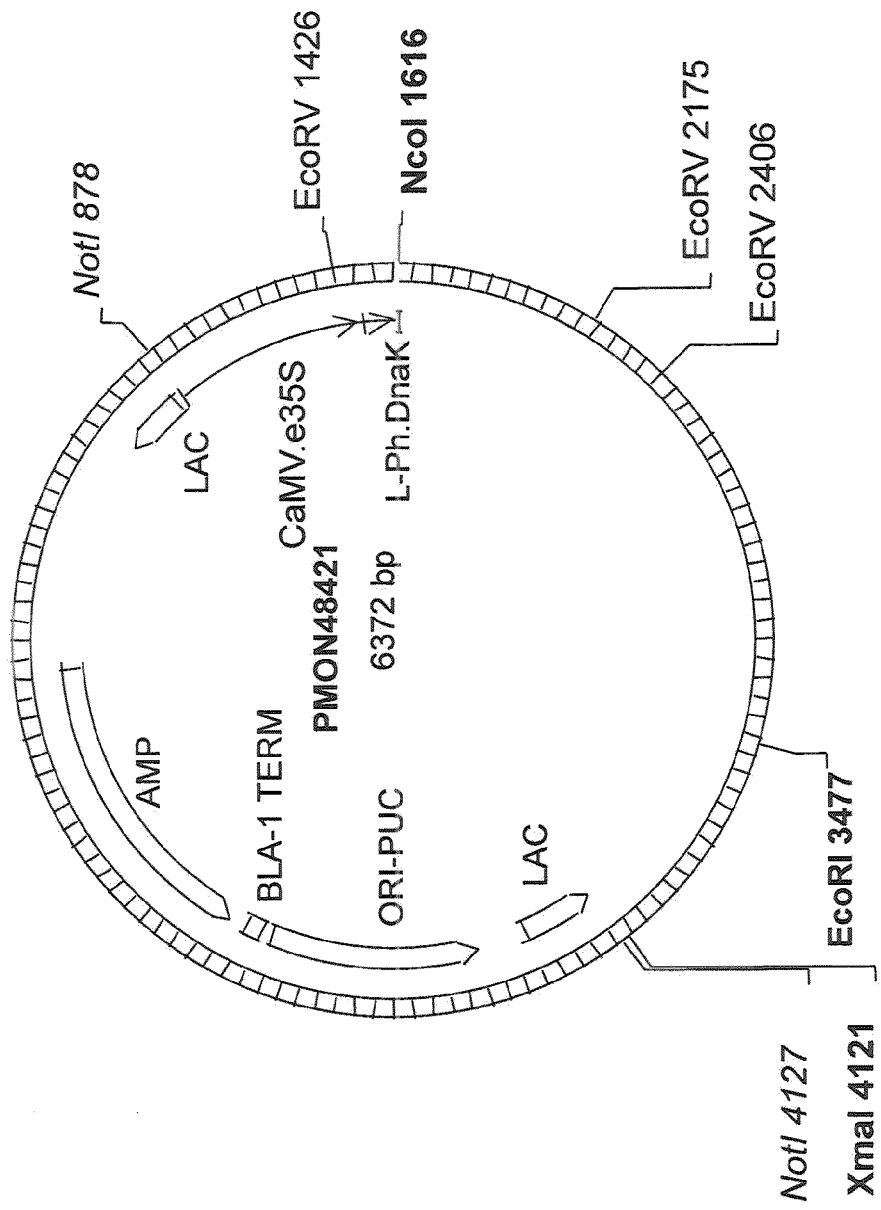
FIG. 7 shows a plasmid map of pMON48421.
Figure 8:
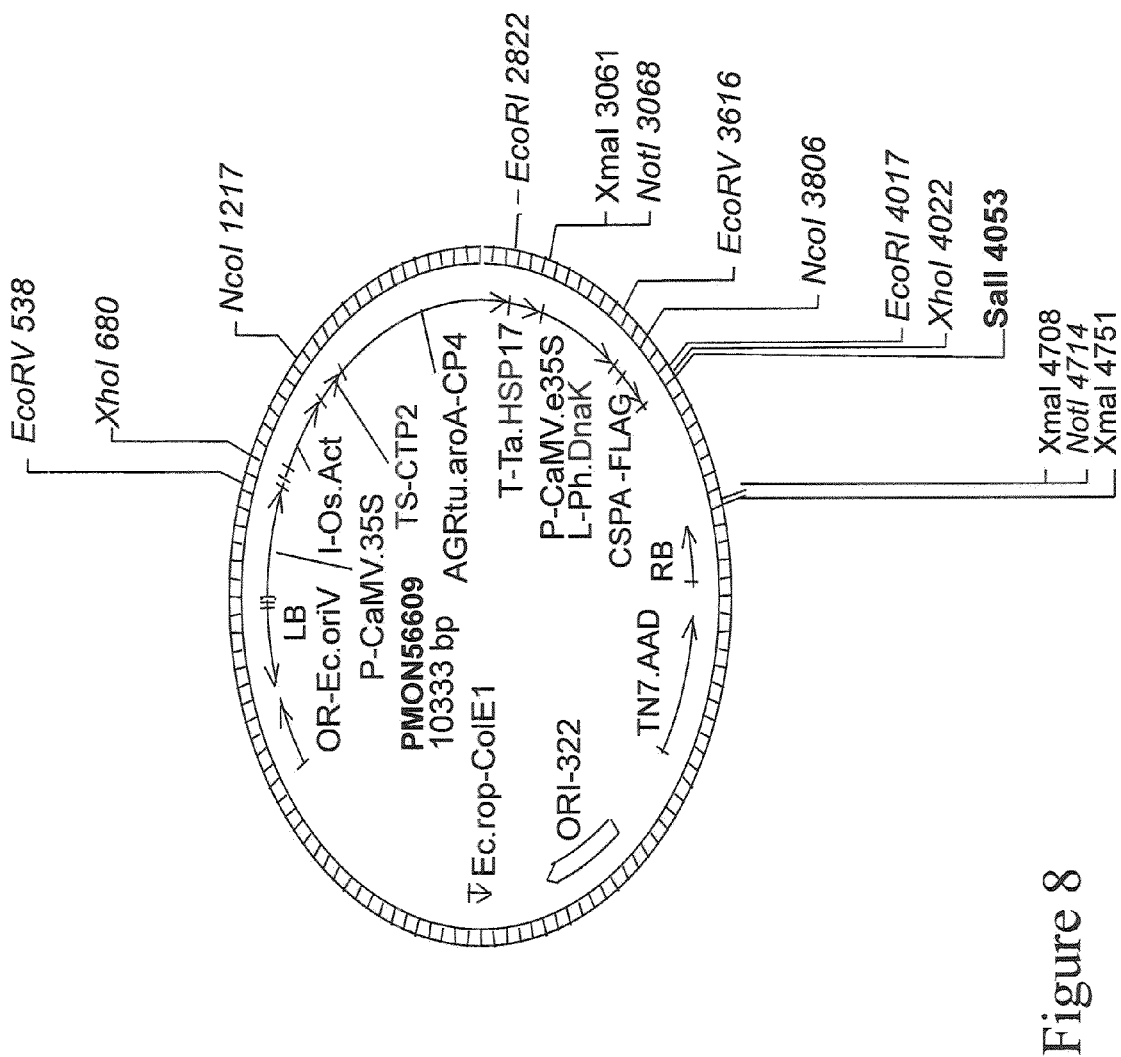
FIG. 8 shows a plasmid map of pMON56609.
Figure 9:
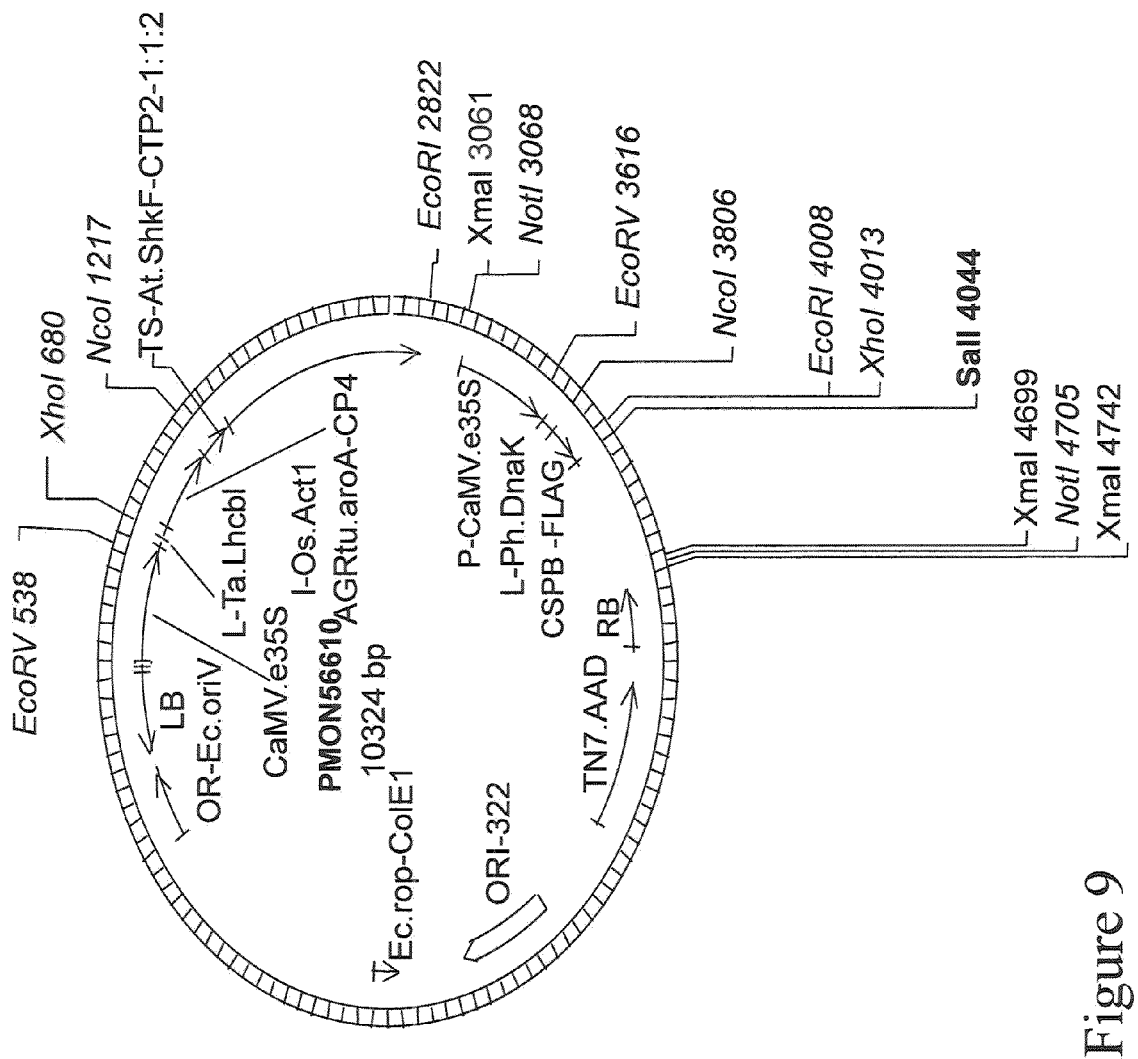
FIG. 9 shows a plasmid map of pMON56610.
Figure 17:
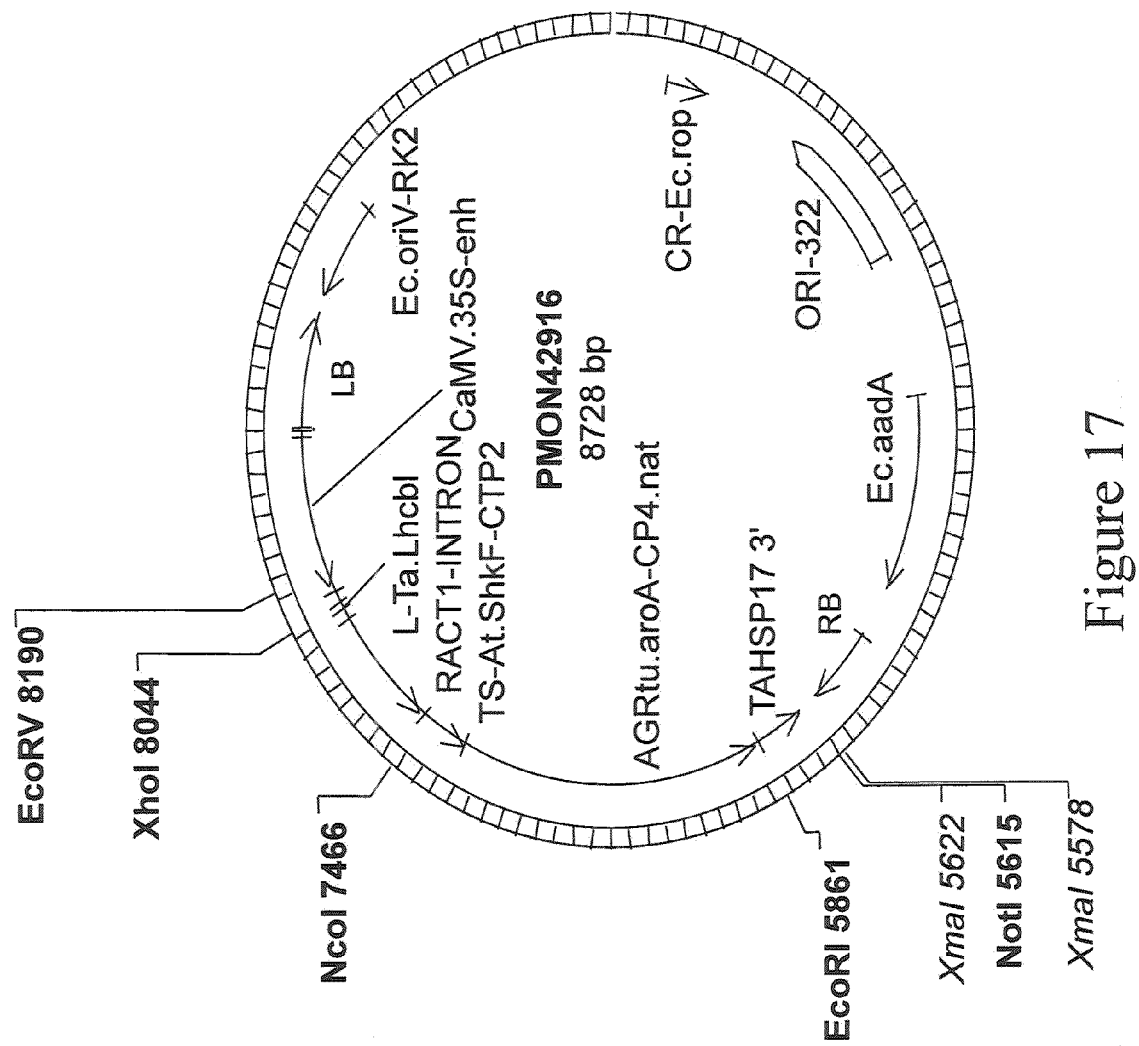
FIG. 17 shows a plasmid map of pMON42916.

PCR products of the CspA and CspB genes were ligated to vector pCR-TOPO 2.1 according to the manufacturer's protocol (Invitrogen, Carlsbad, Calif.). The NcoI/EcoRI fragments of the pCR-TOPO 2.1 derivatives were subcloned into pMON48421 (FIG. 7), linearized by the same restriction enzymes. The NotI fragments of the pMON48421 derivatives encompassing the 35S promoter, Csp genes, and the e9 terminator were subcloned into pMON42916 (FIG. 17) at the NotI site to create pMON56609 (FIG. 8) and pMON56610 (FIG. 9) which contain the CspA and CspB genes, respectively. Said plasmids were transformed into *Agrobacterium tumefaciens* by known methods. pMON56609 is thought to contain a nucleotide sequence encoding a protein similar to SEQ ID NO: 7. pMON56610 is thought to contain a nucleotide sequence encoding a protein similar to SEQ ID NO: 9.

Example 8

*Agrobacterium* Preparation

*Agrobacterium* strain EHA105 is streaked on LB plate containing Kanamycin 50 mg/L and Hygromycin 50 mg/L (denoted LB/KH). Two days prior to co-cultivation, a loop of *Agrobacterium* is transferred to a tube containing 10 ml LB/KH and incubated on a shaker in dark at 28 C for 24 hours. This culture is diluted to 1:100 in 20 ml LB/KH and incubated on a shaker in dark at 28 C overnight. The following day 1 ml of 1:2 dilution of this culture is taken in a cuvette and OD600 is taken with LB/KH as blank. Calculate the volume needed for 5 ml of *agrobacterium* suspension of O.D 1.0 for co-cultivation.

$$\text{Equation:} \frac{(\text{final volume}) * (\text{final } OD600)}{OD600} = $$

Volume needed for final $OD600$ of 1.0

Take the required volume of *agrobacterium* culture in a 40 ml centrifuge tube and spin at 7000 rpm for 7 minutes. Discard the supernatant and dry the pellet. Resuspend the pellet in 5 ml of co-cultivation media (CC MEDIA-MS Basal salts, Sucrose 20 g/L, Glucose 10 g/L, thiamine HCl 0.5 mg/L, L-Proline 115 mg/L, 2,4-D 2 mg/L) with 20 mg/L of acetosyringone.

Transformation of Rice Embryos:

Panicles were harvested from greenhouse grown Nipponbare and Taipai 309 rice varieties. The panicles were sterilized by immersing in 50% commercial bleach for 10 minutes followed by rinsing in sterile distilled water. The panicles were given a 70% alcohol treatment for 3 mins. The seeds were then removed from the panicles and dehusked individually and transferred to a falcon tube containing 0.1% tween 20 solution. The seeds were then treated with 70% alcohol in the laminar air flow chamber. Then the seeds were rinsed with sterile water. This was followed by a 50% bleach treatment for 45 minutes. The seeds were rinsed 5 times in sterile distilled water. Finally the seeds are given 0.1% mercuric chloride treatment for 5 minutes. The seeds were again washed 8 times with sterile distilled water.

The embryos were excised aseptically from the sterile seeds in the laminar flow chamber and placed on solid co-cultivation media (CC MEDIA with 2 g/L phytagel). 50 μL drops of the *agrobacterium* suspension were placed on a sterile petri-plate. 10 embryos were transferred to each drop. The infection was allowed for 15 minutes. The *agrobacterium* suspension was removed with a sterile pipette tip. The infected embryos were transferred to a fresh solid CC MEDIA plate and kept in dark for 2 days. On the third day the embryos were washed with cefotaxime 500 mg/L. The embryos were then dried on sterile filter paper and placed on Delay media (MS Basal salts, Thiamine HCl 1 mg/L, Glutamine 500 mg/L, Magnesium Chloride 750 mg/L, casein hyrolysate 100 mg/L, Sucrose 20 mg/L, 2,4-D 2 mg/L, Pichloram 2.2 mg/L, Cefotaxime 250 mg/L). the embryos are kept on delay medium in dark for a period of 7 days. During this period calli are formed. The calli are transferred to selection media (Delay medium with 50 mg/L Hygromycin) and stored in dark for 10 days. The calli are sub-cultured to fresh selection media after this 10 day period. After another 10 days the calli are transferred to regeneration media (MS Basal salts, sucrose 30 mg/L, Kinetin 2 mg/L, NAA 0.2 mg/L, Cefotaxime 250 mg/L, hygromycin 25 mg/L) and kept in dark for 7 days. The calli are then transferred to fresh regeneration media and moved to a 16-hour photoperiod at 30 C. The shoots developed on this callus are transferred to rooting media (half strength MS Basal salts, sucrose 15 g/L, Cefotaxime 250 mg/L, Hygromycin 25 mg/L). The rooted shoots are transferred to test-tubes containing water and placed in a mist chamber for hardening.

Plants were selected as positive. This could be done, for example, using methods similar to those described in examples 12-14, and 26-29. Including breeding methods described to create the next generation of transgenic plants.

Example 9

Cold Stress Response at Three Leaf Stage

CspB and CspA Rice Transgenic Plants

Plant Material Preparation:

Germination: Seeds were sterilized by treating with 0.01 percent mercuric chloride for 3 minutes and washed thoroughly for ten times in milique water to remove the traces of mercuric chloride. Sterilized seeds were allowed to imbibe by soaking in milique water for 3 hours. The imbibed seeds were germinated on a sterilized moist filter paper at 30° C. temperature and 60% RH using a seed germinator (Serwell Instruments Inc.).

Establishment of three leaf stage seedlings: The three day old germinated seedlings were transferred to portrays (52.5 mm (length)×26 mm (depth)×5.2 mm (diameter)) in the greenhouse having light intensity of 800 micro mol./mt2/sec. and 60% RH. The seedlings were grown till three-leaf stage (Approximately for 12 days) in portrays containing red sandy loam soil. Fertilizer solution was applied to the seedlings once a week till the completion of the experiments (N-75 PPM, P-32 PPM, K-32 PPM, Zn-8 PPM, Mo-2 PPM, Cu-0.04 PPM, B-0.4 PPM and Fe-3.00 PPM).

CspB-R2 Plant Analysis

Protocol: Three leaf stage rice seedlings (12 day old) were subjected to a cold stress of 10° C. for 4 days in presence of 100 micro mol./mt$^2$/sec. light and 70% RH (Percival growth chamber). After the stress treatment the plants were allowed to recover in the greenhouse for 10 days and on the 10$^{th}$ day the growth observations for survived plants and photographic evidences were recorded. Each treatment had 10 replications per line and they were completely randomized.

Results: Among eight different lines tested for cold stress tolerance six lines exhibited significantly higher cold tolerance compared to the wild type. The lines including R2-226-6-9-3, R2-226-29-1-1, R2-257-20-2-1, R2-238-1-1-3, R2-230-4-4-2 and R2-257-3-1-3 showed high cold tolerance by exhibiting high recovery growth and less percent reduction in growth (over non-stressed control) compared to the wild type (table-1, plate-1). The line R2-230-4-42, has performed extremely well, it exhibited 100 percent survival and maintained good growth during recovery (Table 1).

TABLE 1

Three leaf stage cold stress recovery growth observations of CspB R2 transgenic lines.

| Lines | % Survival at end of recovery | Plant height (cm) Stressed | Plant height (cm) Non-stressed | % Reduction in plant height over non-stressed |
|---|---|---|---|---|
| R2-257-17-1-1 | 13 | 21.5 ± 11 | 43.44 ± 4.09 | 50.38 |
| R2-230-34-1-2 | 53 | 20.78 ± 6.3 | 45.0 ± 3.51 | 53.82 |
| R2-226-6-9-3 | 60 | 27.5 ± 7 | 33.74 ± 4.65 | 18.49 |
| R2-226-29-1-1 | 53 | 27.6 ± 10.7 | 35.22 ± 4.06 | 21.63 |
| R2-257-20-2-1 | 93 | 32.39 ± 5.48 | 44.0 ± 2.95 | 27.27 |
| R2-238-1-1-3 | 80 | 29.25 ± 8.19 | 40.72 ± 5.8 | 25 |
| R2-230-4-4-2 | 100 | 33.95 ± 4.10 | 45 ± 3.98 | 24 |
| R2-257-3-1-3 | 40 | 29.80 ± 2.66 | 42 ± 4.11 | 28.5 |
| WT-Taipei | 26 | 23.93 ± 5.61 | 45.0 ± 3.7 | 46.6 |

(Index: WT = Wild type)

CspB-R3 Plant Analysis

Protocol: Three leaf stage seedlings were exposed to cold stress of 8 degree Celsius for 1 day in presence of 1000 micro mol./mt2/sec. of light. Later the seedlings were allowed to recover at 28 degree Celsius in the greenhouse for 15 days and at the end of recovery the plant height was recorded.

Results: Eight different lines tested for cold stress tolerance and all the eight lines showed improved tolerance compared to wild type (non-transgenic) plants. These results confirmed the R2 analysis data showing improved cold tolerance (Table 2).

TABLE 2

Three leaf stage cold stress recovery growth observations of CspB R3 transgenic lines.

| Lines | Stressed-plant height (cm) at end of recovery | Non-stressed plant height (cm) at end of recovery | Percent reduction in plant height over non-stress |
|---|---|---|---|
| R3-226-6-9-3 | 28.8 ± 2.88 | 29.34 ± 7.20 | 1.84 |
| R3-226-29-1-3-4 | 30.18 ± 3.19 | 32.07 ± 3.79 | 5.89 |
| R3-230-4-4-2-1 | 30.42 ± 2.16 | 35.09 ± 4.19 | 13.30 |
| R3-230-34-1-2-1 | 32.14 ± 3.41 | 37.4 ± 5.68 | 14.01 |
| R3-238-1-1-3-4 | 29.54 ± 3.61 | 32.2 ± 3.56 | 8.26 |
| R3-257-3-1-3-1 | 27.12 ± 3.38 | 30.86 ± 3.82 | 12.11 |
| R3-257-15-1-1-2 | 23.84 ± 2.85 | 26.71 ± 1.92 | 10.74 |
| R3-257-20-2-1-1 | 33.8 ± 3.48 | 38.82 ± 1.97 | 12.93 |
| WT-Taipei | 23.9 ± 3.74 | 36.65 ± 4.01 | 34.78 |

CspA-R2 Plant Analysis

Protocol: Three leaf stage rice seedlings (12 day old) were subjected to a cold stress of 10° C. for 3 days in presence of 1000 micro mol./mt2/sec. and 70% RH in a growth chamber. After the stress treatment the plants were allowed to recover in the green house for 15 days and on the 15$^{th}$ day the growth observations were recorded. Each value is an average of 12 observations and the experiment was conducted by following completely randomized (CRD) experimental design.

Results: Out of seven independent CspA transgenic lines tested 6 lines showed improved cold tolerance compared to wild type. In this experiment plant height was reduced to close to 50% in cold treated control plants (WT) compared to non-stressed plants. Where as in transgenic plants with CspA gene reduction in plant height upon cold treatment varied 4.5% to 22.50% among different independent lines (except one line where reduction in growth was 47.09%). These results suggest that CspA improves the cold tolerance of rice (Table 3).

TABLE 3

Three leaf stage cold stress recovery growth observations of CspA R2 transgenic rice lines.

| Lines | Plant height at the end of recovery (cm) Stressed | Plant height at the end of recovery (cm) Non-stressed | Percent reduction in plant height over non-stressed |
|---|---|---|---|
| R2-362-3-1-2 | 28.75 ± 3.11 | 30.08 ± 2.9 | 4.5 |
| R2-328-2-1-1 | 29.5 ± 2.92 | 35.58 ± 3.12 | 17.08 |
| R2-362-7-1-2 | 15.83 ± 2.92 | 29.92 ± 1.73 | 47.09 |
| R2-365-4-5-3 | 26.08 ± 3.75 | 32.08 ± 2.27 | 18.7 |
| R2-362-6-1-6 | 27.17 ± 2.25 | 32.00 ± 1.76 | 15.05 |
| R2-362-3-1-10 | 29.58 ± 3.50 | 38.17 ± 2.59 | 22.50 |
| R2-362-7-1-2 | 24.58 ± 3.42 | 27.25 ± 2.01 | 9.79 |
| WT-Nipponbare | 20.58 ± 1.73 | 37.92 ± 8.59 | 46.05 |

CspA-R3 Plant Analysis

Experiment I

Protocol: Three leaf stage seedlings were exposed to cold stress of 10 degree Celsius for 3 days in presence of 1000 micro mol. of light. Later the seedlings were allowed to recover at 28 degree Celsius in the greenhouse for 30 days and at the end of recovery the plant height and percent seedling survival were recorded. (In this experiment 8 replications were used for each transgenic line and 10 replications were used for wild type.)

Results: The six transgenic lines subjected to cold stress performed better under cold stress than wild type. These results further confirmed the R2 analysis data by showing improved cold tolerance (Table 4).

TABLE 4

Three leaf stage cold stress recovery growth observations of CspA R3 transgenic rice lines.

| Lines | Stressed-plant height (cm) at the end of recovery | Non-stressed plant height (cm) at the end of recovery | Percent reduction in plant height over non-stress | Percent seedling Survival |
|---|---|---|---|---|
| R3-362-3-1-2-2 | 25.5 ± 4.46 | 32.25 ± 5.03 | 20.93 | 100 |
| R3-362-3-1-3-2 | 25.62 ± 3.36 | 34.43 ± 6.24 | 25.58 | 66 |
| R3-365-10-1-2-3 | 27.35 ± 3.24 | 33.75 ± 4.58 | 18.96 | 100 |
| R3-362-6-1-2-1 | 28 ± 2.45 | 34.45 ± 2.29 | 18.72 | 100 |

TABLE 4-continued

Three leaf stage cold stress recovery growth observations of CspA R3 transgenic rice lines.

| Lines | Stressed-plant height (cm) at the end of recovery | Non-stressed plant height (cm) at the end of recovery | Percent reduction in plant height over non-stress | Percent seedling Survival |
|---|---|---|---|---|
| R3-362-7-1-2-3 | 27.5 ± 24.17 | 29.94 ± 5.03 | 8.1 | 100 |
| R3-362-7-1-3-3 | 27.88 ± 4.22 | 31.92 ± 2.89 | 12.65 | 100 |
| WT-Nipponbare | 26.25 ± 3.95 | 36.34 ± 4.06 | 27.76 | 40 |

Note:
Plant height was recorded only for survived plants and their averages are given above.

Experiment II

Protocol: Three leaf stage seedlings were exposed to cold stress of 10 degree Celsius for 1 day in presence of 1000 micro mol. of light. Later the seedlings were allowed to recover at 28 degree Celsius in the green house for 30 days and at the end of recovery the plant height and percent seedling survival were recorded.

Results: The five transgenic lines subjected to cold stress performed better under cold stress than wild type. These results further confirmed the R2 analysis data by showing improved cold tolerance (Table 5).

TABLE 5

Three leaf stage cold stress recovery growth observations of CspA R3 transgenic rice lines.

| Lines | Stressed-plant height (cm) at end of recovery | Non-stressed plant height (cm) at end of recovery | Percent reduction in plant height over non-stress |
|---|---|---|---|
| R3-362-3-1-2-2 | 32.76 ± 3.49 | 32.25 ± 5.03 | Nil |
| R3-362-3-1-3-2 | 36.11 ± 2.04 | 34.43 ± 6.24 | Nil |
| R3-365-10-1-2-3 | 35.85 ± 2.94 | 33.75 ± 4.58 | Nil |
| R3-362-6-1-2-1 | 21.54 ± 5.84 | 34.45 ± 2.29 | 37.4 |
| R3-362-7-1-2-3 | 32.55 ± 2.73 | 29.94 ± 5.03 | Nil |
| R3-362-7-1-3-3 | 32.17 ± 3.27 | 31.92 ± 2.89 | Nil |
| WT-Nipponbare | 31.92 ± 2.66 | 36.34 ± 4.06 | 12.16 |

Heat Stress Response at Three Leaf Stage

Plant Material Preparation:

Germination: Seeds were sterilized by treating with 0.01 percent mercuric chloride for 3 minutes and washed thoroughly (~ten times in deionized water) to remove the traces of mercuric chloride. Sterilized seeds were allowed to imbibe by soaking in milique water for 3 hours. The imbibed seeds were germinated on a sterilized moist filter paper at 30° C. temperature and 60% RH using a seed germinator (Serwell Instruments Inc.).

Establishment of three leaf stage seedlings: The three day old germinated seedlings were transferred to portrays (52.5 mm (length)×26 mm (depth)×5.2 mm (diameter)) in the green house having light intensity of 800 micro mol./mt2/sec. and 60% RH. The seedlings were grown till three-leaf stage (Approximately for 12 days) in portrays containing red soil. Fertilizer solution was sprayed to the seedlings once a week till the completion of the experiments (N-75 PPM, P-32 PPM, K-32 PPM, Zn-8 PPM, Mo-2 PPM, Cu-0.04 PPM, B-0.4 PPM and Fe-3.00 PPM).

CspA-R2 Plant Analysis

Protocol: Three leaf stage rice seedlings (12 day old) were subjected to the heat stress of 50° C. for 3 hours in presence of 70% RH. After the stress treatment the plants were allowed to recover in the green house for 15 days and on the 15$^{th}$ day the growth observations were recorded. Each value is an average of 12 observations.

Results: Out of seven independent CspA transgenic lines tested 6 lines showed improved heat tolerance compared to wild type. In this experiment plant height was reduced by more than 50% in heat-treated control plants (WT) compared to no stressed plants. Where as in transgenic plants with CspA gene reduction in plant height upon heat treatment varied from 9.5% to 35% among different independent lines. These results suggest that CspA improves the heat tolerance of rice (Table 6).

TABLE 6

Three leaf stage plant heat stress recovery growth observations of CspA R2 transgenic rice lines.

| Lines | Plant height at the end of recovery (cm) | | Percent reduction in plant height over non-stressed |
|---|---|---|---|
| | Stressed | Non-stressed | |
| R2-362-3-1-2 | 26.67 ± 4.97 | 30.08 ± 2.9 | 11.33 |
| R2-328-2-1-1 | 26.17 ± 3.49 | 35.58 ± 3.12 | 26.41 |
| R2-362-7-1-2 | 25.17 ± 1.94 | 29.92 ± 1.73 | 15.87 |
| R2-365-4-5-3 | 20.83 ± 1.17 | 32.08 ± 2.27 | 35.06 |
| R2-362-6-1-6 | 23.17 ± 1.83 | 32.00 ± 1.76 | 27.59 |
| R2-362-3-1-10 | 29.33 ± 5.01 | 38.17 ± 2.59 | 23.15 |
| R2-362-7-1-2 | 24.67 ± 2.8 | 27.25 ± 2.01 | 9.4 |
| WT-Nipponbare | 18.5 3.51 | 37.92 ± 8.59 | 51.21 |

CspB-R3 Plant Analysis

Protocol: Three-leaf stage seedlings were exposed to high temperature stress of 53 degree Celsius for 2 hours and later the seedlings were allowed to recover at 28 degree Celsius in the greenhouse for 15 days and at the end of recovery the plant height was recorded.

Results: Out of eight transgenic lines tested seven lines performed better under heat stress tested compared to wild type. These results suggest that CspB improves heat tolerance of rice (Table 7).

TABLE 7

Three leaf stage plant heat stress recovery growth observations of CspB R3 transgenic rice lines.

| Lines | Stressed-plant height (cm) at end of recovery | Non-stressed plant height (cm) at end of recovery | Percent reduction in plant height over non-stress |
|---|---|---|---|
| R3-226-6-9-3 | 34.53 ± 2.14 | 35.54 ± 2.07 | 2.84 |
| R3-226-29-1-3-4 | 32.38 ± 1.47 | 37.06 ± 2.92 | 12.62 |

TABLE 7-continued

Three leaf stage plant heat stress recovery growth observations of CspB R3 transgenic rice lines.

| Lines | Stressed-plant height (cm) at end of recovery | Non-stressed plant height (cm) at end of recovery | Percent reduction in plant height over non-stress |
|---|---|---|---|
| R3-230-4-4-2-1 | 28.78 ± 4.16 | 35.06 ± 2.07 | 17.41 |
| R3-230-34-1-2-1 | 33.3 ± 3.94 | 37.6 ± 3.05 | 11.43 |
| R3-238-1-1-3-4 | 33.96 ± 2.06 | 41.2 ± 3.83 | 17.57 |
| R3-257-3-1-3-1 | 33.76 ± 3.74 | 35.4 ± 2.07 | 4.63 |
| R3-257-15-1-1-2 | 25.68 ± 4.27 | 38.2 ± 3.11 | 32.77 |
| R3-257-20-2-1-1 | 34.78 ± 1.7 | 42.2 ± 2.97 | 17.5 |
| WT-Taipei | 25.5 ± 2.97 | 36.65 ± 4.8 | 30.42 |

CspA-R3 Plant Analysis

Experiment I

Protocol: Three-leaf stage seedlings were exposed to high temperature stress of 53 degree Celsius for 3 hours and later the seedlings were allowed to recover at 28 degree Celsius in the greenhouse for 30 days and at the end of recovery the plant height was recorded.

Results: These results confirmed the R2 analysis data by showing improved heat tolerance (Table 8).

TABLE 8

Three leaf stage plant heat stress recovery growth observations of CspA R3 transgenic rice lines.

| Lines | Stressed - plant height (cm) at end of recovery | Non-stressed plant height (cm) at end of recovery | Percent reduction in plant height over non-stress |
|---|---|---|---|
| R3-362-3-1-2-2 | 31.07 ± 7.01 | 32.25 ± 5.03 | 3.6 |
| R3-362-3-1-3-2 | 30.28 ± 4.74 | 34.43 ± 6.24 | 12.05 |
| R3-365-10-1-2-3 | 24.23 ± 7.60 | 33.75 ± 4.58 | 28.20 |
| R3-362-6-1-2-1 | 26.93 ± 2.97 | 34.45 ± 2.29 | 21.82 |
| R3-362-7-1-2-3 | 29.52 ± 2.61 | 29.94 ± 5.03 | 1.40 |
| R3-362-7-1-3-3 | 21.30 ± 6.37 | 31.92 ± 2.89 | 33.27 |
| WT-Nipponbare | 22.68 ± 2.96 | 36.34 ± 4.06 | 37.58 |

Experiment II

Protocol: Three leaf stage seedlings were exposed to high temperature stress of 50 degree Celsius for 1 hour in the presence of 1000 micro mol. of light and later the seedlings were allowed to recover at 28 degree Celsius in the greenhouse for 30 days and at the end of recovery the plant height was recorded.

Results: These results confirmed the R2 analysis data by showing improved heat tolerance (Table 9).

TABLE 9

Three leaf stage plant heat stress recovery growth observations of CspA R3 transgenic rice lines.

| Lines | Stressed - plant height (cm) at end of recovery | Non-stressed plant height (cm) at end of recovery | Percent reduction in plant height over non-stress |
|---|---|---|---|
| R3-362-3-1-2-2 | 31.57 ± 2.39 | 32.25 ± 5.03 | 2.10 |
| R3-362-3-1-3-2 | 34.20 ± 3.87 | 34.43 ± 6.24 | 0.6 |
| R3-365-10-1-2-3 | 31.63 ± 4.32 | 33.75 ± 4.58 | 6.28 |
| R3-362-6-1-2-1 | 19.72 ± 6.76 | 34.45 ± 2.29 | 42.75 |
| R3-362-7-1-2-3 | 32.18 ± 3.25 | 29.94 ± 5.03 | Nil |
| R3-362-7-1-3-3 | 32.80 ± 1.51 | 31.92 ± 2.89 | Nil |
| WT-Nipponbare | 28.20 ± 2.79 | 36.34 ± 4.06 | 22.39 |

Water Stress Response

Plant Material Preparation:

Germination: Seeds were sterilized by treating with 0.01 percent mercuric chloride for 3 min later washed thoroughly for ten times in milique water to remove the traces of mercuric chloride. Sterilized seeds were allowed to imbibe by soaking in milique water for 3 hours. The imbibed seeds were germinated on a sterilized moist filter paper at 30° C. temperature and 60% RH using a seed germinator (Serwell Instruments Inc.).

CspB-R2 Plant Analysis

Experimental Protocol

The germinated seedlings (3 day old) were transferred to two different levels of water stress, created in PVC pots containing vermiculite, which is measured in terms of field capacity (FC). The FC-100% is a saturated condition (i.e. 100 g vermiculite requires 350 ml of water) (Sharp et. al., 1988, Plant physiol. 87: 50-57). The different levels of water stress (i.e. 50% FC and 25% FC) were created in a PVC pots containing vermiculite by adding required amount of water. The water status in different stress levels was constantly maintained, by adding each day the amount of water lost due to evapotranspiration, through out the experiment. The seedlings were allowed to grow for 15 days in the water stress condition in the greenhouse in presence of 800 micro mol./mt2/sec. light intensity and 60% RH. At $15^{th}$ day the growth of root and shoot were recorded and photographs were taken. Each treatment had 10 replications per line and they were completely randomized.

The percent reduction in growth was computed by adopting following formula.

$$\% \text{ reduction over absolute control} = \frac{\text{Growth of root/shoot of absolute control} - \text{Growth of root/shoot of } FC\text{-}25\%}{\text{Growth of root/shoot of absolute control}}$$

Results: Four different CspB transgenic lines were analyzed for water stress tolerance. All the CspB transgenic lines tested exhibited significantly higher growth during stress compared to the wild type plants. The transgenic lines including R2-257-15-1-1, R2-238-1-1-3, R2-257-3-1-6 and R2-226-6-9-3 exhibited least percent reduction in root and shoot growth over non-stress control (FC-100%). The reduction in root and shoot growth in these lines ranged between 11 to 25%. Where as, the wild type plants exhibited maximum reduction in growth, which is close to 50%. These results suggest that CspA improves the water stress tolerance of rice (Table-10 and Table-11).

TABLE 10

Comparison of root and shoot growth at the end of water stress of cspB transgenic lines and the wild type.

| | FC-100% | | | FC-50% | | | FC-25% | | |
|---|---|---|---|---|---|---|---|---|---|
| Lines | Root | Shoot | R:S | Root | Shoot | R:S | Root | Shoot | R:S |
| R2-257-15-1-1 | 9.2 ± 2.2 | 24.3 ± 2 | .37 | 9 ± 1.27 | 23.7 ± 1.5 | .37 | 8.1 ± 1.5 | 18.5 ± 2.2 | .43 |
| R2-238-1-1-3 | 9.65 ± 2.7 | 26.3 ± 13.8 | .36 | 8.35 ± 1.56 | 22.9 ± 1.26 | .36 | 7.15 ± 1.0 | 18.1 ± 1.6 | .39 |
| R2-257-3-1-6 | 7.35 ± 2.2 | 26.1 ± 1.31 | .28 | 6.4 ± 1.15 | 23.0 ± 1.57 | .27 | 6.9 ± 1.07 | 19.5 ± 1.96 | .35 |
| R2-226-6-9-3 | 8.95 ± 1.82 | 25.05 ± 1.6 | .35 | 7.4 ± 1.2 | 19.0 ± 2.24 | .38 | 7.25 ± 1.5 | 17.4 ± 2.15 | .41 |
| WT-Taipei | 9.2 ± 1.62 | 24.6 ± 1.58 | .37 | 7.4 ± 1.66 | 22.4 ± 0.97 | .33 | 6.58 ± 0.9 | 12.8 ± 3.2 | .51 |

(Index: WT = wild type, R:S = Root to Shoot ratio)

TABLE 11

Comparison of percent reduction in growth of root and shoot of cspB transgenic lines and the wild type.

| Lines | % Reduction in root growth | % Reduction in shoot growth | % Reduction in root and shoot growth |
|---|---|---|---|
| R2-257-15-1-1 | 11 | 23.8 | 20 |
| R2-238-1-1-3 | 25 | 31 | 30 |
| R2-257-3-1-6 | 6 | 25.2 | 21 |
| R2-226-6-9-3 | 19 | 30.5 | 27.5 |
| WT-Taipei | 28.4 | 47.9 | 42.8 |

TABLE 12

Water stress response of CspA R2 transgenic rice lines.

| Lines | Percentage plants showing wilting |
|---|---|
| R2-362-3-1-2 | 17 |
| R2-328-2-1-1 | 43 |
| R2-362-7-1-2 | 85 |
| R2-365-4-5-3 | 5 |
| R2-362-6-1-6 | Nil |
| R2-362-3-1-10 | 15 |
| R2-362-7-1-2 | 8 |
| WT-Nipponbare | 66 |

CspA-R2 Plant Analysis a. Plant Material Preparation:

Germination: Seeds were sterilized by treating with 0.01 percent mercuric chloride for 3 minutes and washed thoroughly for ten times in milique water to remove the traces of mercuric chloride. Sterilized seeds were allowed to imbibe by soaking in milique water for 3 hours. The imbibed seeds were germinated on a sterilized moist filter paper at 30° C. temperature and 60% RH using a seed germinator (Serwell Instruments Inc.).

Establishment of three leaf stage seedlings: The three day old germinated seedlings were transferred to portrays (52.5 mm (length)×26 mm (depth)×5.2 mm (diameter)) in the green house having light intensity of 800 micro mol./mt2/sec. and 60% RH. The seedlings were grown till three-leaf stage (Approximately for 12 days) in portrays containing red sandy loam soil. Fertilizer solution was sprayed to the seedlings once a week till the completion of the experiments (N-75 PPM, P-32 PPM, K-32 PPM, Zn-8 PPM, Mo-2 PPM, Cu-0.04 PPM, B-0.4 PPM and Fe-3.00 PPM).

Protocol: One-month-old seedlings were subjected to water stress for three days in presence of 800 micro mol./mt2/sec. light and 60% RH in the greenhouse. Water stress was imposed by withholding irrigation. At the end of three days, plants started showing the wilting symptom. The stress was alleviated by irrigating the plants with water and 24 hours later the observations on percent plants showing wilting symptoms were recorded. A minimum of 12 plants was maintained per line per treatment.

Results: Out of seven independent CspA transgenic lines tested 6 lines showed improved water stress tolerance compared to wild type. Sixty six percent of control plants did not recover from wilting after irrigation where as in CspA transgenic plants percentage of plants showing wilting symptoms after irrigation varied from 5% to 43% among different independent lines (except one line where percentage of plants showing wilting was 85%). These results suggest that CspA improves the water stress tolerance in rice (Table 12).

Salt Stress Response

CspB-R3 Plant Analysis

Protocol: Germinated seedlings (48 h. old) were subjected to salinity stress by transferring them to PVC pots with vermiculite containing 200 mM of NaCl and grown for 10 days. After 10 days of stress the seedlings were allowed to recover for 15 days by transferring them to a fresh trays of vermiculite containing water. The growth observation such as plant height was recorded at the end of recovery. This experiment was conducted in the greenhouse by following Completely Randomized Design (CRD) and maintained eight replications per treatment.

Results: Seven CspB transgenic lines and wild type plants were subjected to 200 mM NaCl stress. Under this condition five transgenic lines performed better compared to wild type. These results suggest that CspB improves tolerance of rice plants to salt stress (Table 13).

TABLE 13

Salt stress recovery growth observations of CspA R2 transgenic rice lines.

| Lines | Stressed-plant height (cm) at end of recovery | Non-stressed plant height (cm) at end of recovery | Percent reduction in plant height over non-stressed |
|---|---|---|---|
| R3-226-6-9-3 | 12.68 ± 2.83 | 23.48 ± 3.85 | 45.99 |
| R3-226-29-1-3-4 | 19.24 ± 3.46 | 25.54 ± 3.64 | 24.66 |
| R3-230-4-4-2-1 | 15.39 ± 3.05 | 25.2 ± 2.14 | 38.92 |
| R3-230-34-1-2-1 | 15.78 ± 3.31 | 23.26 ± 1.98 | 32.15 |
| R3-238-1-1-3-4 | 13.41 ± 2.73 | 23.63 ± 4.61 | 43.25 |
| R3-257-3-1-3-1 | 21.07 ± 3.28 | 28.95 ± 4.37 | 27.64 |
| R3-257-20-2-1-1 | 19.01 ± 3.98 | 26.35 ± 2.84 | 27.85 |
| WT-Taipei | 14.71 ± 2.28 | 27.43 ± 2.75 | 46.37 |

R3 water stress assay

Germinated seedlings (3 day old) from four independent transgenic lines (1, 2, 3, 4) of cspA and wild type (Nipponbare—Number. 5) were subjected to water stress by transferring them into a pot containing vermiculite. Three levels of water regimes were maintained, they are 100% field capacity (FC-100=3.72 ml of water/g vermiculite)

25% field capacity (FC25=0.93 ml of water/g vermiculite) 15% field capacity (FC 15=0.558 ml/g vermiculite). The seedlings were grown in different water regimes for 30 days in presence of 800 micro mol./mt2/sec. light intensity and 60% RH in the greenhouse. The water status in different stress levels was constantly maintained, by adding each day the amount of water lost due to vapotranspiration, throughout the experiment. At the end of 30th day plants were allowed to recover by adding water to bring it the level of FC 100 and maintained for 15 days. During the experiment the growth observations such as plant height (pl. ht.) at the end of stress (ES) and root (R) shoot (S) length and dry weight at the end of the recovery were recorded.

Each treatment had 10 replications per line and they were completely randomized.

TABLE 14

Average shoot and root length (cm) at the end of recovery

| Line code | Lines | FC100_Root | FC100_Shoot | FC25_Root | FC25_Shoot | FC15_Root | FC15_Shoot |
|---|---|---|---|---|---|---|---|
| 1 | R2-362-3-1-3-4 | 24.5 ± 1.9 | 49.1 ± 3.6 | 17.0 ± 2.6 | 34.5 ± 2.4 | 12.5 ± 1.4 | 31.2 ± 1.8 |
| 2 | R2-362-6-1-2-2 | 23.3 ± 1.3 | 45.6 ± 1.5 | 17.5 ± 1.8 | 31.5 ± 1.5 | 17.6 ± 2.3 | 32.0 ± 0.7 |
| 3 | R2-362-7-1-3-3 | 24.5 ± 1.3 | 47.6 ± 3.3 | 17.8 ± 2.0 | 33.5 ± 1.7 | 15.9 ± 1.7 | 31.9 ± 1.7 |
| 4 | R2-365-10-1-2-1 | 24.03 ± 1.5 | 44.4 ± 2.2 | 13.8 ± 1.3 | 30.24 ± 1.1 | 13.9 ± 1.3 | 28.9 ± 0.9 |
| 5 | WT-Nipponbare | 23.84 ± 1.25 | 44.8 ± 2.0 | 12.9 ± 1.8 | 31.6 ± 1.2 | 13.9 ± 1.9 | 31.5 ± 1.2 |

TABLE 15

Average shoot and root dry weight (mg) at the end of recovery

| Line code | Lines | FC100_Root | FC100_Shoot | FC25_Root | FC25_Shoot | FC15_Root | FC15_Shoot |
|---|---|---|---|---|---|---|---|
| 1 | R2-362-3-1-3-4 | 231 ± 21.8 | 563.9 ± 60.7 | 57.6 ± 6.8 | 189 ± 16.3 | 447 ± 6.3 | 152.9 ± 22.1 |
| 2 | R2-362-6-1-2-2 | 226 ± 14.2 | 531.8 ± 63 | 72 1 ± 5.1 | 179.8 ± 17 | 539 ± 7.9 | 146.3 ± 21.1 |
| 3 | R2-362-7-1-3-3 | 229.5 ± 30.2 | 533 ± 48.5 | 66.1 ± 11.9 | 183 ± 13.9 | 606 ± 5.7 | 147.4 ± 14.7 |
| 4 | R2-365-10-1-2-1 | 219 ± 43.5 | 557 ± 71.9 | 56.2 ± 9.3 | 1739 ± 27.3 | 47.3 ± 3.1 | 133.7 ± 7.7 |
| 5 | WT-Nipponbare | 226 ± 34.5 | 525 ± 31.3 | 61.1 ± 4.2 | 151.1 ± 16.8 | 452 ± 7.5 | 132.2 ± 11.03 |

TABLE 16

Average shoot length (cm) at the end of stress

| Line code | Lines | FC100 | FC25 | FC15 |
|---|---|---|---|---|
| 1 | R2-362-3-1-3-4 | 42 ± 4.6 | 28.4 ± 1.7 | 27.4 ± 2.1 |
| 2 | R2-362-6-1-2-2 | 40.4 ± 2.1 | 26.1 ± 1.1 | 25.2 ± 2.2 |
| 3 | R2-362-7-1-3-3 | 40.1 ± 2.7 | 27 ± 2.0 | 26.3 ± 1.4 |
| 4 | R2-365-10-1-2-1 | 38.9 ± 2.3 | 26.3 ± 1.6 | 23.3 ± 2.4 |
| 5 | WT-Nipponbare | 39.5 ± 1.05 | 24.2 ± 2.0 | 24.7 ± 1.9 |

Example 10 cspA

Figure 10:
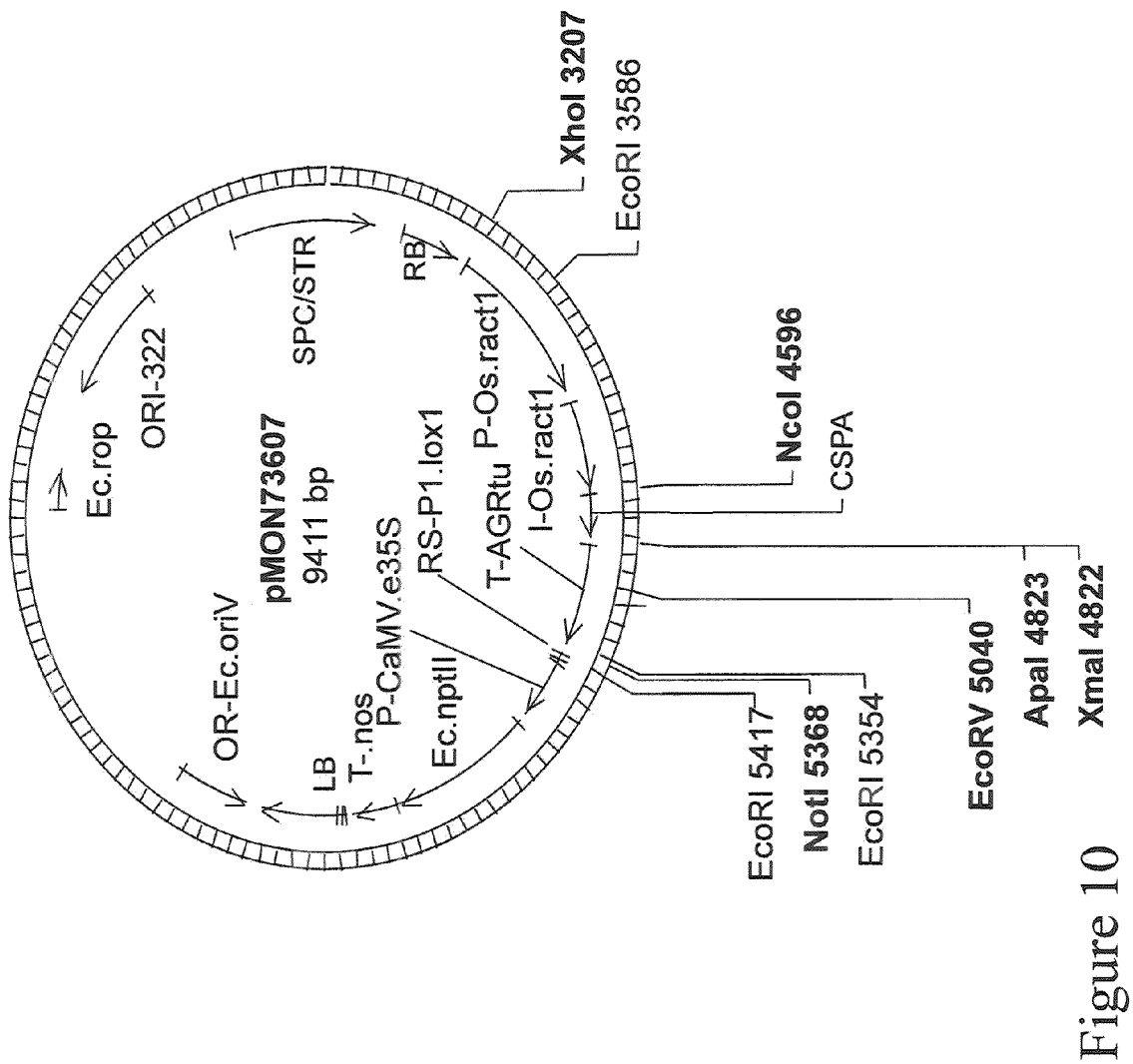
FIG. 10 shows a plasmid map of pMON73607.

Construction of pMON73607 (FIG. 10)

1. Vector pMON61322 cut with NcoI and ApaI to open up backbone and drop out Csp A gene. Backbone fragment isolated by gel purification.

2. *E. coli* cspA gene PCR amplified from pMON56609 (FIG. 8) vector. PCR primers used left the NcoI site at the 5' end of the gene and created a SwaI and an ApaI site at the 3' end.

Figure 11:
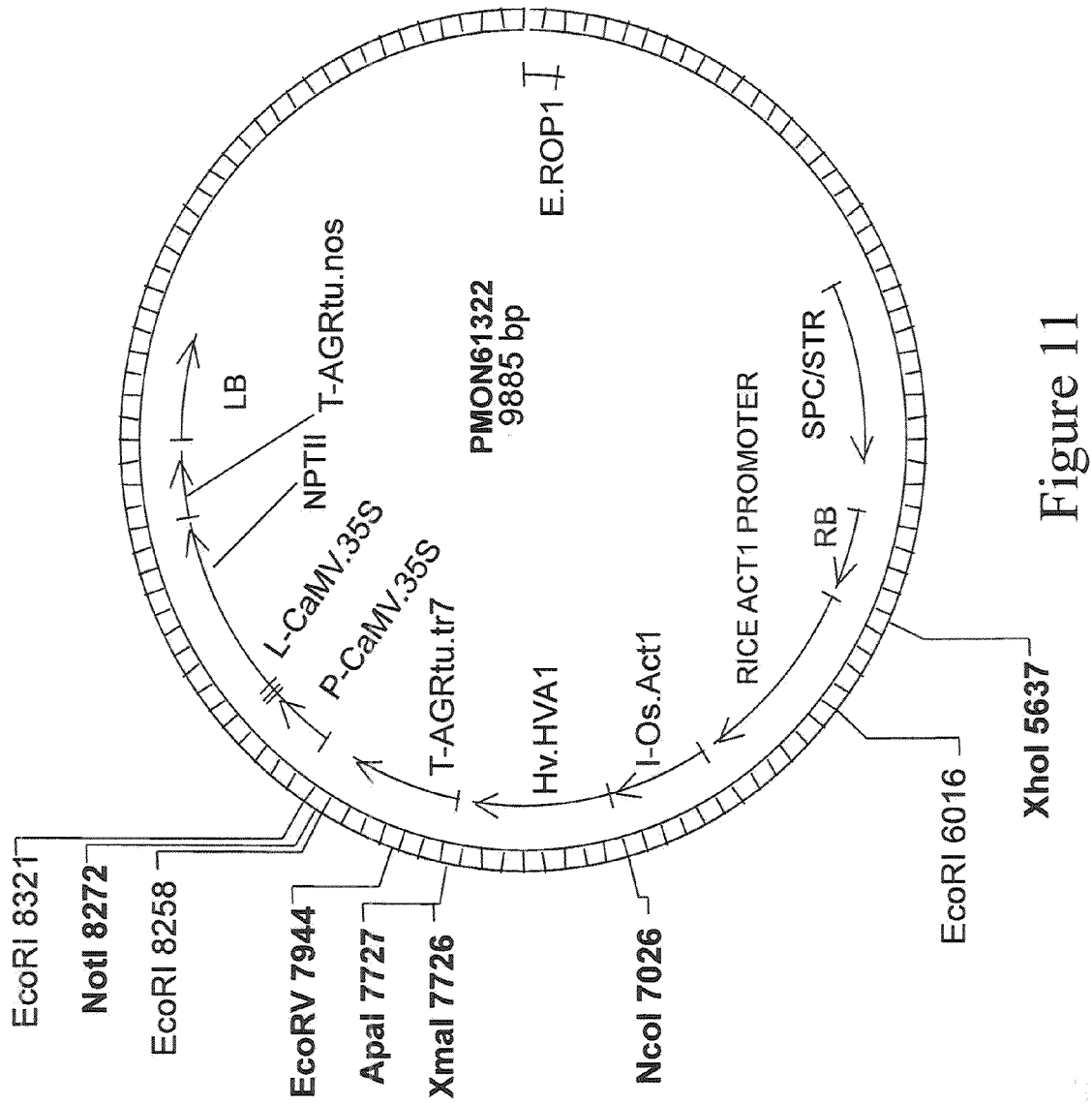
FIG. 11 shows a plasmid map of pMON61322.

3. Ligated PCR fragment and pMON61322 (FIG. 11) backbone. Transformed into library efficiency DH5α cells. Screened colonies using ApaI and NcoI to identify clones with inserts.

4. Sequenced vector to confirm fidelity of the cspA gene and other selected regions of the plasmid.

cspB

Figure 12:
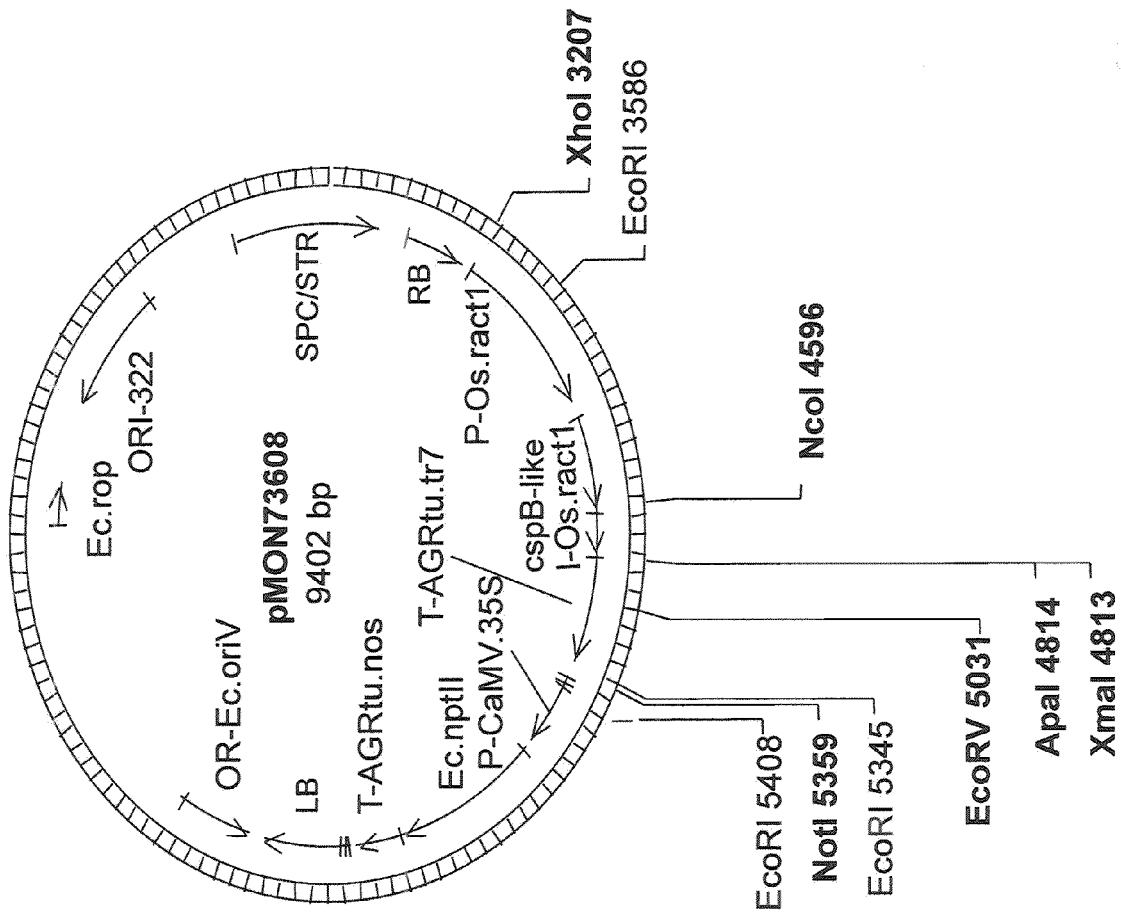
FIG. 12 shows a plasmid map of pMON73608.

Construction of pMON73608 (FIG. 12)

1. Vector pMON61322 cut with NcoI and ApaI to open up backbone and drop out HVA1 gene. Backbone fragment isolated by gel purification.

2. *Bacillus subtilis* cspB gene PCR amplified from pMON56610 vector. PCR primers used left the NcoI site at the 5' end of the gene and created a SwaI and an ApaI site at the 3' end.

3. Ligated PCR fragment and pMON61322 backbone. Transformed into library efficiency DH5α cells. Screened colonies using ApaI and NcoI to identify clones with inserts.

4. Sequenced vector to confirm CspB gene and other selected regions of the plasmid.

Example 11

Maize Plant Transformation

Maize plants can be transformed by methods known in the art, for example, see Examples 20-25 herein.

Example 12

Analysis of transgenic plants for copy number will be done in the following manner.

Leaf tissue is collected from a young leaf, from as close to the base as possible and from one side of the leaf. Samples are placed in 96-well plates lyophilized overnight. Tissues are homogenized by placing three 3 mm metal balls in each well and shaking using a Mega Grinder at 1200 rpm for 2 minutes. DNA is extracted using standard buffers containing beta-mercaptoethanol, Tris buffered to pH 8, EDTA, NaCl, and sodium dodecyl sulfate. Extraction is performed with potassium acetate followed by chloroform and precipitation is performed with isopropanol. Following centrifugation, washing with ethanol solution, and drying, DNA is resuspended in Tris-EDTA buffer prior to further analysis.

DNA is digested with multiple restriction endonucleases and fragments are separated by non-denaturing agarose gel electrophoresis. DNA is denatured by NaOH solution. The gel is neutralized in NaCl-containing Tris buffer and blotted to nylon filters by capillary action. Nylon filters are pre-hybridized in buffered solution containing salmon sperm DNA prior to addition of appropriate probes, either radioactive or DIG-labeled. Following hybridization, blots are washed and detected by exposure to autoradiography film or detection of DIG with anti-DIG antibody conjugates and appropriate substrates.

Example 13

We are using the full length open reading frame of cspA and cspB for expression in *E. coli* using vectors (Novagen, an affiliate of Merck KgaA, Darmstadt, Germany) that allow synthesis and purification of His-tagged antigen. Purified antigen will be used to generate polyclonal antibodies using a commercial provider, for example Strategic Biosolutions. Antibodies produced will be used to test plants for expression of CSP proteins.

Example 14

Transgenic maize line advancement. Primary transformants are generated in germplasm such as CORN OF GERMPLASM A, CORN OF GERMPLASM C, and CORN OF GERMPLASM D. Primary transformants are selfed as well as backcrossed to non-transgenic plants of the same inbred genotype. Seed from selfed plants is planted in the field and assayed by Taqman zygosity assay to identify putative homozygous selections, putative heterozygous selections, and negative selections. Putative heterozygous selections are crossed with multiple plants of appropriate testers, e.g. CORN OF GERMPLASM B and CORN OF GERMPLASM D. Hybrid seed is harvested, hand shelled, and pooled by selection. Other breeding methods may also be employed, for example, see example 29 herein.

Example 15

Seedlings will receive a treatment that limits available water to a sub-optimal level such that the treatment results in a measurable phenotypic response. For example, this treatment could take the form of restricting the amount of water over a number of days leading to a progressive water deficit, or the form of an acute deficit by osmotically stressing the seedlings hydroponically or with a salt treatment. Transgene positive plants will be screened for an improved phenotypic response to the treatment. The phenotypic responses measured may include shoot growth rate or dry weight accumulation during the treatment or following a post-treatment recovery period, wilting or wilt recovery, and root growth rates and dry weight accumulation. Those with improved response will be advanced to a field efficacy trial. Screens will require a number of transgene positive and transgene negative plants to be grown in small pots in a controlled environment such as a growth chamber or greenhouse. The number of plants screened is dictated by the variance associated with treatments applied and phenotypes measured.

Example 16

Field grown plants will receive a treatment that limits available water to a sub-optimal level such that the treatment results in a measurable phenotypic response. For example, this treatment could take the form of restricting the amount of water available to the plants over a number of days leading to a progressive water deficit either during late vegetative or early reproductive development of the plants. Transgene positive plants will be screened for an improved phenotypic response to the treatment relative to transgene negative plants. The phenotypic responses measured may include shoot growth rate during the treatment, leaf wilting, grain yield, and ear yield components such as kernel number and kernel weight. Those events with improved response will be advanced to a first year yield trial. Screens will be applied at typical planting densities at two dryland field locations with controllable irrigation. The number of plants screened is dictated by the variance associated with treatments applied and phenotypes measured.

Example 17

Several of the genes described will be cloned, transformed into plants, and be phenotyped in a manner similar to the following (Examples 17-30). For example, nucleotides and nucleotides encoding SEQ ID NOS: 4-53.

Construction of the Destination Vector.

A GATEWAY™ Destination (Invitrogen Life Technologies, Carlsbad, Calif.) plant expression vector was constructed (pMON65154, FIG. 13) using methods known to those of skill in the art. The elements of the expression vector are summarized in Table 17. The backbone of the plasmid pMON65154 comprising the bacterial replication functions and an ampicillin resistance gene expressed in *E. coli* were derived from the plasmid pSK-. The plant expression elements in pMON64154 are available to those of skill in the art and references are provided for each element in Table 17. All references in Table 17 to location refer to base pair coordinates for each element on the plasmid map disclosed in FIG. 13. Generally, pMON65154 comprises a selectable marker expression cassette comprising a Cauliflower Mosaic Virus 35S promoter operably linked to a gene encoding neomycin phosphotransferase II (nptII). The 3' region of the selectable marker expression cassette comprises the 3' region of the *Agrobacterium tumefaciense* nopaline synthase gene (nos) followed 3' by the 3' region of the potato proteinase inhibitor II (pinII) gene. The plasmid pMON 65154 further comprises a plant expression cassette into which a gene of interest may be inserted using GATEWAY™ cloning methods. The GATEWAY™ cloning cassette is flanked 5' by a rice actin 1 promoter, exon and intron and flanked 3' by the 3' region of the potato pinII gene. Using GATEWAY™ methods, the cloning cassette was replaced by a gene of interest. The vector pMON65154 and derivaties thereof comprising a gene of interest, were particularly useful in methods of plant transformation via direct DNA delivery, such as microprjectile bombardment. One of skill in the art could construct an expression vector with similar features using methods known in the art. Furthermore, one of skill in the art would appreciate that other promoters and 3' regions would be useful for expression of a gene of interest and other selectable markers may be used.

TABLE 17

Elements of Plasmid pMON65154

| CASSETTE | FUNCTION | ELEMENT | LOCATION | REFERENCE |
|---|---|---|---|---|
| Plant gene of interest expression | Promoter | Rice actin 1 | 1796-2638 | Wang et al., 1992 |
| | Enhancer | Rice actin 1 exon 1, intron 1 | 2639-3170 | Wang et al., 1992 |
| GATEWAY ™ cloning | Recombination | AttR1 | 3188-3312 | GATEWAY ™ Cloning Technology Instruction Manual (Invitrogen Life Technologies, Carlsbad, CA) |
| | Bacterial chloramphenical resistance gene | CmR gene | 3421-4080 | GATEWAY ™ Cloning Technology Instruction Manual (Invitrogen Life Technologies, Carlsbad, CA) |
| | Bacterial negative selectable markers | ccdA, ccdB genes | 4200-4727 | GATEWAY ™ Cloning Technology Instruction Manual (Invitrogen Life Technologies, Carlsbad, CA) |
| | GATEWAY ™ recombination site | attR2 | 4768-4892 | GATEWAY ™ Cloning Technology Instruction Manual (Invitrogen Life Technologies, Carlsbad, CA) |
| Plant gene of interest expression cassette | 3' region | Potato pinII | 4907-5846 | An et al., 1989 |
| Plant selectable marker gene expression cassette | Promoter | Cauliflower Mosaic Virus 35S | 5895-6218 | U.S. Pat. No. 5,352,605 |
| | Selectable marker gene | nptII | 6252-7046 | U.S. Pat. No. 6,174,724 |
| | 3' region | nos | 7072-7327 | Bevan et al., 1983 |
| | 3' region | pinII | 7339-8085 | An et al., 1989 |
| Maintenance in *E. coli* | Origin of replication | ColE1 | 858-1267 | Oka et al, 1979 |
| Maintenance in *E. coli* | Origin of replication | F1 | 8273-3673 | Ravetch et al., 1977 |
| Maintenance in *E. coli* | Ampicillin resistance | bla | 8909-551 | Heffron et al., 1979 |

Figure 14:
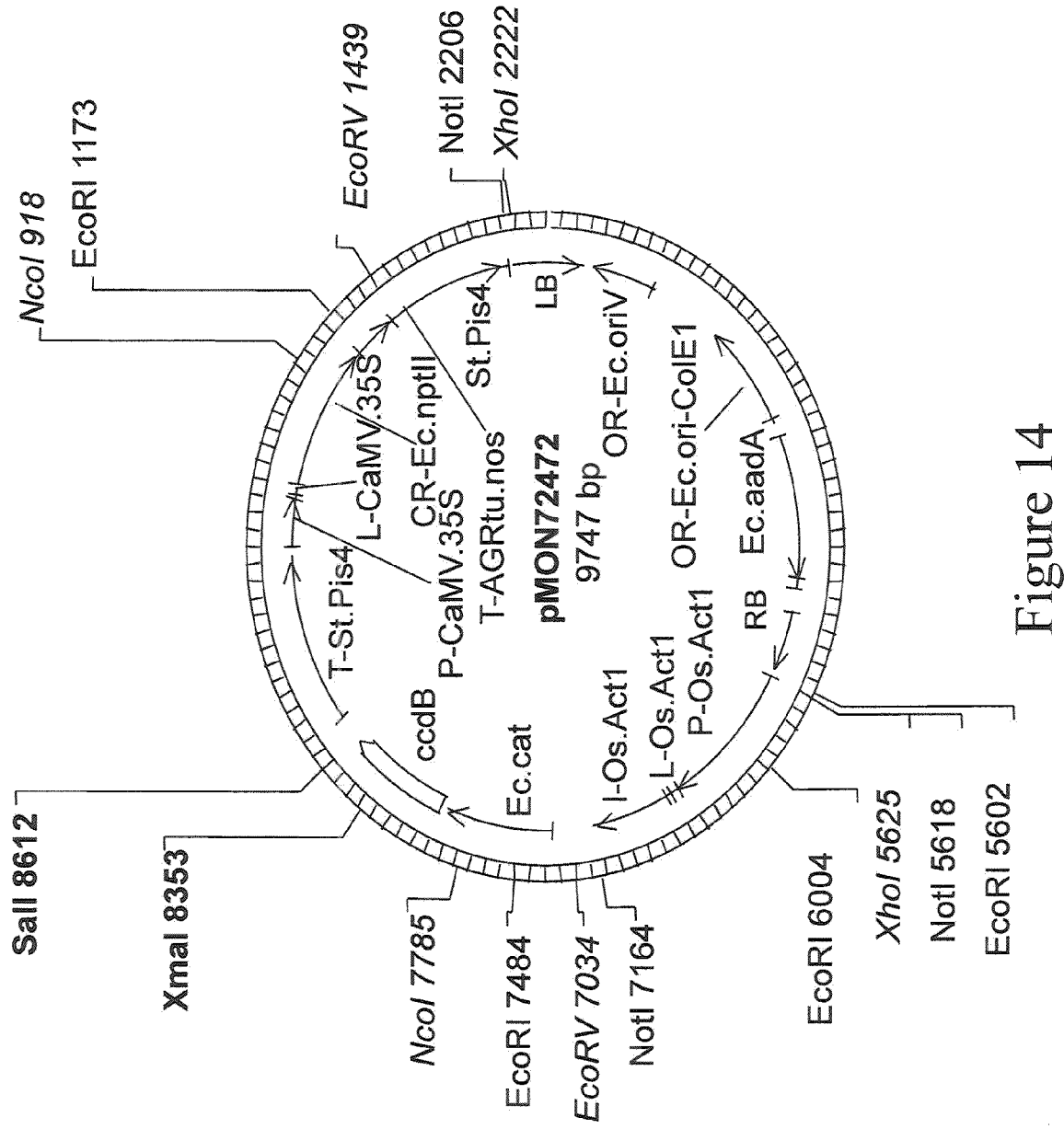
FIG. 14 shows a plasmid map of pMON72472.

A separate plasmid vector (pMON72472, FIG. 14) was constructed for use in *Agrobacterium* mediated methods of plant transformation. The plasmid pRG76 comprises the gene of interest plant expression, GATEWAY™ cloning, and plant selectable marker expression cassettes present in pMON65154. In addition left and right T-DNA border sequences from *Agrobacterium* were added to the plasmid. The right border sequence is located 5' to the rice actin 1 promoter and the left border sequence is located 3' to the pinII 3' sequence situated 3' to the nptII gene. Furthermore the pSK-backbone of pMON65164 was replaced by a plasmid backbone to facilitate replication of the plasmid in both *E. coli* and *Agrobacterium tumefaciens*. The backbone comprises an oriV wide host range origin of DNA replication functional in *Agrobacterium*, the rop sequence, a pBR322 origin of DNA replication functional in *E. coli* and a spectinomycin/stretptomycin resistance gene for selection for the presence of the plasmid in both *E. coli* and *Agrobacterium*.

The elements present in plasmid vector pRG81 are described in Table 18.

TABLE 18

Genetic Elements of Plasmid Vector pRG81

| CASSETTE | FUNCTION | ELEMENT | LOCATION | REFERENCE |
|---|---|---|---|---|
| Plant gene of interest expression | Promoter | Rice actin 1 | 5610-6452 | Wang et al., 1992 |
| | Enhancer | Rice actin 1 exon 1, intron 1 | 6453-6984 | Wang et al., 1992 |
| GATEWAY ™ cloning | Recombination | AttR1 | 7002-7126 | GATEWAY ™ Cloning Technology Instruction Manual (Invitrogen Life Technologies, Carlsbad, CA) |
| | Bacterial chloramphenical resistance gene | CmR gene | 7235-7894 | GATEWAY ™ Cloning Technology Instruction Manual (Invitrogen Life Technologies, Carlsbad, CA) |

TABLE 18-continued

Genetic Elements of Plasmid Vector pRG81

| CASSETTE | FUNCTION | ELEMENT | LOCATION | REFERENCE |
|---|---|---|---|---|
| | Bacterial negative selectable markers | ccdA, ccdB genes | 8014-8541 | GATEWAY ™ Cloning Technology Instruction Manual (Invitrogen Life Technologies, Carlsbad, CA) |
| | GATEWAY ™ recombination site | attR2 | 8582-8706 | GATEWAY ™ Cloning Technology Instruction Manual (Invitrogen Life Technologies, Carlsbad, CA) |
| Plant gene of interest expression cassette | 3' region | Potato pinII | 8721-9660 | An et al., 1989 |
| Plant selectable marker gene expression cassette | Promoter | Cauliflower Mosaic Virus 35S | 1-324 | U.S. Pat. No. 5,352,605 |
| | Selectable marker gene | nptII | 358-1152 | U.S. Pat. No. 6,174,724 |
| | 3' region | nos | 1178-1433 | Bevan et al., 1983 |
| | 3' region | pinII | 1445-2191 | An et al., 1989 |
| *Agrobacterium* mediated transformation | DNA transfer | Left border | 2493-2516 | Zambryski et al., 1982; GenBank Accession AJ237588 |
| Maintenance of plasmid in *E. coli* or *Agrobacterium* | Origin of replication | Ori-V | 2755-3147 | Honda et al., 1988 |
| Maintenance of plasmid in *E. coli* | Origin of replication | ColE1 | 3545-4199 | Oka et al., 1972 |
| Maintenance of plasmid in *E. coli* or *Agrobacterium* | Spectinomycin/ststreptomycin resistance | Spc/Str | 4242-5030 | Fling et al., 1985 |
| *Agrobacterium* mediated transformation | DNA transfer | Right border | 5514-5538 | Zambryski et al., 1982; GenBank Accession AJ237588 |

Example 18

Figure 13:
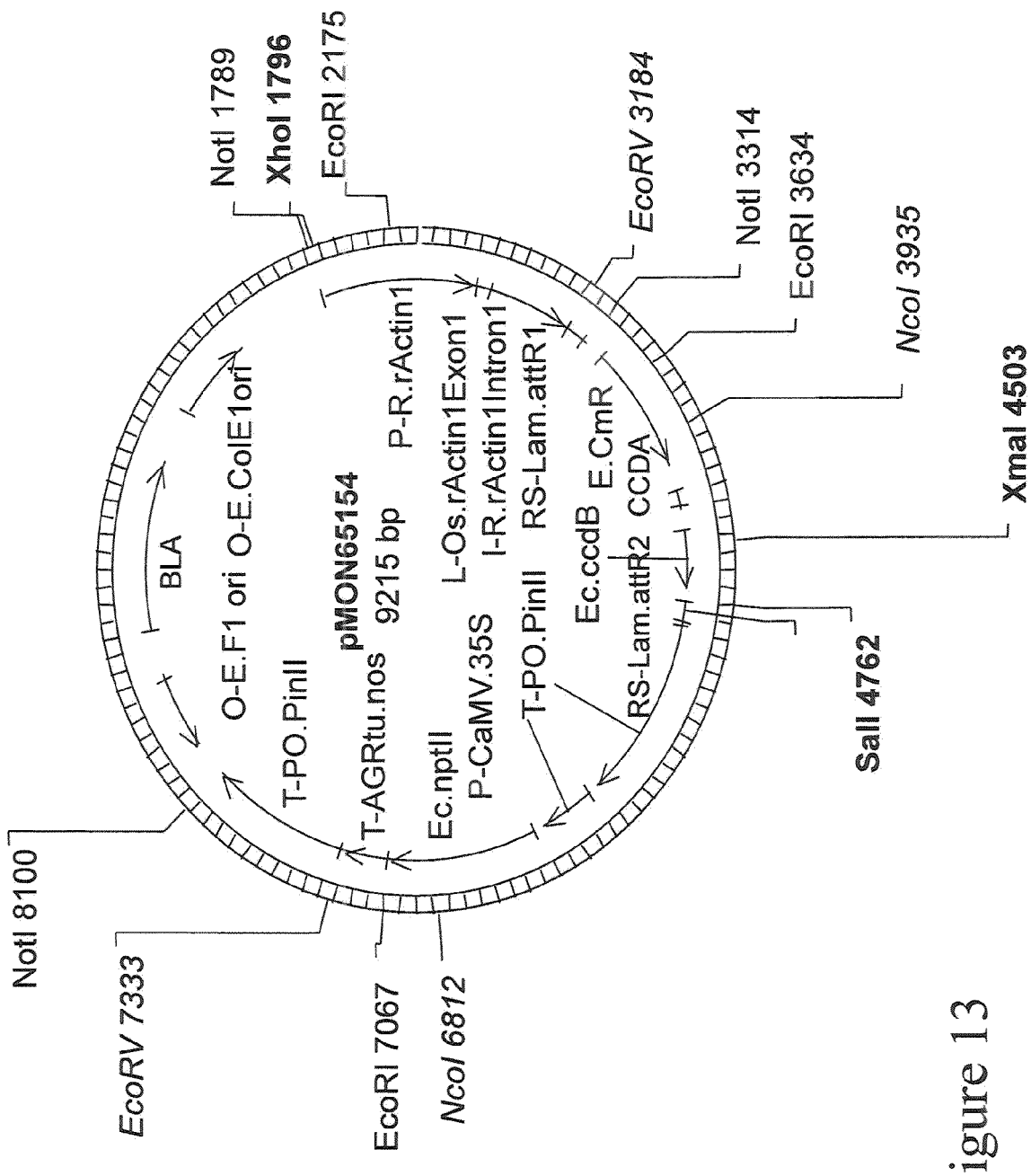
FIG. 13 shows a plasmid map of pMON65154.

Coding sequences were amplified by PCR prior to insertion in a GATEWAY™ Destination plant expression vector such as pMON65154 (FIG. 13). All coding sequences were available as either a cloned full length sequence or as DNA sequence information which allowed amplification of the desired sequence from a cDNA library. Primers for PCR amplification were designed at or near the start and stop codons of the coding sequence, in order to eliminate most of the 5' and 3' untranslated regions. PCR products were tailed with attB1 and attB2 sequences in order to allow cloning by recombination into GATEWAY™ vectors (Invitrogen Life Technologies, Carlsbad, Calif.).

Two methods were used to produce attB flanked PCR amplified sequences of interest. Both methods are described in detail in the GATEWAY™ Cloning Technology Instruction Manual (Invitrogen Life Technologies, Carlsbad, Calif.). In the first method, a single primer set comprising attB and template specific sequences was used. The primer sequences are as follows:

```
attB1 forward primer:
                                       (SEQ ID NO: 71)
5' GGG CAC TTT GTA CAA GAA AGC TGG GTN template
specific sequence 3' attB2 reverse primer
                                       (SEQ ID NO: 72)
5' GGGG CAC TTT GTA CAA GAA AGC TGG GTN template
specific sequence 3'
```

Alternatively, attB adapter PCR was used to prepare attB flanked PCR products. attB1 adapter PCR uses two sets of primers, i.e., gene specific primers and primers to install the attB sequences. Desired DNA sequence primers were designed which included 12 base pairs of the attB1 or attB2 sequences at the 5' end. The primers that were used were as follows:

```
attB1 gene specific forward primer
                                       (SEQ ID NO: 73)
5' CCTGCAGGACCATG forward gene specific primer 3' attB2 gene specific reverse primer
                                       (SEQ ID NO: 74)
5' CCTGCAGGCTCGAGCTA reverse gene specific
primer 3'
```

The second set of primers were attB adapter primers with the following sequences:

```
attB1 adapter forward primer
                                       (SEQ ID NO: 75)
5' GGGGACAAGTTTGTACAAAAAAGCAGGCTCCTGCAGGACCATG 3' attB2 adapter reverse primer
                                       (SEQ ID NO: 76)
5' GGGGACCACTTTGTACAAGAAAGCTGGGTCCCTGCAGGCTCGA
GCTA 3'
``` attB1 and attB2 flanked sequences were amplified by PCR according to the methods described by Invitrogen Life Technologies (Carlsbad, Calif.). attB flanked PCR products were purified and recovered from a gel as described above.

Figure 15:
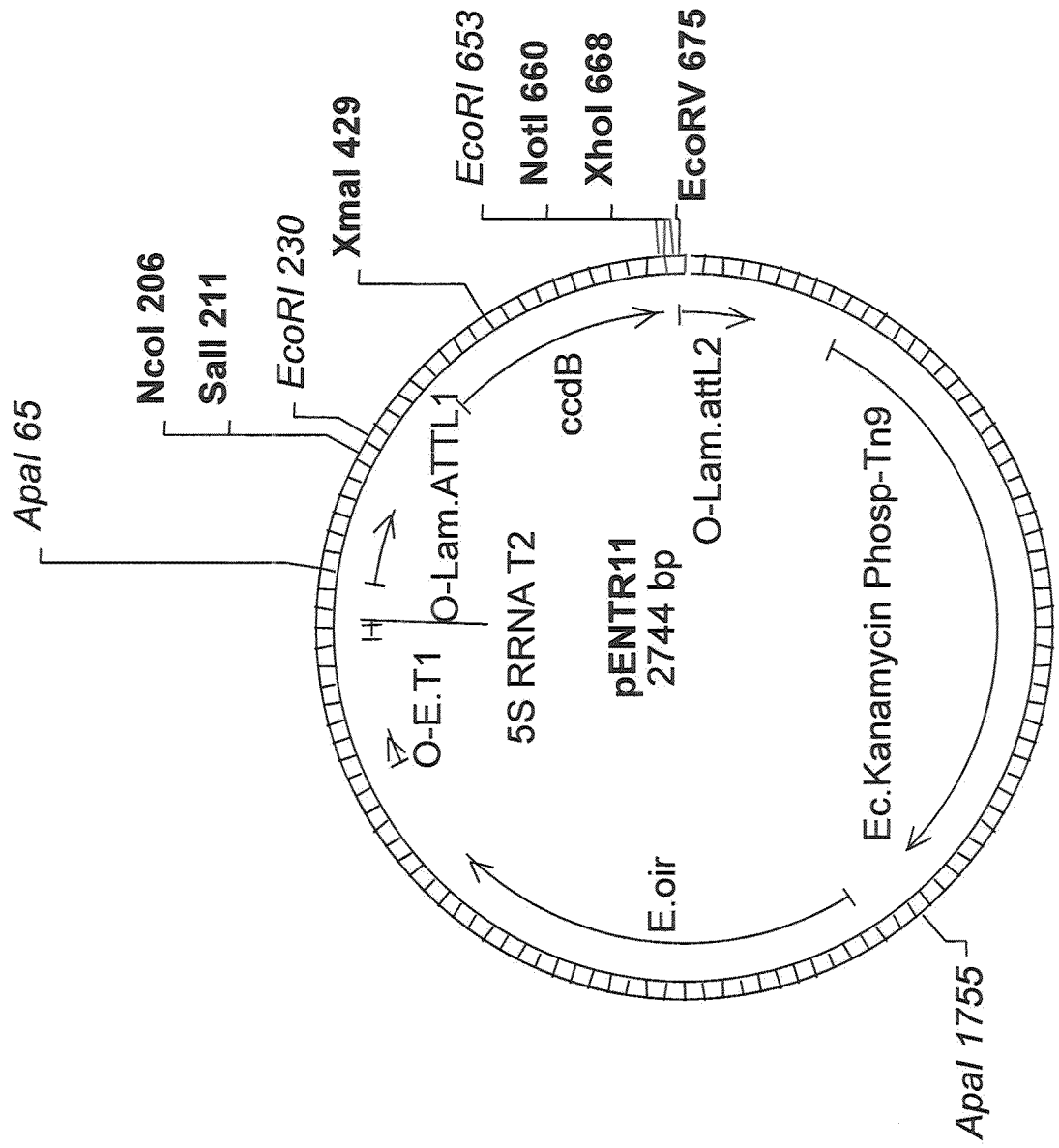
FIG. 15 shows a plasmid map of pENTR1.

In some instances, attB flanked sequences were recovered from PCR, but could not be inserted into the Donor Vector using GATEWAY™ technology. Conventional cloning methods using ligases were used to insert a DNA sequence into an Entry Vector (Invitrogen Life Technologies, Carlsbad, Calif.) when GATEWAY™ recombination into the Donor Vector failed. The choice of Entry Vector depended on the compatibility of restriction endonuclease sites in the Entry Vector and desired insert sequence. The Entry Vector was digested with a selected restriction endonuclease to remove the ccdB gene, dephosphorylated and gel purified. The selected restriction endonuclease depeneded on the Entry Vector used and the sequence of the desired insert sequence. For example, the ccdB gene was removed from pENTR11 (FIG. 15) using EcoR1 or other combinations of restriction endonucleases such as EcoRV, and XmaI or NcoI and XhoI. Other restriction nucleases could be used with other Entry Vectors for use in the GATEWAY™ process. To use restriction endonuclease digested Entry Vectors, it was necessary to be able to produce compatible sticky ends on the desired PCR product. Sticky ends could be produced by a number of methods known to those of skill in the art, such as restriction endonuclease digestion, adapter ligation or addition of restriction sites during PCR.

In some instances, it was not possible to produce compatible sticky ends on a PCR fragment and an Entry Vector. Alternatively, compatible sticky ends could be produced directed by restriction enzyme digestion of a cDNA clone. It was possible, however, to blunt end ligate PCR fragments into an Entry Vector. Using this method, the Entry Vector was cut with a restriction endonuclease to remove the ccdB gene. A gel purified linear Entry Vector was made blunt ended with T4 DNA polymerase. One of skill in the art is aware of other methods of making blunt ended DNA molecules, such as the use of Klenow DNA polymerase. The PCR product was made blunt ended and preferably dephosphorylated by incubation with T4 DNA polymerase, or another suitable polymerase, T4 polynucleotide kinase and a phosphatase enzyme. The Entry Vector and PCR product were blunt end ligated using methods known in the art. Ligation products were transformed into E. coli and plasmids from individual colonies analyzed for presence of the insert DNA and the desired orientation relative to the attL sites in the Entry Vector. Clones with the attL1 sequence next to the amino end of the open reading frame were selected.

Preferably, the TA method of cloning PCR products (Marchuk et al., 1991) was used when attB flanked PCR products could not be inserted into a plasmid using GATEWAY™ methods. The TA method takes advantage of Taq polymerase terminal transferase activity. An Entry Vector was cut with a restriction endonuclease and made blunt ended using the methods described herein. The blunt ended linear Entry Vector was incubated with dTTP and Taq polymerase resulting in the addition of a single thymidine residue at the 3' end of each DNA strand. Since Taq polymerase has a strong preference for dATP, PCR products are most often produced with a single adenosine added to the 3' end. Therefore, the Entry Vector and PCR product have complimentary single base 3' overhangs. Following ligation under conditions known to those of skill in the art, plasmids were transformed into E. coli. Plasmids were isolated from individual colonies and analyzed to identify plasmids with the desired insert in the correct orientation. Alternatively, PCR products, tailed with attB sites were TA cloned into a commercial TA cloning vector, such as pGEM-T EASY (Promega Corporation, Madison, Wis.).

All PCR amplification products were sequenced prior to introduction into a plant. PCR inserts in Destination expression vectors produced by GATEWAY™ methods were sequenced to confirm that the inserted sequenced encoded the expected amino acid sequence. If Entry Vectors were produced using ligation methods, the inserted sequence was sequenced in the Entry Vector prior to production of the Destination expression vector using GATEWAY™ technology. Point mutations which did not affect the amino acid coding sequence, i.e., silent mutations, were accepted.

Example 19

Construction of Expression Vectors

GATEWAY™ cloning methods (Invitrogen Life Technologies, Carlsbad, Calif.) were used to construct expression vectors for use in maize transformation. The GATEWAY™ methods are fully described in the GATEWAY™ Cloning Technology Instruction Manual (Invitrogen Life Technologies, Carlsbad, Calif.). Use of the GATEWAY™ system facilitates high throughput cloning of coding sequences into a plant expression vector. Gene sequences flanked by attB1 and attB2 sequences were produced by PCR as described above. Depending on which recombination sequence, attB1 and attB2, was placed 5' and 3' to the coding sequence, sense or antisense expression vectors were produced. A plant expression vector, pMON65154 (FIG. 13), into which any coding sequence could be inserted in a sense or antisense orientation was constructed as described in Example 1 and was used as a destination vector in the GATEWAY™ cloning process.

Two alternative processes were used for inserting a PCR amplified coding sequence into a plant expression vector. In the first method, a PCR product comprising the coding sequence of interest flanked by attB1 and attB2 sequences at the 5' and 3' ends was incubated with the donor vector (pDONR201™, Invitrogen Life Technologies, Carlsbad, Calif.) in the presence of BP CLONASE™. GATEWAY™ entry clones were produced from this reaction and transformed into E. coli. Plasmid DNA was isolated from entry clones. Inserted coding sequences could be sequenced from entry vectors in order to confirm the fidelity of PCR amplification. Plasmid DNA, isolated from entry clone E. coli colonies, was incubated with linearized destination vector, preferably pMON65154, in the presence of LR CLONASE™ to produce plant expression vectors comprising the coding sequence of interest. DNA from the LR CLONASE™ reaction was transformed into E. coli. Plasmid DNA from destination expression vectors was isolated and sequenced in order to determine correct orientation and sequence of the plant expression vector.

In the second method of generating plant expression vectors, a PCR product flanked by attB1 and attB2 sequences was incubated with a donor vector (pDONR201™, Invitrogen Life Technologies, Carlsbad, Calif.), and BP CLONASE™ as described above. Following incubation, an aliquot of the reaction mix was further incubated with linearized destination vector and LR CLONASE™. The resultant DNA was transformed into E. coli and plant expression vectors containing the coding sequence of interest selected using PCR or Southern blot analysis techniques known in the art. Both methods of producing plant expression vectors comprising a coding sequence of interest were described by Invitrogen Life Technologies (GATEWAY™ Cloning Technology Instruction Manual).

Alternatively, Entry Vectors were produced using restriction endonucleases and ligases. Entry Vectors are available from Invitrogen Life Technologies (Carlsbad, Calif.). Each entry vector, e.g., pENTR1A, pENTR2B, pENTR3c, pENTR4, and pENTR11, has unique cloning and expression features. pENTR11 was preferably used in the practice of the present invention. Those of skill in the art will recognize the usefulness of the other Entry Vectors. Before using restriction endonucleases and ligases to insert desired sequences into one of the Entry Vectors, it was necessary to restriction digest the Entry Vector on each side of the ccdB gene. A number of different combinations of restriction endonucleases were used depending on the restriction sites present on the DNA sequence to be inserted into the Entry Vector. Preferably the Entry Vector was dephosphorylated and gel purified after restriction digestion. The desired DNA sequence was inserted into the Entry Vector using conventional methods of molecular biology known to those of skill in the art. TA cloning (U.S. Pat. No. 5,827,657) is a preferable method of cloning PCR fragments into an Entry Vector.

Vectors (designated as pMON and a 5 digit number) and coding sequences contained therein that were produced using the GATEWAY™ cloning methods are, for example, SEQ ID NOS: 4-28. It is expected that some of the coding sequences of the present invention may be cloned into a plant expression vectors using the methods described herein.

Example 20

CORN OF GERMPLASM A plants were grown in the greenhouse. Ears were harvested from plants when the embryos were 1.5 to 2.0 mm in length, usually 10 to 15 days after pollination, and most frequently 11 to 12 days after pollination. Ears were surface sterilized by spraying or soaking the ears in 80% ethanol, followed by air drying. Alternatively, ears were surface sterilized by immersion in 50% CLOROX™ containing 10% SDS for 20 minutes, followed by three rinses with sterile water.

Immature embryos were isolated from individual kernels using methods known to those of skill in the art. Immature embryos were cultured on medium 211 (N6 salts, 2% sucrose, 1 mg/L 2,4-D, 0.5 mg/L niacin, 1.0 mg/L thiamine-HCl, 0.91 g/L L-asparagine, 100 mg/L myo-inositiol, 0.5 g/L MES, 100 mg/L casein hydrolysate, 1.6 g/L MgCl$_2$, 0.69 g/L L-proline, 2 g/L GELGRO™, pH 5.8) containing 16.9 mg/L AgNO$_3$, (designated medium 211V) for 3-6 days, preferably 3-4 days prior to microprojectile bombardment.

Example 21

Methods of Agrobacterium mediated transformation of maize cells and other monocots are known (Hiei et al., 1997; U.S. Pat. No. 5,591,616; U.S. Pat. No. 5,981,840; published EP patent application EP 0 672 752). Although various strains of Agrobacterium may be used (see references above), strain ABI is used preferably by the present inventors. The ABI strain of Agrobacterium is derived from strain A208, a C58 nopaline type strain, from which the Ti plasmid was eliminated by culture at 37° C., and further containing the modified Ti plasmid pMP90RK (Koncz and Schell, 1986). An Agrobacterium tumefaciens binary vector system (An et al., 1998) is preferably used to transform maize. Alternative cointegrating Ti plasmid vectors have been described (Rogers et al., 1988) and could be used to transform maize. A binary vector comprising one or more genes of interest may be introduced into a disarmed Agrobacterium strain using electroporation (Wen-jun and Forde, 1989) or triparental mating (Ditta et al., 1980). A binary vector may contain a selectable marker gene, a screenable marker gene and/or one or more genes that confer a desirable phenotypic trait on the transformed plant.

Figure 4:
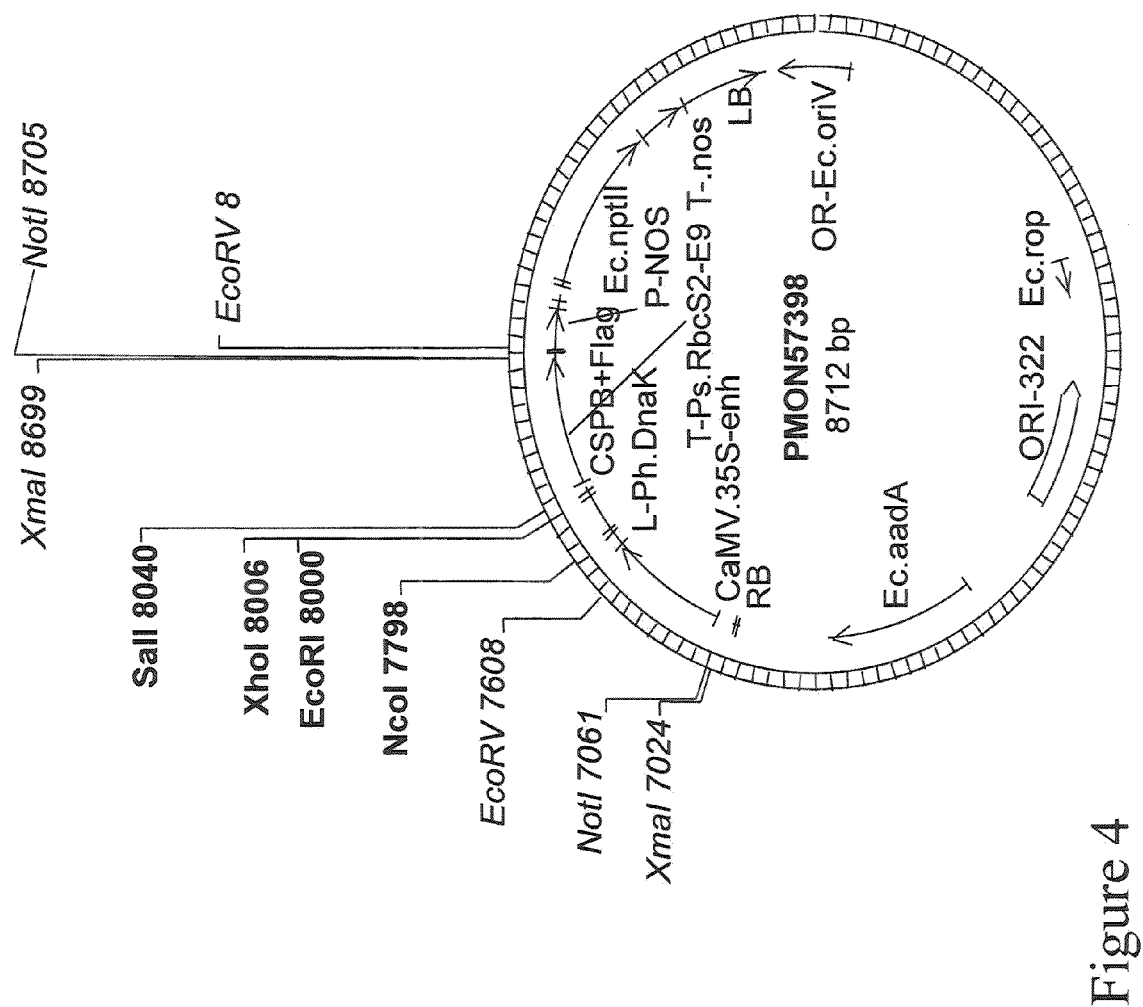
FIG. 4 shows a plasmid map of pMON57398.
Figure 5:
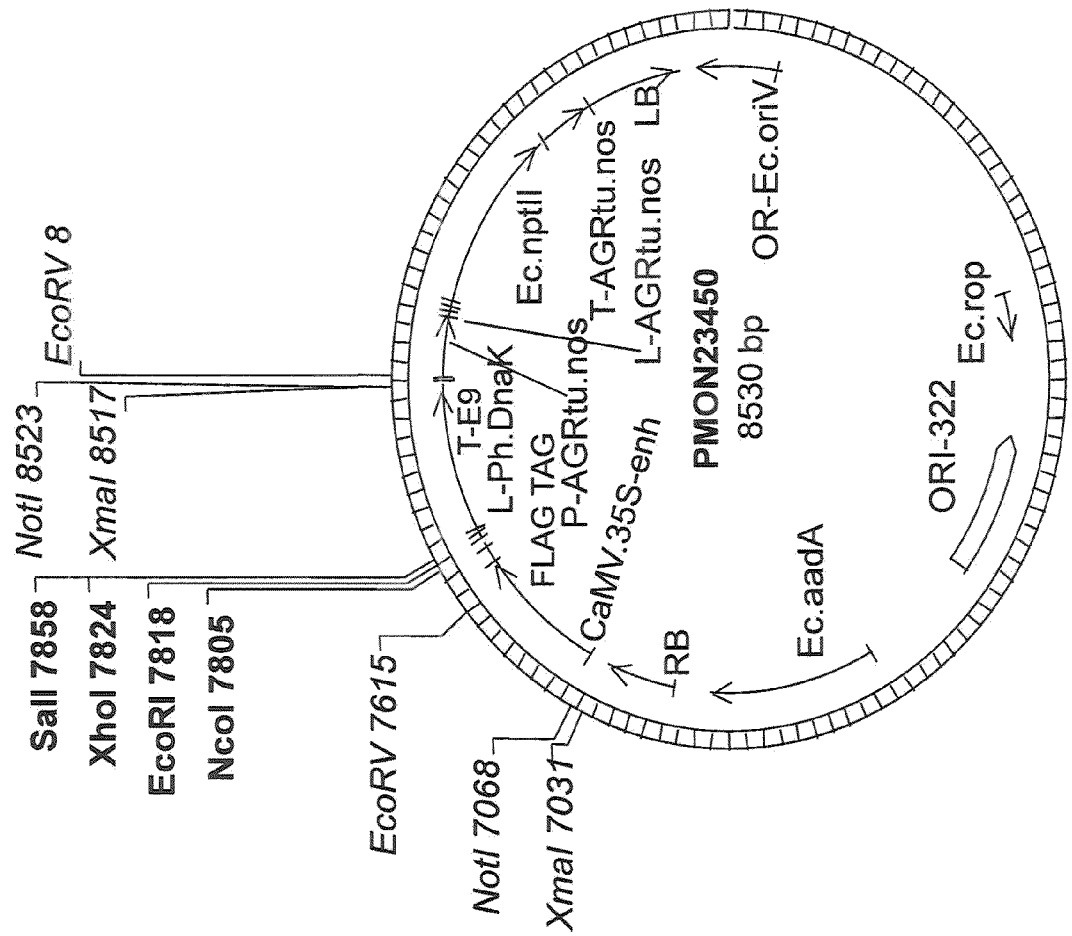
FIG. 5 shows a plasmid map of pMON23450.

An exemplary binary vector, pMON30113, is shown in FIG. 4. Other binary vectors may be used and are known to those of skill in the art.

Prior to co-culture of maize cells, Agrobacterium cells may be grown at 28° C. in LB (DIFCO) liquid medium comprising appropriate antibiotics to select for maintenance of the modified Ti plasmid and binary vector. For example, ABI/pMON30113, may be grown in LB medium containing 50 ug/ml kanamycin to select for maintenance of the pMP90RK modified Ti plasmid and 100 ug/ml spectinomycin to select for maintenance of the binary vector pMON30113. It will be obvious to one of skill in the art to use appropriate selection agents to maintain plasmids in the host Agrobacterium strain. Prior to inoculation of maize cells, Agrobacterium cells are grown overnight at room temperature in AB medium (Chilton et al., 1974) comprising appropriate antibiotics for plasmid maintenance and 200 uM acetosyringone. Immediately prior to inoculation of maize cells, Agrobacterium are preferably pelleted by centrifugation, washed in ½ MSVI medium (2.2 g/L GIBCO (Carlsbad, Calif.) MS salts, 2 mg/L glycine, 0.5 g/L niacin, 0.5 g/L L-pyridoxine-HCl, 0.1 mg/L thiamine, 115 g/L L-proline, 10 g/L D-glucose, and 10 g/L sucrose, pH 5.4) containing 200 uM acetosyringone, and resuspended at 0.1 to 1.0×10$^9$ cells/ml in ½ MSPL medium (2.2 g/L GIBCO (Carlsbad, Calif.) MS salts, 2 mg/L glycine, 0.5 g/L niacin, 0.5 g/L L-pyridoxine-HCl, 0.1 mg/L thiamine, 115 g/L L-proline, 26 g/L D-glucose, 68.5 g/L sucrose, pH 5.4) containing 200 uM acetosyringone. One of skill in the art may substitute other media for ½ MSVI or ½ MSPL.

Immature maize embryos are isolated as described previously. Embryos are inoculated with Agrobacterium 0-7 days after excision, preferably immediately after excision. Alternatively, immature embryos may be cultured for more than 7 days. For example, embryogenic callus may be initiated as described above and co-cultured with Agrobacterium. Preferably, immature maize embryos are excised, immersed in an Agrobacterium suspension in ½ MSPL medium prepared as described above and incubated at room temperature with Agrobacterium for 5-20 minutes.

Following inoculation embryos are transferred to one-half strength MS medium (Murashige and Skoog, 1962) containing 3.0 mg/L 2,4-dichlorophenyoxyacetic acid (2,4-D), 1% D-glucose, 2% sucrose, 0.115 g/L L-proline, 0.5 mg/L thiamine-HCl, 200 uM acetosyringone, and 20 uM silver nitrate or silver thiosulfate. Immature embryos are co-cultured with Agrobacterium for 1 to 3 days at 23° C. in the dark. One of skill in the art may substitute other media for the described media.

Co-cultured embryos are transferred to medium 15AA (462 mg/L (NH4)SO4, 400 mg/L KH2PO4, 186 mg/L MgSO4-7H20, 166 mg/L CaCl2-2H20, 10 mg/L MnSO4-H2O, 3 mg/L H3B03, 2 mg/L ZnSO4-7H20, 0.25 mg/L NaMoO4-2H20, 0.025 mg/L CuSO4-5H20, 0.025 mg/L CoCl2-6H20, 0.75 mg/L KI, 2.83 g/L KNO3, 0.2 mg/L niacin, 0.1 mg/L thiamine-HCl, 0.2 mg/L pyridoxine-HCl, 0.1 mg/L D-biotin, 0.1 mg/L choline chloride, 0.1 mg/L calcium pantothenate, 0.05 mg/L folic acid, 0.05 mg/L p-aminobenzoic acid, 0.05 mg/L riboflavin, 0.015 mg/L vitamin B12, 0.5 g/L casamino acids, 33.5 mg/L Na2EDTA, 1.38 g/L L-proline, 20 g/L sucrose, 10 g/L D-glucose), or MS medium containing 1.5 mg/L 2,4-D, 500 mg/L carbenicillin, 3% sucrose, 1.38 g/L L-proline and 20 uM silver nitrate or silver thiosulfate and cultured for 0 to 8 days in the dark at 27° C. without selection. Culture media used for selection of transformants and regeneration of plants preferably contains 500 mg/L carbenicillin. One of skill in the art may substitute other antibiotics that control growth of Agrobacterium. Other culture media that support cell culture may be used alternatively. In the absence of a delay of selection (0 day culture), selection may be initiated on 25 mg/L paromomycin. Selection medium may comprise medium 211 (described above) or a variant of medium 211 in which N6 salts are replaced by MS salts. After two weeks, embryogenic callus are transferred to culture medium containing 100 mg/L paromomycin and sub-cultured at about two week intervals. When selection is delayed following co-culture, embryos are initially cultured on medium containing 50 mg/L paromomycin followed by subsequent culture of embryogenic callus on medium containing 100-200 mg/L paromomycin. One of skill in the art will culture tissue on concentrations of paromomycin which inhibit growth of cells lacking the selectable marker gene, but a concentration on which transformed callus will proliferate. Alternatively, one may use other selectable markers to identify transformed cells. It is believed that initial culture on 25 to 50 mg/L paromocyin for about two weeks, followed by culture on 50-200 mg/L paromoycin will result in recovery of transformed callus. Transformants are recovered 6 to 8 weeks after initiation of selection. Plants are regenerated from transformed embryogenic callus as described above for transformants recovered following microprojectile bombardment.

Example 22

*Agrobacterium* Mediated Transformation of Maize Callus

This example describes methods for transformation of maize callus using *Agrobacterium*. The method is exemplified using an nptII selectable marker gene and paromomycin selective agent. One of skill in the art will be aware of other selectable marker and selective agent combinations that could be used alternatively.

Callus was initiated from immature embryos using methods known to those of skill in the art. For example, 1.5 mm to 2.0 mm immature embryos were excised from developing maize seed of a genotype such as CORN OF GERMPLASM A and cultured with the embryonic axis side down on medium 211V, usually for 8-21 days after excision. Alternatively, established an established callus culture may be initiated and maintained by methods known to those of skill in the art.

*Agrobacterium* was prepared for inoculation of plant tissue according to the methods described in Example 21. Fifty to 100 pieces of callus was transferred to a 60 mm×20 mm petri dish containing about 15 ml of *Agrobacterium* suspension at 0.1 to $1.0 \times 10^9$ cfu/ml. A piece of callus was usually all of the callus produced by an immature embryo in up to 21 days of culture or a piece of established callus of 2 mm to 8 mm in diameter. Callus was incubated for about 30 minutes at room temperature with the *Agrobacterium* suspension, followed by removal of the liquid by aspiration.

About 50 µL of sterile distilled water was added to a Whatman #1 filter paper in a 60 mm×20 mm petri dish. After 1-5 minutes, 15 to 20 pieces of callus were transferred to each filter paper and the plate sealed with PARAFILM®, for example. The callus and *Agrobacterium* were co-cultured for about 3 days at 23° C. in the dark.

Calli were transferred from filter paper to medium 211 with 20 µM silver nitrate and 500 mg/L carbenicillin and cultured in the dark at 27° C. to 28° C. for 2-5 days, preferably 3 days. Selection was initiated by transferring callus to medium 211 containing 20 µM silver nitrate, 500 mg/L carbenicillin and 25 mg/L paromomycin. After 2 weeks culture in the dark at 27° C. to 28° C., callus was transferred to medium 211 with 20 µM silver nitrate, 500 mg/L carbenicillin and 50 mg/L paromomycin (medium 211QRG). Callus was subcultured after two weeks to fresh medium 211 QRG and further cultured for two weeks in the dark at 27° C. to 28° C. Callus was then transferred to medium 211 with 20 µM silver nitrate, 500 mg/L carbenicillin and 75 mg/L paromomycin. After 2-3 weeks culture in the dark at 27° C. to 28° C., paromomycin resistant callus was identified. One of skill in the art would recognize that times between subcultures of callus are approximate and one may be able to accelerate the selection process by transferring tissue at more frequent intervals, e.g., weekly rather than biweekly.

Plants were regenerated from transformed callus, transferred to soil and grown in the greenhouse as described. Following *Agrobacterium* mediated transformation, medium 217 (see Example 9) further contained 500 mg/L carbenicillin and medium 127T (see Example 9) further contained 250 mg/L carbenicillin. Transformed maize plants comprising genes of the present invention that were produced using *Agrobacterium* mediated transformation are summarized in table Y.

Example 23

Methods of Microprojectile Bombardment

Approximately four hours prior to microprojectile bombardment, immature embryos were transferred to medium 211SV (medium 211V with the addition of sucrose to 12%). Twenty five immature embryos were preferably placed in a 60×15 mm petri dish, arranged in a 5×5 grid with the coleoptilar end of the scutellum pressed slightly into the culture medium at a 20 degree angle. Tissue was maintained in the dark prior to bombardment.

Prior to microprojectile bombardment, a suspension of gold particles was prepared onto which the desired DNA was precipitated. Ten milligrams of 0.6 µm gold particles (Bio-Rad) were suspended in 50 µL buffer (150 mM NaCl, 10 mM Tris-HCl, pH 8.0). Twenty five µL of a 2.4 nM solution of the desired DNA was added to the suspension of gold particles and gently vortexed for about five seconds. Seventy five µL of 0.1M spermidine was added and the solution vortexed gently for about 5 seconds. Seventy five µL of a 25% solution of polyethylene glycol (3000-4000 molecular weight, American Type Culture Collection) was added and the solution was gently vortexed for five seconds. Seventy five µL of 2.5 M $CaCl_2$ was added and the solution vortexed for five seconds. Following the addition of $CaCl_2$, the solution was incubated at room temperature for 10 to 15 minutes. The suspension was subsequently centrifuged for 20 seconds at 12,000 rpm (Sorval MC-12V centrifuge) and the supernatant discarded. The gold particle/DNA pellet was washed twice with 100% ethanol and resuspended in 10 mL 100% ethanol. The gold particle/DNA preparation was stored at −20° C. for up to two weeks.

DNA was introduced into maize cells using the electric discharge particle acceleration gene delivery device (U.S. Pat. No. 5,015,580). The gold particle/DNA suspension was coated on Mylar sheets (Du Pont Mylar polyester film type SMMC2, aluminum coated on one side, over coated with PVDC co-polymer on both sides, cut to 18 mm square) by dispersion of 310 to 320 µL of the gold particle/DNA suspension on a sheet. After the gold particle suspension settled for one to three minutes, excess ethanol was removed and the sheets were air dried. Microprojectile bombardment of maize tissue was conducted as described in U.S. Pat. No. 5,015,580. AC voltage may be varied in the electric discharge particle delivery device. For microprojectile bombardment of CORN OF GERMPLASM A pre-cultured immature embryos, 35% to 45% of maximum voltage was preferably used. Following microprojectile bombardment, tissue was cultured in the dark at 27° C.

Example 24

Selection of Transformed Cells

Transformants were selected on culture medium comprising paromomycin, based on expression of a transgenic neomycin phosphotransferase II (nptII) gene. Twenty four hours after DNA delivery, tissue was transferred to 211V medium containing 25 mg/L paromomycin (medium 211HV). After three weeks incubation in the dark at 27° C., tissue was transferred to medium 211 containing 50 mg/L paromomycin (medium 211G). Tissue was transferred to medium 211 containing 75 mg/L paromomycin (medium 211XX) after three weeks. Transformants were isolated following 9 weeks of selection. Table Y discloses results of transformant experiments using the methods of microprojectile bombardment disclosed herein.

Example 25

Regeneration of Fertile Transgenic Plants

Fertile transgenic plants were produced from transformed maize cells. Transformed callus was transferred to medium 217 (N6 salts, 1 mg/L thiamine-HCl, 0.5 mg/L niacin, 3.52 mg/L benzylaminopurine, 0.91 mg/L L-asparagine monohydrate, 100 mg/L myo-inositol, 0.5 g/L MES, 1.6 g/L $MgCl_2$-$6H_2O$, 100 mg/L casein hydrolysate, 0.69 g/L L-proline, 20 g/L sucrose, 2 g/L GELGRO™, pH 5.8) for five to seven days in the dark at 27° C. Somatic embryos mature and shoot regeneration began on medium 217. Tissue was transferred to medium 127T (MS salts, 0.65 mg/L niacin, 0.125 mg/L pyridoxine-HCl, 0.125 mg/L thiamine-HCl, 0.125 mg/L Ca pantothenate, 150 mg/L L-asparagine, 100 mg/L myo-inositol, 10 g/L glucose, 20 g/L L-maltose, 100 mg/L paromomycin, 5.5 g PHYTAGAR™, pH 5.8) for shoot development. Tissue on medium 127T was cultured in the light at 400-600 lux at 26° C. Plantlets are transferred to soil, preferable 3 inch pots, about four to 6 weeks after transfer to 127T medium when the plantlets are about 3 inches tall and have roots. Plants were maintained for two weeks in a growth chamber at 26° C., followed by two weeks on a mist bench in a greenhouse before transplanting to 5 gallon pots for greenhouse growth. Plants were grown in the greenhouse to maturity and reciprocal pollinations were made with the inbred CORN OF GERMPLASM A. Seed was collected from plants and used for further breeding activities.

Example 26

Isolation of Nucleic Acids from Plants

Nucleic acids were isolated from leaf tissue of R0 plants, collected and flash frozen in a 96 well collection box, 0 to 2 weeks after plantlets were transferred to soil. Approximately 100 milligrams of tissue was collected from each plant and stored at −80° C. until analysis.

DNA and RNA were isolated from a single tissue sample using the Qiagen Rneasy 96™ kit (Qiagen Inc., Valencia, Calif.) with modifications. One hundred milligrams of frozen tissue was homogenized in 7000, Rneasy™ RTL buffer (Qiagen Inc., Valencia, Calif.) using a Bead Beater™ (Biospec Products, Bartlesville, Okla.). Samples were centrifuged at 3200 rpm for 15 minutes and all of the supernatant transferred the wells of a Promega WIZARD™ clearing plate (Promega Corporation, Madison, Wis.). The sample solutions were clarified by vacuum filtration through the clearing plate. The cleared supernatant was used for nucleic acid extractions.

For DNA extractions, 70 µL of the cleared sample was transferred to a v-well PCR plate, covered with adhesive foil, and heated to 95° C. for 8 minutes. The samples were incubated at 0° C. for five minutes, followed by centrifugation for 3 minutes to remove insoluble materials. A Sephadex G-50 gel filtration box (Edge Biosystems, Gaithersburg, Mo.) was conditioned for 2 min at 2000 rpm. Forty µL of the heat-treated supernatant was loaded into each well and the box centrifuged for two minutes at 2500 rpm. An additional 20 µL, of TE buffer was added to the column effluent and the sample plate was stored at −20° C. until analysis.

For RNA extractions, five hundred microliters of cleared solution was transfer to a clean 96 well sample box. Two hundred and fifty microliters of 100% ethanol was added to each sample and the sample was thoroughly mixed. All of the approximately seven hundred and fifty microliters of solution was then loaded into the wells of a Qiagen Rneasy™ binding plate in a Promega WIZARD™ filtration unit. Five hundred microliters of RW1 buffer (Qiagen Inc., Valencia, Calif.) was added to each well and the buffer removed by vacuum filtration. Eighty microliters of RNAase free DNAase (Qiagen Inc., Valencia, Calif.) was added to each well, incubated at room temperature for 15 minutes the DNAase solution drawn through the wells by vacuum filtration. An additional five hundred microliters RW1 buffer (Qiagen Inc., Valencia, Calif.) was added to the wells and the buffer removed by vacuum filtration. The sample was further washed by vacuum filtration with 500 µL RPE buffer 2× (Qiagen, Valencia, Calif.). The extraction plate was placed on a microtiter plate and centrifuged for three minutes at 3000 rpm to remove any residual RPE buffer solution in the filter. Eighty microliters of RNA grade water (DNAse free) was added to each well, followed by incubation at room temperature for two minutes. The extraction plate and microtiter plate were centrifuged for three minutes at 3000 rpm and the RNA preparation stored frozen in the collection plate at −80° C.

Example 27

Assays for Copy Number

Copy number of transgenes in R0 plants was determined using TAQMAN® methods. The pMON65154 and pRG76 GATEWAY™ destination vectors were constructed with a sequence derived from the 3' region of the potato pinII gene which could be used to assay copy number of transgene insertions. The pinII forward and reverse primers were as follows:

```
                                          (SEQ ID NO: 77)
Forward primer      5' ccccaccctgcaatgtga 3'

(SEQ ID NO: 78)
Reverse primer      5' tgtgcatccttttatttcatacatta
                       attaa 3'
```

The pinII TAQMAN® probe sequence was

```
                                          (SEQ ID NO: 79)
          5' cctagacttgtccatcttctggattggcca 3'
```

The probe was labelled at the 5' end with the fluorescent dye FAM (6-carboyxfluorescein) and the quencher dye TAMRA (6-carboxy-N,N,N',N'-tetramethylrhodamine) was attached via a linker to the 3' end of the probe. The TAQ-MAN® probe was obtained from Applied Biosystems (Foster City, Calif.). _____ SAT, a single copy maize gene was used as an internal control in TAQMAN® copy number assays. The SAT primers were as follows

```
                                        (SEQ ID NO: 80)
Forward primer    5' gcctgccgcagaccaa 3'

(SEQ ID NO: 81)
Reverse primer    5' atgcagagctcagcttcatc 3'
```

The SAT TAQMAN® probe sequence was

```
5' tccagtacgtgcagtccctcctcc 3'  (SEQ ID NO: 82)
``` the probe was labelled at its 5' end with the fluorescent dye VIC™ (Applied Biosystems, Foster City, Calif.) and the quencher dye TAMRA at is 3' end.

TAQMAN® PCR was performed according to the manufacturer's instructions (Applied Biosystems, Foster City, Calif.). Five to 100 nanograms DNA was used in each assay. PCR amplification and TAQMAN® probe detection were performed in 1× TAQMAN® Universal PCR Master Mix (Applied Biosystems, Foster City, Calif.) which contains AmpliTaq Gold® DNA polymerase, AmpErase® UNG, dNTPs with dUTP, Passive Reference 1, and optimized buffer. Eight hundred nM each forward and reverse pinII primers and 150 nM pinII TAQMAN® probe were used in the TAQMAN® assay. 200 nM each Sat forward and reverse primers and 150 nM Sat TAQMAN® probe were used in the TAQMAN® copy number assay. TAQMAN® PCR was carried out for 2 minutes at 50° C., 10 minutes at 95° C., followed by 40 cycles of 15 seconds at 95° C. and one minute at 60° C. Real time TAQMAN® probe fluorescence was measured using an ABI Prism 7700 Sequence Detection System or ABI7900HT Sequence Detection System (Applied Biosystems, Foster City, Calif.). $C_T$ values were calculated according to the TAQMAN® EZ RT-PCR kit instruction manual (Applied Biosystems, Foster City, Calif.). The $\Delta\Delta C_T$ value was calculated as $C_T$ (internal control gene (Sat))–$C_T$ (transgene)–$C_T$ (internal control gene (Sat) in nontransgenic plant). The copy number was assigned as follows according to the criteria in Table 19.

TABLE 19

Critera for Copy Number Determination by TAQMAN ®

| Copy Number | Criteria |
|---|---|
| 1 | $-0.5 < \Delta\Delta C_T < 0.50$ |
| 2 | $0.5 < \Delta\Delta C_T < 1.50$ |
| >2 | $\Delta\Delta C_T > 1.50$ |

Plants comprising genes of the present invention will be analyzed by TAQMAN® methods for copy number. Southern blot analysis to confirm the TAQMAN® copy number determination in about 80% of the plants that were analyzed by both TAQMAN® and Southern blot hybridization.

Example 28

Assays for Gene Expression

Expression of a transgene of the present invention was assayed by TAQMAN® RT-PCR using the TAQMAN® EZ RT-PCR kit from Applied Biosystems (Foster City, Calif.). RNA expression was assayed relative to expression in a transgenic standard, a transgenic maize event designated DBT418, comprising a *B. thuringiensis* cryIAI gene operably linked to a pinII 3' untranslated region. The DBT418 event expresses the cryIAI gene at a level which confers commercial levels of resistance to lepdiopteran insects such as European Corn Borer and was commercially sold by DEKALB Genetics Corporation under the brand name DEKALBt®. The pMON65154 and pRG76 GATEWAYT™ destination vectors were constructed with a sequence derived from the 3' region of the potato pinII gene which could be used to assay transgene transcript levels for any coding sequence inserted into the Destination Vector. The pinII primers and probe previously described in were used for TAQMAN® RT-PCR. Ubiquitin fusion protein (UBI) RNA was used as an internal control in all TAQMAN® RT-PCR assays. The UBI primers used were as follows:

```
                                        (SEQ ID NO: 83)
Forward primer    5' cgtctacaatcagaaggcgtaatc 3'

(SEQ ID NO: 84)
Reverse primer    5' ccaacaggtgaatgcttgatagg 3'
```

The sequence of the UBI TAQMAN® probe was

```
5' catgcgccgctttgcttc 3'    (SEQ ID NO: 85)
```

The UBI TAQMAN® probe was labeled at its 5' end with the fluorescent dye VIC™ (Applied Biosystems, Foster City, Calif.) and the quencher dye TAMRA at is 3' end Reverse transcription, PCR amplification and TAQMAN® probing were performed according to the one step procedure described in the TAQMAN® EZ RT-PCR kit (Applied Biosystems, Foster City, Calif.). Five to 100 nanograms total RNA was used in each assay. In vitro transcribed control RNA from the DBT418 event was included as a control on every plate and run over a concentration range from 0.01 picograms to 10 picograms. Total RNA from DBT418 leaf and from the non-transgenic inbred CORN OF GERMPLASM A were run as positive and negative controls respectively. RT-PCR was performed in TAQMAN® EZ Buffer (50 mM Bicine, 115 mM potassium acetate, 0.01 mM EDTA, 60 mM Passive Reference 1, 8% glycerol, pH 8.2, Applied Biosystems, Foster City, Calif.) containing 3 mM manganese acetate, 300 μM each dATP, dCTP, dGTP, and dUTP, 100 units rTth™ (Applied Biosystems, Foster City, Calif.) DNA polymerase, and 25 units AmpErase UNG (Applied Biosytems, Foster City, Calif.). RT-PCR was caned out as follows: 2 minutes at 50° C., 30 minutes at 60° C., 5 minutes at 95° C., followed by 40 cycles of 20 seconds at 95° C. and 1 minute at 60° C. 400 nM each forward and reverse primers were used for amplification of the pinII sequence and 200 nM TAQMAN® pinII probe used for detection. UBI RNA was amplified using 400 nM each forward and reverse primers and 200 nM UBI TAQ-MAN® probe was used for detection. TAQMAN® fluorescence was measured using an ABI Prism 7700 Sequence Detection System or ABI7900HT Sequence Detection System (Applied Biosystems, Foster City, Calif.). Expression of transgenes of the present invention was quantitated relative to transgene expression in DBT418 and reported as a ratio of transgene expression to DBT418 expression, i.e., $2^{-(\Delta\Delta C_T)}$ (transgene)/$2^{-(\Delta\Delta C_T)}$(DBT418).

Example 29

Plant Breeding

Backcrossing can be used to improve a starting plant. Backcrossing transfers a specific desirable trait from one source to an inbred or other plant that lacks that trait. This can be accomplished, for example, by first crossing a superior inbred (A) (recurrent parent) to a donor inbred (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent, then the selected progeny are mated back to the superior recurrent parent (A). After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i.e. one or more transformation events.

Therefore, through a series of a breeding manipulations, a selected transgene may be moved from one line into an entirely different line without the need for further recombinant manipulation. Transgenes are valuable in that they typically behave genetically as any other gene and can be manipulated by breeding techniques in a manner identical to any other corn gene. Therefore, one may produce inbred plants which are true breeding for one or more transgenes. By crossing different inbred plants, one may produce a large number of different hybrids with different combinations of transgenes. In this way, plants may be produced which have the desirable agronomic properties frequently associated with hybrids ("hybrid vigor"), as well as the desirable characteristics imparted by one or more transgene(s).

It is desirable to introgress the genes of the present invention into maize hybrids for characterization of the phenotype conferred by each gene in a transformed plant. The host genotype into which the transgene was introduced, preferably CORN OF GERMPLASM A, is an elite inbred and therefore only limited breeding is necessary in order to produce high yielding maize hybrids. The transformed plant, regenerated from callus is crossed, to the same genotype, e.g., CORN OF GERMPLASM A. The progeny are self pollinated twice and plants homozygous for the transgene are identified. Homozygous transgenic plants are crossed to a testcross parent in order to produce hybrids. The test cross parent is an inbred belonging to a heterotic group which is different from that of the transgenic parent and for which it is known that high yielding hybrids can be generated, for example hybrids are produced from crosses of CORN OF GERMPLASM A to either CORN OF GERMPLASM E or CORN OF GERMPLASM B.

Example 30

Methods of Evaluating Phenotype

Expression of the genes of the present invention leads to various phenotypes as disclosed herein in transformed cells and plants. Phenotypic data is collected during the transformation process in callus as well as during plant regeneration, as well as in plants and progeny. Phenotypic data is collected in transformed callus relating to the morphological appearance as well as growth of the callus, e.g., shooty, rooty, starchy, mucoid, non-embryogenic, increased growth rate, decreased growth rate, dead. It is expected that one of skill in the art may recognize other phenotypic characteristics in transformed callus.

Phenotypic data is also collected during the process of plant regeneration as well as in regenerated plants transferred to soil. Phenotypic data includes characteristics such as normal plants, bushy plants, narrow leaves, striped leaves, knotted phenotype, chlorosis, albino, anthocyanin production, buggy whipped (a phenomenon known to the art in which the most recently emerged leaves are elongated and wrap around each other), or altered tassels, ears or roots. It is expected that one of skill in the art may recognize other phenotypic characteristics in transformed plants.

A wide variety of phenotypes are monitored during the process of plant breeding and testing in both inbred and hybrid plants. For example, in R0 and R1 plants (plants directly regenerated from callus and the direct progeny of those plants), plant type (general morphological characteristics such as those described above for plantlets) and nutritional composition of grain produced by the plants are recorded. Nutritional composition analysis may include amino acid composition, amount of protein, starch and oil, characteristics of protein, starch and oil, fiber, ash, mineral content may all be measured. It is expected that one of skill in the art may include analyses of other components of the grain. In R2 and R3 plants, days to pollen shed, days to silking, and plant type are observed. Furthermore, metabolite profiling of R2 plants is conducted. Using methods available to those of skill in the art, 50 to 100 or more metabolites may be analyzed in a plant, thereby establishing a metabolic fingerprint of the plant. In addition in R3 plants, leaf extension rate is measured under field conditions. A variety of phenotypes will be assayed in hybrids comprising a transgene of the present invention. For example, yield, moisture, test weight, nutritional composition, chlorophyll content, leaf temperature, stand, seedling vigor, plant height, leaf number, tillering, brace roots, stay green, stalk lodging, root lodging, plant health, barreness/prolificacy, green snap, pest resistance (including diseases, viruses and insects) and metabolic profiles will be recorded. In addition, phenotypic characteristics of grain harvested from hybrids will be recorded, including number of kernels per row on the ear, number of rows of kernels on the ear, kernel abortion, kernel weight, kernel size, kernel density and physical grain quality. Furthermore, characteristics such as photosynthesis, leaf area, husk structure, kernel dry down rate and internode length may be measured in hybrids or inbreds. It is expected that transcriptional profiling may be performed on transgenic plants expressing genes of the present invention.

In order to determine hybrid yield in transgenic plants expressing genes of the present invention, it is recognized that hybrids must be tested at multiple locations in a geographical location where maize is conventionally grown, e.g., Iowa, Ill. or other locations in the midwestern United States. It is expected that more than one year of yield testing is desirable in order to identify transgenes which contribute to improvement of a maize hybrid. Therefore, transgenic hybrids will be evaluated in a first year at a sufficient number of locations to identify at least an approximately 10% yield difference from a non-transgenic hybrid counterpart. A second year of yield tests is conducted at sufficient locations and with sufficient repetitions to be able to identify a 4-5% yield difference between two hybrids. Furthermore, in the second year of yield tests, hybrids will be evaluated under normal field conditions as well as under stress conditions, e.g., under conditions of water or population density stress. One of skill in the art knows how to design a yield trial such that a statistically significant yield difference can be detected between two hybrids at the desired rate of precision.

Example 31

Surface Sterilization and Imbibition of Corn Seeds

For each transgenic lot, surface sterilize about 50 corn seeds by putting them in a sterile 500 ml Erlenmyer flask with 50 ml of 30% bleach (sodium hypochlorite solution=Chlorox or equivalent) solution containing 0.01% triton X-100 and rotating the flask on an orbital shaker for 5 minutes. Then pour off the bleach solution and wash with about 100 ml of sterile deionized water and pour off the water wash. Repeat the sterile water wash 4 more times, leaving the last water wash on the seeds. Incubate the seeds in this water at room temperature for 24 h for imbibition under air bubbling (pass through 0.2 μm filter).

I. Preparation of Media in Phytotrays.

Prepare water—agar media for several Phytotrays. We are using Phytotray II (or plastic box: 60×30×15 cm) in the inverted position so that the larger depth side of the vessel is on the bottom and the smaller side is used as the lid. Prepare enough water—agar media for 100 ml per Phytotray by autoclaving 0.3% BactoAgar in deionized water for 45 minutes on the liquid cycle. Cool the media to the extent it can be handled easily and pour approximately 100 ml per Phytotray while still molten.

II. Corn Cold Seedling Vigor Assay.

When the media has solidified, bring it and the sterile seeds to a laminar flow hood.

Using sterile forceps, select 20 healthy, most uniform seeds and place the seeds in each Phytotray used for the assay, spacing the seeds evenly so that any individuals can be easily removed later.

Place seeds so that the embryo side is diagonally inserted downward and the seed is just under the surface of the agar. In this position, the emerging shoot and root will be able to directly elongate without cramping.

Incubate the seeds in the media at 22° C. for one week, or until most of the seeds have extruded radicles and are beginning to emerge from the agar.

Remove all but the 10 most uniformly grown seedlings in a laminar flow hood.

Shift the Phytotrays to a cold plant growth chamber set at 10° C. with 16 hour day cycle and incubate there for 2 weeks.

Shift the Phytotrays back to 22° C. for one week.

Remove seedlings, measure root length and shoot length for every seedling, and measure fresh weight g/3 seedlings record in notebook.

Adaptation for cold germination and emergence assay.

Same as above with the following exceptions:

After the last water wash in I., place the flasks at 10° C. during the overnight imbibition step. Also prechill the Phytotrays with solidified media at 10° C.

After seeding the chilled Phytotrays with cold imbibed seeds, they are put directly into the 10° C. chamber.

After about 5 days, remove all but the 10 most uniformly germinated seeds, those whose radicles are about the same length. Return Phytotrays to 10° C. chamber for 1-2 weeks. Remove seedlings, measure root length and shoot length for every seedling, and measure fresh weight from every 3 seedlings, record in notebook.

Shift the 2$^{nd}$ set Phytotrays to 22° C. for 1 week.

Remove seedlings, measure root length and shoot length for every seedling, record in notebook.

Example 32

Creation of Plasmids for Transformation of Soybean

Example

Figure 3:
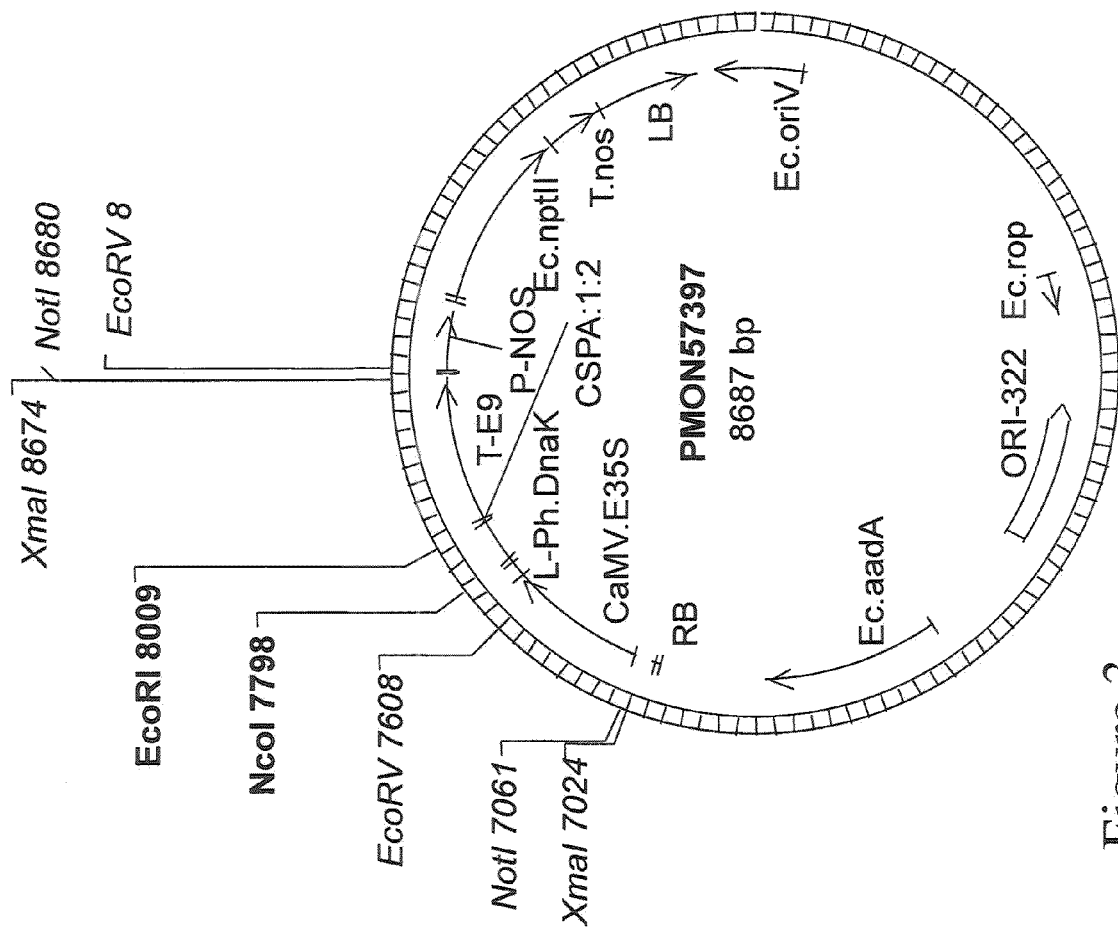
FIG. 3 shows a plasmid map of pMON57397.
Figure 18:
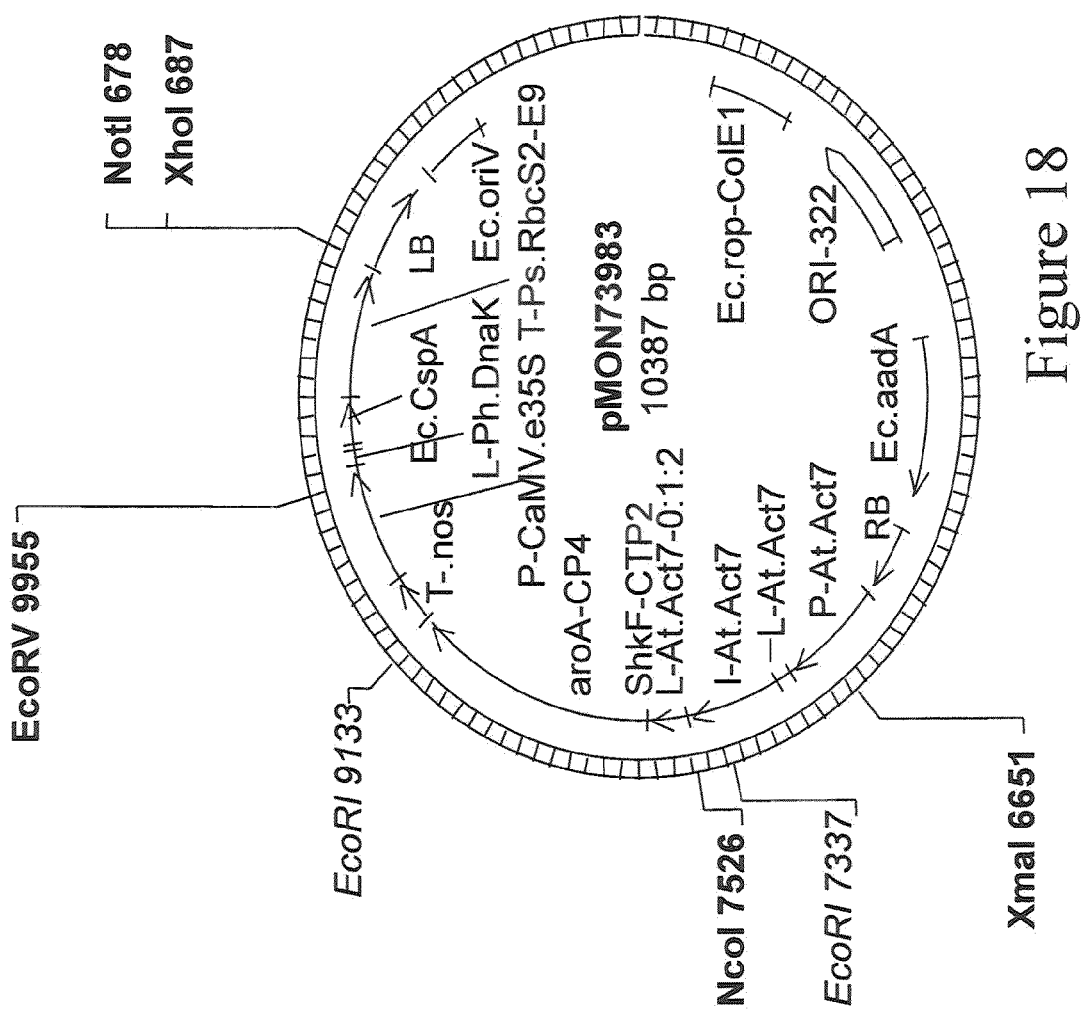
FIG. 18 shows a plasmid map of pMON73983.
Figure 19:
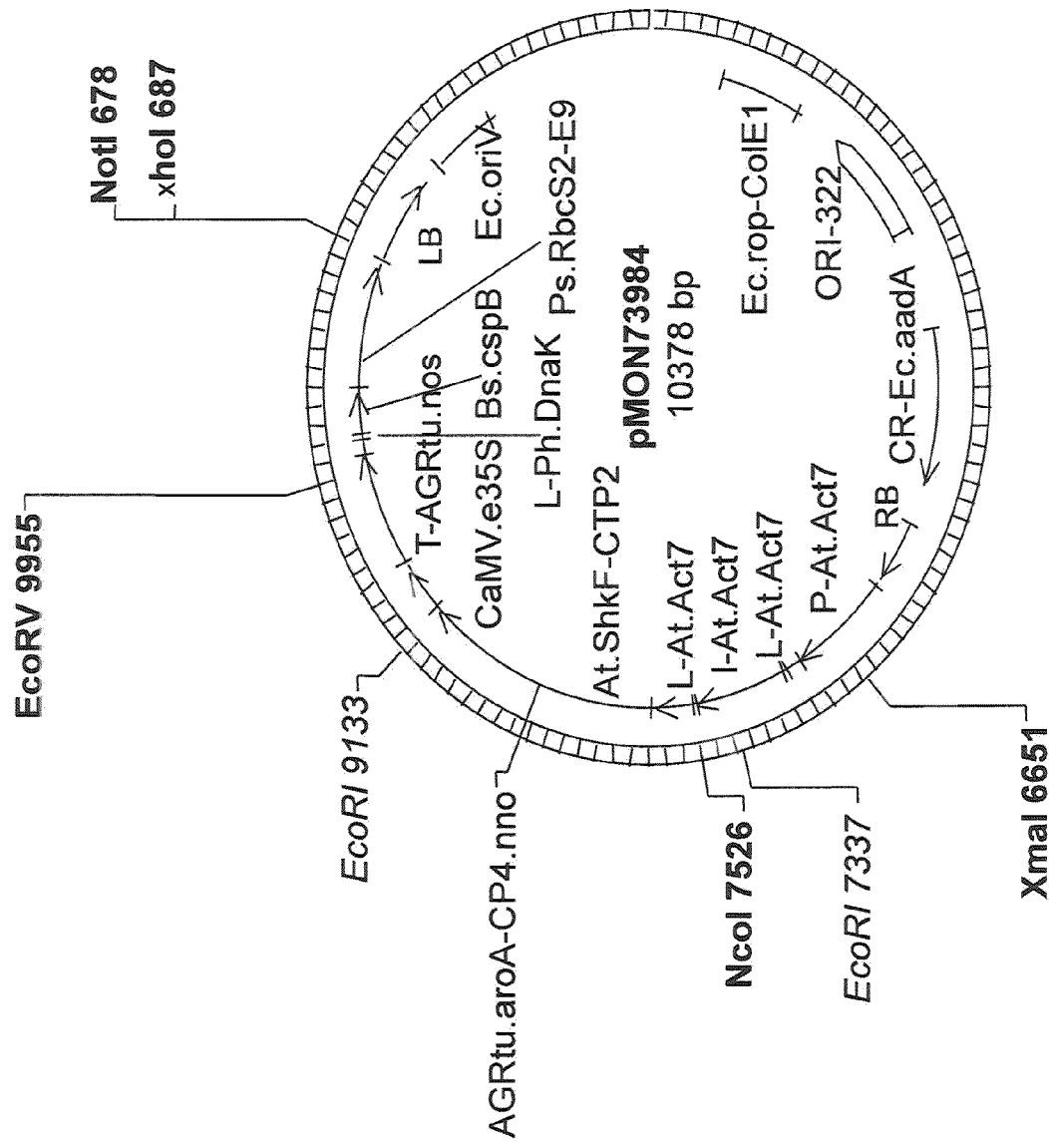
FIG. 19 shows a plasmid map of pMON73984.

For CspA and B Constructs—pMON73983 and 73984 pMON73983 (FIG. 18) is a binary vector for *Agrobacterium*-mediated transformation and constitutive expression of a protein (SEQ ID NO: 1) like *Bacillus subtilis* CspA in Soybean. To clone the *B. subtilis* CspA gene, two gene-specific primers, MSA452 and MSA453 were designed based on the CspA sequence information (Genbank # M30139) from the National Center for Biotechnology Information, which is part of the National Library of Medicine, in turn part of the National Institutes of Health (NCBI). The sequence for MSA452 is GCGCAGGCCTAGATGTACCATGTCCGG-TAAAATGACTGGTATCGTAAAATGG (SEQ ID NO: 86), which anneals at the translational start site of CspA and introduces StuI and BglII sites at the 5' end, while the sequence of MSA453 is CGCGAATTCGGATCCTTATTA-CAGGCTGGTTACGTTACCAGCTGCC (SEQ ID NO: 87), which anneals at the last codon of CspA and introduces BamHI and EcoRI sites at the end of the primer. The reverse primer MSA453 was designed to match the 3' end of the Genbank gene sequence. The PCR reaction was carried out using primers MSA452 and MSA453, High Fidelity Taq Polymerase (BRL) and pMON57397 (FIG. 3) as the template. This template differs at the 3' end of the gene CspA, from that of the GeneBank sequence. The amplified CspB DNA was purified by gel-electrophoresis and ligated to pCR-XL-TOPO vector (Invitrogen). The ligation reaction was transformed into *E. coli* Top10 cells (Invitrogen) as per manufacturer's protocol. Four transformant colonies were picked and miniprep DNA was prepared using Qiagen Miniprep Kit. The inserts were sequenced using M13-specific Forward and Reverse primers. Clone with the correct sequence was named pMON73981 and used for further subcloning.

PMON73881 DNA was digested with StuI and BamHI to isolate the CspA gene fragment. pMON73980 DNA was digested with StuI and BamHI sequentially, and then purified by Gene Clean II kit. The CspB fragment and this purified vector pMON73980 were ligated and the ligation reaction was electrotransformed into *E. coli* DH10 B cells. The transformants were selected on Spectinomycin containing media. The miniprep DNA was prepared from the trasformants and the DNA was checked for the presence of the insert by using CaMV35S-promoter-specific forward primer. The clone containing this insert was named as pMON73983. A larger DNA prep was made and a series of confirmatory digests were carried out, including BglII, EcoRI, PstI, EcoRI+BamHI, StuI+XhoI. These confirmed the correct cloning.

pMON73984 is a binary vector for *Agrobacterium*-mediated transformation and constitutive expression of a protein (SEQ ID NO: 2) like *Bacillus subtilis* CspB in *Arabidopsis*. To clone the *B. subtilis* CspB gene, two gene-specific primers, MSA454 and MSA455 were designed based on the CspB sequence information (Genbank # X59715) from the National Center for Biotechnology Information, which is part of the National Library of Medicine, in turn part of the National Institutes of Health (NCBI). The sequence for MSA454 is GCGCAGGCCTAGATGTACCATGTTA- GAAGGTAAAGTAAAATGGTTCAACTCTG (SEQ ID NO: 88), which anneals at the translational start site of CspB and introduces StuI and BglII sites at the 5' end, while the sequence of MSA455 is CGCGAATTCGGATCCTTAT-TACGCTTCTTTAGTAACGTTAGCAGCTTGTGG (SEQ ID NO: 89), which anneals at the last codon of CspB and introduces BamHI and EcoRI sites at the end of the primer. The reverse primer MSA455 was designed to match the 3' end of the Genbank gene sequence. The PCR reaction was carried out using primers MSA454 and MSA455, High Fedelity Taq Polymerase (BRL) and pMON57399 as the template. This template differs at the 3' end of the gene CspB, from that of the GeneBank sequence. The amplified CspB DNA was purified by gel-electrophoresis and ligated to pCR-XL-TOPO vector (Invitrogen). The ligation reaction was transformed into E. coli Top10 cells (Invitrogen) as per manufacturer's protocol. Four transformant colonies were picked and miniprep DNA was prepared using Qiagen Miniprep Kit. The inserts were sequenced using M13-specific Forward and Reverse primers. Clone with the correct sequence was named pMON73982 and used for further subcloning.

PMON73882 DNA was digested with StuI and BamHI to isolate the CspB gene fragment. pMON73980 DNA was digested with StuI and BamHI sequentially, and then purified by Gene Clean II kit. The CspB fragment and this purified vector pMON73980 were ligated and the ligation reaction was electrotransformed into E. coli DH10 B cells. The transformants were selected on Spectinomycin containing media. The miniprep DNA was prepared from the trasformants and the DNA was checked for the presence of the insert by using CaMV35S-promoter-specific forward primer. The clone containing this insert was named as pMON73984. A larger DNA prep was made and a series of confirmatory digests were carried out, including BglII, EcoRI, PstI, EcoRI+BamHI, StuI+XhoI. These confirmed that the cloning was correct.

Soybean plants were created, through transformation, with the pMON constructs above stably integrated in their genome.

Example 33

Corn plant transformed with DNA contructs from examples 10 and 11, above, were studied.
Greenhouse
  Two experiments were performed, one testing 10 cspA events and one testing 10 cspB events for drought tolerance.
  24 transgene positive and 24 transgene negative hybrid seedlings from each event were tested (all seeds derived from segregating hybrid ears).
  The test was performed on benches in a greenhouse.
  The treatment consisted of withholding water and monitoring total pot weight of each pot containing a plant. Fully watered pots weigh about 1000 grams each and water was withheld until each pot's weight reached 400 grams, then pots were maintained at that weight during the remainder of the treatment.
  Throughout the treatment, plant height was determined by measuring the distance from the soil surface in the pot to the tip of the "tallest" leaf. From these measurements LER (leaf extension rates) were determined by comparing the heights at the intervals between measurements.
  LER comparisons during the drought were made between transgene negative and transgene positive plants within an event.
  For three of ten events tested, cspA transgenic plants were significantly (p<0.10) improved for LER during the treatment.
  For three of ten events tested, cspB transgenic plants were significantly (p<0.10) improved for LER during the treatment.
Field Efficacy
  Three experiments were performed using hybrid seed, one testing 16 cspB events (CA), one testing 21 cspB events (KS), and one testing 14 cspA events (HI) for drought tolerance during the late vegetative stage of growth.
  For the CA and HI trials, rows containing ~34 plants, segregating for presence of the transgene, were present in six and four replicates, respectively. Segregating rows were derived from segregating ears.
  For KS experimental rows contained ~34 plants; as transgenic and non-transgenic paired rows, with six replicates.
  The treatment consisted of withholding water for approximately ten days during the late vegetative phase of growth (giving a small amount as needed to maintain viable plants). At the end of the ten-day period plants were then well irrigated until harvest.
  Throughout the treatment a number of phenotypes were measured including LER, chlorophyll (by SPAD meter), and photosynthesis rate. Following the treatment additional phenotypes measured included: days to pollen shed and silk emergence, and ear components such as kernels/ear, ears with kernels, kernel weight, and yield.
  Phenotype comparisons were made between transgene positive and negative plants within an event and across the construct.
  In the CA trial, cspB as a construct (across all events for vegetative traits and across the "best" six events for reproductive traits) transgene positive plants were significantly (p<0.10) improved for LER, leaf temperature, and kernels/ear during or following the drought treatment.
  In the CA trial, individual events were significantly (p<0.10) improved for LER, average ear length, kernel mass/ear, stomatal conductance, and days to silking during or following the drought treatment.
  In the KS trial, cspB as a construct (across all events for vegetative traits and across the "best" six events for reproductive traits) transgene positive plants were significantly (p<0.10) improved for LER, kernel bearing ears/row, kernels/ear, kernels/plant, shell weight, and yield.
  In the KS trial, individual events were significantly (p<0.10) improved for LER, photosynthetic rate, stomatal conductance, ears/row, and kernels/plant.
  In the HI trial, three events were significantly (p<0.10) improved for LER (chlorophyll content was the only other phenotype measured in HI)
  Summaries of CA and KS results:
Summary of Field Efficacy Results for cspB-Ks Site
1. The field design, site uniformity, and execution of planting and sampling were all consistent with a high quality experiment capable of generating informative data sets.
2. The water-limited treatment was applied in a manner that resulted in treatment impacts on all phenotypes measured, particularly LER, chlorophyll, and photosynthetic rates.
3. The treatment impacts on vegetative and reproductive phenotypes were sufficient to be statistically real and to allow for transgene-mediated improvements to be observed at statistically significant levels.

4. One or more events were statistically improved in transgene containing plants for LER, chlorophyll, photosynthetic rate, stomatal conductance leaf temperature, days to pollen shed, days to silking, anthesis silking interval, ears/plot, kernels/ear, kernels/plant, shell weight, and estimated yield.
5. Construct level statistical improvement was observed at p<0.10 in the dry treatment for LER, ears/plot, kernels/ear, kernels/plant, shell weight, and estimated yield, and for LER in the wet treatment.

TABLE 20

| Event | Treatment | Improved phenotype | P value |
|---|---|---|---|
| Construct | Dry | LER (T1-T0) | 0.009 |
| | Dry | LER (T2-T0) | 0.009 |
| | Dry | LER (T2-T1) | 0.096 |
| | Dry | Stomatal conductance | 0.150 |
| | Dry | Photosynthesis | 0.141 |
| | Dry | Ears/plot | 0.012 |
| | Dry | Kernels/ear | 0.062 |
| | Dry | Kernels/plant | 0.006 |
| | Dry | Shell weight | 0.009 |
| | Dry | Est. Yield | 0.008 |
| | Wet | LER (T2-T1) | 0.025 |
| | Wet | Chlorophyll (—) | 0.062 |
| | Wet | Ears/plot (—) | 0.185 |
| | Wet | Kernels/ear (—) | 0.121 |
| | Wet | Kernels/plant (—) | 0.083 |
| | Wet | Shell weight (—) | 0.132 |
| | Wet | Est. Yield (—) | 0.101 |
| ZM_M38835 | Dry | LER (T1-T0) | 0.008 |
| | Dry | Photosynthesis | 0.066 |
| | Dry | Stomatal conductance | 0.064 |
| | Dry | Transpiration | 0.126 |
| | Dry | Kernels/plant | 0.160 |
| | Dry | Shell weight | 0.149 |
| | Dry | Yield | 0.153 |
| | Wet | LER (T1-T0) | 0.099 |
| | Wet | LER (T2-T1) (—) | 0.026 |
| ZM_M38737 | Dry | Photosynthesis | 0.108 |

Summary of Field Efficacy Results for cspB-CS Site (Font Change)
1. The field design, site uniformity, and execution of planting and sampling were all consistent with a high quality experiment capable of generating informative data sets.
2. The water-limited treatment was applied in a manner that resulted in treatment impacts on all vegetative phenotypes measured, particularly LER, chlorophyll, and photosynthetic rates, but not on all reproductive phenotypes.
3. The treatment impacts on phenotypes (vegetative) of interest were sufficient to be statistically real and to allow for transgene-mediated improvements to be observed at statistically significant levels.
4. One or more events were statistically improved in transgene containing plants for LER, chlorophyll, photosynthetic rate, stomatal conductance leaf temperature, days to pollen shed, days to silking, anthesis silking interval, kernels/ear, average ear length, and kernel mass/ear.
5. Construct level statistical improvement was observed in the dry treatment for LER, leaf temperature, and days to pollen shed, and for ASI in the wet treatment.

TABLE 21

| Event | Treatment | Improved phenotype | P value |
|---|---|---|---|
| Construct | Dry | LER | 0.009 |
| | Dry | Leaf temperature | 0.027 |
| | Dry | Days to pollen shed | 0.192 |
| | Dry | Kernels/ear | 0.080 |
| | Dry | Kernel mass/ear | 0.197 |
| | Dry | Test Wt (lb/bu) Neg | 0.084 |
| | Wet | LER | 0.157 |
| | Wet | Days to pollen shed | 0.098 |
| | Wet | Ave ear length | 0.091 |
| | Wet | Kernel mass/ear | 0.010 |
| | Wet | Test Wt (lb/bu) Neg | 0.188 |
| ZM_M39583 | Dry | LER | 0.051 |
| | Dry | Kernels/ear | 0.200 |
| | Wet | Ave ear length | 0.058 |
| | Wet | Kernel mass/ear | 0.070 |
| ZM_M39872 | Dry | LER | 0.159 |
| | Wet | Days to silking | 0.024 |
| | Wet | ASI | 0.064 |
| ZM_M40946 | Dry | LER | 0.201 |
| ZM_M38238 | Dry | Days to silking | 0.176 |
| | Dry | Kernels/ear | 0.192 |
| | Wet | LER | 0.151 |
| | Wet | Kernel mass/ear | 0.034 |
| ZM_M38244 | Dry | Stomatal Conductance | 0.092 |
| | Dry | Photosynthesis | 0.132 |
| | Dry | Leaf Temperature | 0.155 |
| ZM_M38230 | Dry | Days to silking | 0.176 |
| ZM_M38721 | Dry | Days to silking | 0.066 |
| | Dry | ASI | 0.109 |
| | Wet | Days to silking | 0.117 |
| ZM_M38714 | Wet | Days to silking | 0.010 |
| | Wet | ASI | 0.025 |
| ZM_M40939 | Dry | ASI | 0.109 |

Many of these events have been subsequently tested for improvements in cold germination efficiency and seedling growth under cold conditions, and have not proved efficacious. Thus, these genes driven by this promoter are unlikely to function in maize for improvement of cold germination or seedling growth under cold conditions, but different promoters driving the same genes, or different cold shock proteins may function in maize to improve these phenotypes.

What is claimed is:

1. A drought tolerant transgenic plant that comprises in its genome a recombinant DNA molecule that expresses a cold shock protein, wherein said cold shock protein comprises the cold shock domain sequence [FY]-G-F-I-x(6,7)-[DER]-[LIVM]-F-x-H-x-[STKR]-x-[LIVMFY] of SEQ ID NO:3, has at least 90% identity across the entire length of the *Bacillus subtilis* CspB protein of SEQ ID NO: 2, and confers resistance to drought.

2. The drought tolerant transgenic plant of claim 1, wherein said cold shock protein has at least 92% identity across the entire length of *Bacillus subtilis* CspB protein (SEQ ID NO: 2).

3. The drought tolerant transgenic plant of claim 1, wherein said cold shock protein has at least 95% identity across the entire length of *Bacillus subtilis* CspB protein (SEQ ID NO: 2).

4. The drought tolerant transgenic plant of claim 1, wherein said transgenic plant is a monocot or a dicot plant.

5. The drought tolerant transgenic plant of claim 1, wherein said transgenic plant is a soybean, corn, canola, rice, cotton, barley, oat, turf grass, alfalfa, or wheat plant.

6. The transgenic plant of claim 1, wherein said plant has an increased yield when compared to a non-transformed plant of the same species when said transgenic plant and said non-transformed plant are grown under drought stress.

7. A transgenic propagule of a drought tolerant transgenic plant that comprises in its genome a recombinant DNA molecule that expresses a cold shock protein, wherein said cold shock protein comprises the cold shock domain sequence [FY]-G-F-I-x(6,7)-[DER]-[LIVM]-F-x-H-x-[STKR]-x-[LIVMFY] of SEQ ID NO:3, has at least 90% identity across the entire length of the *Bacillus subtilis* CspB protein of SEQ ID NO: 2 and confers drought resistance to a transgenic plant comprising said recombinant DNA that is produced from said propagule.

8. The transgenic propagule of claim 7, wherein said propagule is a seed.

9. The transgenic propagule of claim 7, wherein said propagule is a root, shoot, leaf, stem, embryo, or cell.

10. A method of improving drought tolerance in a transgenic progeny plant comprising crossing a plant with a drought tolerant transgenic plant having a recombinant DNA expressing a cold shock protein wherein said cold shock protein comprises a cold shock domain sequence [FY]-G-F-I-x(6,7)-[DER]-[LIVM]-F-x-H-x-[STKR]-x-[LIVMFY] of SEQ ID NO:3, has at least 90% 110% identity across the entire length of the *Bacillus subtilis* CspB protein of SEQ ID NO: 2, and confers resistance to drought, and obtaining a transgenic progeny plant having said recombinant DNA.

11. The method of claim 10, wherein said cold shock protein has at least 92% identity across the entire length of *Bacillus subtilis* CspB protein (SEQ ID NO: 2).

12. The method of claim 10, wherein said transgenic plant is a soybean, corn, canola, rice, cotton, barley, oat, turf grass, alfalfa, or wheat plant.

13. A method of producing a drought tolerant transgenic plant comprising the steps of: a) inserting into the genome of plant cells a recombinant DNA molecule that comprises, in the 5' to 3' direction: (i) a first DNA polynucleotide comprising a promoter that functions in plants and which is operably linked to (ii) a second DNA polynucleotide that encodes a cold shock protein that comprises a cold shock domain sequence [FY]-G-F-I-x(6,7)-[DER]-[LIVM]-F-x-H-x-[STKR]-x-[LIVMFY] of SEQ ID NO:3, has at least 90% identity across the entire length of *Bacillus subtilis* CspB protein (SEQ ID NO: 2), and which is operably linked to (iii) a 3' transcription termination DNA polynucleotide that functions as a polyadenylation sequence; b) obtaining transformed plant cells containing said recombinant DNA; c) regenerating transgenic plants from said plant cells; and d) selecting a transgenic plant having increased drought tolerance.

14. The method of claim 13, wherein said cold shock protein has at least 92% identity across the entire length of *Bacillus subtilis* CspB protein (SEQ ID NO: 2).

15. The method of claim 13, wherein said cold shock protein has at least 95% identity across the entire length of *Bacillus subtilis* CspB protein (SEQ ID NO: 2).

16. The method of claim 13, wherein said transgenic plant is a monocot or a dicot plant.

17. The method of claim 13, wherein said transgenic plant is a soybean, corn, canola, rice, cotton, barley, oat, turf grass, alfalfa, or wheat plant.

18. The method of claim 13, wherein said transgenic plant has an increased yield when compared to a non-transformed plant of the same species and when said transgenic plant and said non-transformed plant are grown under drought stress.

19. A method for increasing yield in a crop subject to water deficit during its growth, said method comprising planting seeds having a recombinant DNA expressing a cold shock protein, wherein said cold shock protein comprises the cold shock domain sequence [FY]-G-F-I-x(6,7)-[DER]-[LIVM]-x-H-x-[STKR]-x-[LIVMFY] of SEQ ID NO:3, has at least 90% identity across the entire length of the *Bacillus subtilis* CspB protein of SEQ ID NO: 2 and confers resistance to drought, and allowing said seeds to grow to mature plants under drought conditions.

20. The transgenic propagule of claim 7, wherein said cold shock protein has at least 92% identity across the entire length of *Bacillus subtilis* CspB protein (SEQ ID NO: 2).

21. The transgenic propagule of claim 7, wherein said cold shock protein has at least 95% identity across the entire length of *Bacillus subtilis* CspB protein (SEQ ID NO: 2).

22. The method of claim 19, wherein said cold shock protein has at least 95% identity across the entire length of *Bacillus subtilis* CspB protein (SEQ ID NO: 2).

23. The method of claim 19, wherein said plants are soybean, corn, canola, rice, cotton, barley, oat, turf grass, alfalfa, or wheat plants.

24. The transgenic propagule of claim 7, wherein said plant propagule is a soybean, corn, canola, rice, cotton, barley, oat, turf grass, alfalfa, or wheat plant propagule.

25. The transgenic propagule of claim 23, wherein said plant propagule is a soybean, corn, or rice plant propagule.

26. A drought tolerant transgenic plant that comprises in its genome a recombinant DNA molecule that expresses a cold shock protein, wherein said cold shock protein comprises the cold shock domain sequence [FY]-G-F-I-x(6,7)-[DER]-[LIVM]-F-x-H-x-[STKR]-x-[LIVMFY] of SEQ ID NO:3, has at least 90% identity across the entire length of the *Bacillus subtilis* CspB protein of SEQ ID NO: 2, and confers resistance to drought, and wherein said transgenic plant is a soybean, corn, or rice plant.

27. A method of producing a drought tolerant transgenic plant comprising the steps of a) inserting into the genome of plant cells a recombinant DNA molecule that comprises, in the 5' to 3' direction: (i) a first DNA polynucleotide comprising a promoter that functions in plants and which is operably linked to (ii) a second DNA polynucleotide that encodes a cold shock protein that comprises a cold shock domain sequence [FY]-G-F-I-x(6,7)-[DER]-[LIVM]-F-x-H-x-[STKR]-x-[LIVMFY] of SEQ ID NO:3, has at least 90% identity across the entire length of *Bacillus subtilis* CspB protein (SEQ ID NO: 2), and which is operably linked to (iii) a 3' transcription termination DNA polynucleotide that functions as a polyadenylation sequence; b) obtaining transformed plant cells containing said recombinant DNA; c) regenerating transgenic plants from said plant cells; and d) selecting a transgenic plant having increased drought tolerance, wherein said plant is a soybean, corn, or rice plant.

28. A method for increasing yield in a crop subject to water deficit during its growth, said method comprising planting seeds having a recombinant DNA expressing a cold shock protein, wherein said cold shock protein comprises the cold shock domain sequence [FY]-G-F-I-x(6,7)-[DER]-[LIVM]-F-x-H-x-[STKR]-x-[LIVMFY] of SEQ ID NO:3, has at least 90% identity across the entire length of the *Bacillus subtilis* CspB protein of SEQ ID NO: 2 and confers resistance to drought, and allowing said seeds to grow to mature plants under drought conditions, wherein said plants are soybean, corn, or rice plants.

* * * * *

UNITED STATES PATENT AND TRADEMARK OFFICE
CERTIFICATE OF CORRECTION

PATENT NO. : 8,735,657 B2  
APPLICATION NO. : 12/821846  
DATED : May 27, 2014  
INVENTOR(S) : Mary Fernandes Page 1 of 1

It is certified that error appears in the above-identified patent and that said Letters Patent is hereby corrected as shown below:

In the Claims

Column 143, Claim 10, the text that reads "A method of improving drought tolerance in a transgenic progeny plant comprising crossing a plant with a drought tolerant transgenic plant having a recombinant DNA expressing a cold shock protein wherein said cold shock protein comprises a cold shock domain sequence [FY]-G-F-I-x(6,7)-[DER]-[LIVM]-F-x-H-x-[STKR]-x-[LIVMFY] of SEQ ID NO:3, has at least 90% 110% identity across the entire length of the Bacillus subtilis CspB protein of SEQ ID NO: 2, and confers resistance to drought, and obtaining a transgenic progeny plant having said recombinant DNA." should be deleted and replaced with the following text that reads --A method of improving drought tolerance in a transgenic progeny plant comprising crossing a plant with a drought tolerant transgenic plant having a recombinant DNA expressing a cold shock protein wherein said cold shock protein comprises a cold shock domain sequence [FY]-G-F-I-x(6,7)-[DER]-[LIVM]-F-x-H-x-[STKR)-x-[LIVMFY] of SEQ ID NO:3, has at least 90% identity across the entire length of the Bacillus subtilis CspB protein of SEQ ID NO: 2, and confers resistance to drought, and obtaining a transgenic progeny plant having said recombinant DNA.--

Column 144, Claim 19, the text that reads "A method for increasing yield in a crop subject to water deficit during its growth, said method comprising planting seeds having a recombinant DNA expressing a cold shock protein, wherein said cold shock protein comprises the cold shock domain sequence [FY]-G-F-I-x (6,7)-[DER]-[LIVM]-x-H-x-[STKR]-x-[LIVMFY] of SEQ ID NO:3, has at least 90% identity across the entire length of the Bacillus subtilis CspB protein of SEQ ID NO: 2 and confers resistance to drought, and allowing said seeds to grow to mature plants under drought conditions." should be deleted and replaced with the following text that reads --A method for increasing yield in a crop subject to water deficit during its growth, said method comprising planting seeds having a recombinant DNA expressing a cold shock protein, wherein said cold shock protein comprises the cold shock domain sequence [FY]-G-F-I-x(6,7)-[DER]-[LIVM]F-x-H-x-[STKR]-x-[LIVMFY] of SEQ ID NO:3, has at least 90% identity across the entire length of the Bacillus subtilis CspB protein of SEQ ID NO: 2 and confers resistance to drought, and allowing said seeds to grow to mature plants under drought conditions.--

Signed and Sealed this  
Tenth Day of March, 2015

Michelle K. Lee  
*Deputy Director of the United States Patent and Trademark Office*

SEQUENCE LISTING

```
<160> NUMBER OF SEQ ID NOS: 95

<210> SEQ ID NO 1
<211> LENGTH: 70
<212> TYPE: PRT
<213> ORGANISM: Escherichia coli
<300> PUBLICATION INFORMATION:
<301> AUTHORS: Goldstein, et al
<302> TITLE: Major cold shock protein of Escherichia coli
<303> JOURNAL: Proceedings of the National Academy of Sciences (USA)
<304> VOLUME: 87
<305> ISSUE: 1
```

```
<306> PAGES: 283-287
<307> DATE: 1990-01-01
<308> DATABASE ACCESSION NUMBER: M30139
<309> DATABASE ENTRY DATE: 1993-10-20
<313> RELEVANT RESIDUES IN SEQ ID NO: (1)..(70)

<400> SEQUENCE: 1

Met Ser Gly Lys Met Thr Gly Ile Val Lys Trp Phe Asn Ala Asp Lys
1               5                   10                  15

Gly Phe Gly Phe Ile Thr Pro Asp Asp Gly Ser Lys Asp Val Phe Val
                20                  25                  30

His Phe Ser Ala Ile Gln Asn Asp Gly Tyr Lys Ser Leu Asp Glu Gly
            35                  40                  45

Gln Lys Val Ser Phe Thr Ile Glu Ser Gly Ala Lys Gly Pro Ala Ala
        50                  55                  60

Gly Asn Val Thr Ser Leu
65              70

<210> SEQ ID NO 2
<211> LENGTH: 67
<212> TYPE: PRT
<213> ORGANISM: Bacillus subtilis
<300> PUBLICATION INFORMATION:
<308> DATABASE ACCESSION NUMBER: X59715
<309> DATABASE ENTRY DATE: 1996-03-29
<313> RELEVANT RESIDUES IN SEQ ID NO: (1)..(67)

<400> SEQUENCE: 2

Met Leu Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65

<210> SEQ ID NO 3
<211> LENGTH: 20
<212> TYPE: PRT
<213> ORGANISM: Artificial sequence
<220> FEATURE:
<223> OTHER INFORMATION: Prosite motif PS00352
<220> FEATURE:
<221> NAME/KEY: MISC_FEATURE
<222> LOCATION: (1)..(1)
<223> OTHER INFORMATION: Xaa is phe or tyr
<220> FEATURE:
<221> NAME/KEY: MISC_FEATURE
<222> LOCATION: (5)..(11)
<223> OTHER INFORMATION: Xaa is any amino acid and (11) may or may not
     be present
<220> FEATURE:
<221> NAME/KEY: MISC_FEATURE
<222> LOCATION: (12)..(12)
<223> OTHER INFORMATION: Xaa is asp, glu, or arg
<220> FEATURE:
<221> NAME/KEY: MISC_FEATURE
<222> LOCATION: (13)..(13)
<223> OTHER INFORMATION: Xaa is leu, ile, val, or met
<220> FEATURE:
<221> NAME/KEY: MISC_FEATURE
<222> LOCATION: (15)..(15)
<223> OTHER INFORMATION: Xaa is any amino acid
<220> FEATURE:
<221> NAME/KEY: MISC_FEATURE
```

-continued

```
<222> LOCATION: (17)..(17)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is ser, thr, lys, or arg
<220> FEATURE:
<221> NAME/KEY: MISC_FEATURE
<222> LOCATION: (19)..(19)
<223> OTHER INFORMATION: Xaa is any amino acid
<220> FEATURE:
<221> NAME/KEY: MISC_FEATURE
<222> LOCATION: (20)..(20)
<223> OTHER INFORMATION: Xaa is leu, ile, val, met, phe, or tyr

<400> SEQUENCE: 3

Xaa Gly Phe Ile Xaa Xaa Xaa Xaa Xaa Xaa Xaa Xaa Phe Xaa His
1               5                   10                  15

Xaa Xaa Xaa Xaa
            20

<210> SEQ ID NO 4
<211> LENGTH: 545
<212> TYPE: DNA
<213> ORGANISM: Glycine max
<220> FEATURE:
<221> NAME/KEY: CDS
<222> LOCATION: (61)..(354)

<400> SEQUENCE: 4
attcggctcg aggaccttag aaagagaagg aaaaaaaaaa cttgtgtttc ttgggaagcc      60 atg agc acc acc gag agt caa aga tat aag ggc aca gtg aaa tgg ttc     108
Met Ser Thr Thr Glu Ser Gln Arg Tyr Lys Gly Thr Val Lys Trp Phe
1               5                   10                  15 aac gag gag aag ggt ttc ggt ttc ata act ccc gaa gat ggt ggc tct     156
Asn Glu Glu Lys Gly Phe Gly Phe Ile Thr Pro Glu Asp Gly Gly Ser
                20                  25                  30 gat ctc ttc gtt cac tac agt gcg atc caa acc gac ggc ggc ttc cgc     204
Asp Leu Phe Val His Tyr Ser Ala Ile Gln Thr Asp Gly Gly Phe Arg
            35                  40                  45 acc ttg tcg gag ggt cag tca gta gag ttc ctc gtc act cag gac gac     252
Thr Leu Ser Glu Gly Gln Ser Val Glu Phe Leu Val Thr Gln Asp Asp
        50                  55                  60 agc ggg cga gcc gcg gcc gtc aac gtg acg acc acg gtt aaa tct         300
Ser Gly Arg Ala Ala Ala Val Asn Val Thr Thr Thr Val Lys Ser
65                  70                  75                  80 agt gac agc ggt aac ggg gaa aac tct ggt ggt gat gct gcc aat gtt     348
Ser Asp Ser Gly Asn Gly Glu Asn Ser Gly Gly Asp Ala Ala Asn Val
                85                  90                  95 gag aaa taagtgagaa tgaattattg gagtttcctg aattgcgagt atgatattta       404
Glu Lys tattgatagt tggacaatat actagtccat tggtatttta tattttatta tattatctct    464
ggttattggc atttggttcc aaacttgtaa tacatttatc atgtgtttaa cgtggttatg    524
tagtaagttg ttggatgtgt c                                              545

<210> SEQ ID NO 5
<211> LENGTH: 98
<212> TYPE: PRT
<213> ORGANISM: Glycine max

<400> SEQUENCE: 5

Met Ser Thr Thr Glu Ser Gln Arg Tyr Lys Gly Thr Val Lys Trp Phe
1               5                   10                  15
```

```
Asn Glu Glu Lys Gly Phe Gly Phe Ile Thr Pro Asp Gly Gly Ser
            20                  25                  30

Asp Leu Phe Val His Tyr Ser Ala Ile Gln Thr Asp Gly Gly Phe Arg
        35                  40                  45

Thr Leu Ser Glu Gly Gln Ser Val Glu Phe Leu Val Thr Gln Asp Asp
    50                  55                  60

Ser Gly Arg Ala Ala Val Asn Val Thr Thr Thr Val Lys Ser
65                  70                  75                  80

Ser Asp Ser Gly Asn Gly Glu Asn Ser Gly Gly Asp Ala Ala Asn Val
                85                  90                  95

Glu Lys

<210> SEQ ID NO 6
<211> LENGTH: 255
<212> TYPE: DNA
<213> ORGANISM: Artificial sequence
<220> FEATURE:
<223> OTHER INFORMATION: somewhat similar to E. coli CspA
<220> FEATURE:
<221> NAME/KEY: CDS
<222> LOCATION: (1)..(252)

<400> SEQUENCE: 6 atg gcc ggt aaa atg act ggt atc gta aaa tgg ttc aac gct gac aaa     48
Met Ala Gly Lys Met Thr Gly Ile Val Lys Trp Phe Asn Ala Asp Lys
1               5                   10                  15 ggc ttc ggc ttc atc act cct gac gat ggc tct aaa gat gtg ttc gta    96
Gly Phe Gly Phe Ile Thr Pro Asp Asp Gly Ser Lys Asp Val Phe Val
                20                  25                  30 cac ttc tct gct atc cag aac gat ggt tac aaa tct ctg gac gaa ggt   144
His Phe Ser Ala Ile Gln Asn Asp Gly Tyr Lys Ser Leu Asp Glu Gly
            35                  40                  45 cag aaa gtg tcc ttc acc atc gaa agc ggc gct aaa ggc ccg gca gct   192
Gln Lys Val Ser Phe Thr Ile Glu Ser Gly Ala Lys Gly Pro Ala Ala
        50                  55                  60 ggt aac gta acc agc ctg aat tct cga gcg att aca agg atg atg ata   240
Gly Asn Val Thr Ser Leu Asn Ser Arg Ala Ile Thr Arg Met Met Ile
65                  70                  75                  80 agt aag tcg acc tag                                                255
Ser Lys Ser Thr <210> SEQ ID NO 7
<211> LENGTH: 84
<212> TYPE: PRT
<213> ORGANISM: Artificial sequence
<220> FEATURE:
<223> OTHER INFORMATION: Synthetic Construct

<400> SEQUENCE: 7

Met Ala Gly Lys Met Thr Gly Ile Val Lys Trp Phe Asn Ala Asp Lys
1               5                   10                  15

Gly Phe Gly Phe Ile Thr Pro Asp Asp Gly Ser Lys Asp Val Phe Val
                20                  25                  30

His Phe Ser Ala Ile Gln Asn Asp Gly Tyr Lys Ser Leu Asp Glu Gly
            35                  40                  45

Gln Lys Val Ser Phe Thr Ile Glu Ser Gly Ala Lys Gly Pro Ala Ala
        50                  55                  60

Gly Asn Val Thr Ser Leu Asn Ser Arg Ala Ile Thr Arg Met Met Ile
65                  70                  75                  80

Ser Lys Ser Thr
```

-continued

```
<210> SEQ ID NO 8
<211> LENGTH: 246
<212> TYPE: DNA
<213> ORGANISM: Artificial sequence
<220> FEATURE:
<223> OTHER INFORMATION: Somewhat similar to B. subtilis CspB
<220> FEATURE:
<221> NAME/KEY: CDS
<222> LOCATION: (1)..(243)

<400> SEQUENCE: 8 atg gta gaa ggt aaa gta aaa tgg ttc aac tct gaa aaa ggt ttc gga      48
Met Val Glu Gly Lys Val Lys Trp Phe Asn Ser Glu Lys Gly Phe Gly
1               5                   10                  15 ttc atc gaa gta gaa ggt caa gac gat gta ttc gtt cat ttc tct gct      96
Phe Ile Glu Val Glu Gly Gln Asp Asp Val Phe Val His Phe Ser Ala
            20                  25                  30 att caa ggc gaa ggc ttc aaa act tta gaa gaa ggc caa gct gtt tct     144
Ile Gln Gly Glu Gly Phe Lys Thr Leu Glu Glu Gly Gln Ala Val Ser
        35                  40                  45 ttt gaa atc gtt gaa gga aac cgc gga cca caa gct gct aac gtt act     192
Phe Glu Ile Val Glu Gly Asn Arg Gly Pro Gln Ala Ala Asn Val Thr
    50                  55                  60 aaa gaa gcg aat tct cga gcg att aca agg atg atg ata agt aag tcg     240
Lys Glu Ala Asn Ser Arg Ala Ile Thr Arg Met Met Ile Ser Lys Ser
65                  70                  75                  80 acc tag                                                              246
Thr

<210> SEQ ID NO 9
<211> LENGTH: 81
<212> TYPE: PRT
<213> ORGANISM: Artificial sequence
<220> FEATURE:
<223> OTHER INFORMATION: Synthetic Construct

<400> SEQUENCE: 9

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala Asn Ser Arg Ala Ile Thr Arg Met Met Ile Ser Lys Ser
65                  70                  75                  80

Thr

<210> SEQ ID NO 10
<211> LENGTH: 877
<212> TYPE: DNA
<213> ORGANISM: Escherichia coli
<220> FEATURE:
<221> NAME/KEY: CDS
<222> LOCATION: (528)..(743)
<300> PUBLICATION INFORMATION:
<308> DATABASE ACCESSION NUMBER: L28429
<309> DATABASE ENTRY DATE: 1994-05-04
<313> RELEVANT RESIDUES IN SEQ ID NO: (1)..(877)

<400> SEQUENCE: 10
agctttaata tagctcatga aaggtaaaca ttggcagctg aagggccacg cagaccattt      60
```

```
atccggcaaa attccacgcg taatccggtg gtaatttctt ctgcatcgcg gagattgagc      120
gctgaaacat gaagctggac atcgatacga ccatcggatg gggtgataag acccttgccg      180
cttttgccgt caaaggtttt gacaattcct gtcattttac gggacaaaaa aattccttaa      240
tactgataac ttggcgcact atacacacgt tcctgaagaa agctatagtt ttttgatggg      300
gttgaagatg gctggatgtc taaaataaac attgcttcat atgttcaact atgcgttaat      360
gattgcgtcg gtttgaagaa cagacgtatat acgaagtagt ttactaaagc agttctcatt      420
tcaggtgtta ttcacttatt ccttctttga gtctctccaa ttaagtacga agtcgtttct      480
gttatgcaaa ccatttatgc cgaaaggctc aagttaagga atgtaga atg tca aat      536
                                                     Met Ser Asn
                                                       1 aaa atg act ggt tta gta aaa tgg ttt aac gct gat aaa ggt ttc ggc      584
Lys Met Thr Gly Leu Val Lys Trp Phe Asn Ala Asp Lys Gly Phe Gly
   5              10                  15 ttt att tct cct gtt gat ggt agt aaa gat gtg ttt gtg cat ttt tct      632
Phe Ile Ser Pro Val Asp Gly Ser Lys Asp Val Phe Val His Phe Ser
20              25                  30                  35 gcg att cag aat gat aat tat cga acc tta ttt gaa ggt caa aag gtt      680
Ala Ile Gln Asn Asp Asn Tyr Arg Thr Leu Phe Glu Gly Gln Lys Val
            40                  45                  50 acc ttc tct ata gag agt ggt gct aaa ggt cct gca gca gca aat gtc      728
Thr Phe Ser Ile Glu Ser Gly Ala Lys Gly Pro Ala Ala Ala Asn Val
        55                  60                  65 atc att act gat taa aattcatcgc tcgtctgtat acgataacga agaaggctga      783
Ile Ile Thr Asp
    70 tgcctgagta gagatacgga cagagtagtg aatattggat ctctttaata aaaagtaagg      843 aggtccaata catgaaacaa tggctagcat attt                                 877

<210> SEQ ID NO 11
<211> LENGTH: 71
<212> TYPE: PRT
<213> ORGANISM: Escherichia coli

<400> SEQUENCE: 11

Met Ser Asn Lys Met Thr Gly Leu Val Lys Trp Phe Asn Ala Asp Lys
1               5                   10                  15

Gly Phe Gly Phe Ile Ser Pro Val Asp Gly Ser Lys Asp Val Phe Val
            20                  25                  30

His Phe Ser Ala Ile Gln Asn Asp Asn Tyr Arg Thr Leu Phe Glu Gly
        35                  40                  45

Gln Lys Val Thr Phe Ser Ile Glu Ser Gly Ala Lys Gly Pro Ala Ala
    50                  55                  60

Ala Asn Val Ile Ile Thr Asp
65                  70

<210> SEQ ID NO 12
<211> LENGTH: 1601
<212> TYPE: DNA
<213> ORGANISM: Escherichia coli
<220> FEATURE:
<221> NAME/KEY: CDS
<222> LOCATION: (243)..(452)
<300> PUBLICATION INFORMATION:
<308> DATABASE ACCESSION NUMBER: D28496
<309> DATABASE ENTRY DATE: 1994-02-05
<313> RELEVANT RESIDUES IN SEQ ID NO: (1)..(1601)

<400> SEQUENCE: 12
```

```
gatcgagaca tgtttaaaaa tggcttgcca taattaacgt tgtatgtgat aacagatttc      60
gggttaaacg aggtacagtt ctgtttatgt gtggcatttt cagtaaagaa gtcctgagta     120
aacacgttga cgttgaatac cgcttctctg ccgagcctta tattggtgcc tcatgcagta     180
atgtgtcagt tttatctatg ttatgcctgc gggcgaagaa aacaatctaa ggaatttttc     240 aa atg gca aag att aaa ggt cag gtt aag tgg ttc aac gag tct aaa        287
   Met Ala Lys Ile Lys Gly Gln Val Lys Trp Phe Asn Glu Ser Lys
   1               5                  10                  15 ggt ttt ggc ttc att act ccg gct gat ggc agc aaa gat gtg ttc gta       335
Gly Phe Gly Phe Ile Thr Pro Ala Asp Gly Ser Lys Asp Val Phe Val
                20                  25                  30 cac ttc tcc gct atc cag ggt aat ggc ttc aaa act ctg gct gaa ggt       383
His Phe Ser Ala Ile Gln Gly Asn Gly Phe Lys Thr Leu Ala Glu Gly
            35                  40                  45 cag aac gtt gag ttc gaa att cag gac ggc cag aaa ggt ccg gca gct       431
Gln Asn Val Glu Phe Glu Ile Gln Asp Gly Gln Lys Gly Pro Ala Ala
        50                  55                  60 gtt aac gta aca gct atc tga tcgaatccac tgatctgaag tgtgaatacg          482
Val Asn Val Thr Ala Ile
    65 cttcaatctc gctataaagc ctcgtcgaat gcgaggcttt ttactatgct ttatcttcgc     542 tcctggcgtt cggatatttg cccgccgcgt gattcgcgtt acacttgcgg cctttagtat     602 cctgccggag ttgtcatgtc ttttcctgt ccactttgcc atcagcctct ttcgcgtgaa      662 aaaaacagct atatctgtcc ccagcgacat cagtttgata tggcgaaaga agggtatgtc    722 aatctgctgc ccgttcagca taaacggtct cgtgatccgg gcgacagcgc ggaaatgatg    782 caagcacgcc gcgcattctt agatgccgga cattatcagc cgctgcgtga tgcaattgtc    842 gcccaactga gggaacggct tgatgataag gccacggcgg tgctggatat tggctgtggt    902 gaagggtatt acacacacgc atttgccgat gcgttgcccg aaatcaccac gtttggtctg   962 gatgtttcga aggtagcgat aaaagcggcg gcgaaacgct atccgcaggt cacttttgt    1022 gtcgcttcca gccaccgttt gccgtttttcc gataccagta tggacgccat aatacgtatt   1082 tacgcgccgt gtaaagcaga agaattagca cgagtagtga agcccggcgg ctgggtcatt    1142 actgccacgc cgggaccgcg acatttgatg gagctgaagg gctgattta caatgaagta    1202 catcttcatg cacctcatgc agaacaactg gaaggttta cattacagca gagtgcggag    1262 ttgtgttatc cgatgcgtct tcgcggtgat gaagccgtcg cattattgca gatgacgccg   1322 tttgcctggc gtgcgaagcc agaagtctgg caaacactgg cagcaaaaga agtgttcgac   1382 tgccagacgg actttaatat tcacctctgg cagcgttctt attaaccgtg gaagtgcgtc   1442 cagaggatct ggacgccgat gccgatcagc caggccgcgc gagaattttc cgcttttttc    1502 ccaataattg agccgataaa gcgaccaacc atcatcccta atgtgacat aatcaaggtt    1562 gcacaaccaa tggccaatgc ggtcgcgata atgttgacc                          1601

<210> SEQ ID NO 13
<211> LENGTH: 69
<212> TYPE: PRT
<213> ORGANISM: Escherichia coli

<400> SEQUENCE: 13

Met Ala Lys Ile Lys Gly Gln Val Lys Trp Phe Asn Glu Ser Lys Gly
1               5                   10                  15

Phe Gly Phe Ile Thr Pro Ala Asp Gly Ser Lys Asp Val Phe Val His
                20                  25                  30
```

```
Phe Ser Ala Ile Gln Gly Asn Gly Phe Lys Thr Leu Ala Glu Gly Gln
         35                  40                  45

Asn Val Glu Phe Glu Ile Gln Asp Gly Gln Lys Gly Pro Ala Ala Val
 50                  55                  60

Asn Val Thr Ala Ile
 65

<210> SEQ ID NO 14
<211> LENGTH: 351
<212> TYPE: DNA
<213> ORGANISM: Escherichia coli
<220> FEATURE:
<221> NAME/KEY: CDS
<222> LOCATION: (74)..(298)
<300> PUBLICATION INFORMATION:
<308> DATABASE ACCESSION NUMBER: P24245
<309> DATABASE ENTRY DATE: 1992-03-01
<313> RELEVANT RESIDUES IN SEQ ID NO: (1)..(351)

<400> SEQUENCE: 14
ttttgaacag cccctctct gaccccggtt tattccatct tacttgtata agatttgcga      60
aggatgtcga agc atg gaa aag ggt act gtt aag tgg ttc aac aat gcc       109
            Met Glu Lys Gly Thr Val Lys Trp Phe Asn Asn Ala
             1               5                  10 aaa ggg ttt ggt ttc atc tgc cct gaa ggc ggc ggc gaa gat att ttc      157
Lys Gly Phe Gly Phe Ile Cys Pro Glu Gly Gly Gly Glu Asp Ile Phe
         15                  20                  25 gct cat tat tcc acc att cag atg gat ggt tac aga acg cta aaa gct      205
Ala His Tyr Ser Thr Ile Gln Met Asp Gly Tyr Arg Thr Leu Lys Ala
         30                  35                  40 gga caa tcc gtt cag ttt gat gtc cac cag ggg cca aaa ggc aat cac      253
Gly Gln Ser Val Gln Phe Asp Val His Gln Gly Pro Lys Gly Asn His
 45                  50                  55                  60 gcc agt gtt att gtg ccc gtc gaa gta gaa gcg gca gtc gca tag          298
Ala Ser Val Ile Val Pro Val Glu Val Glu Ala Ala Val Ala
                 65                  70 ctcttctgtc tcattgtgta catcctaaag gcaaaatgcc agcccgatcg gct            351

<210> SEQ ID NO 15
<211> LENGTH: 74
<212> TYPE: PRT
<213> ORGANISM: Escherichia coli

<400> SEQUENCE: 15

Met Glu Lys Gly Thr Val Lys Trp Phe Asn Asn Ala Lys Gly Phe Gly
 1               5                  10                  15

Phe Ile Cys Pro Glu Gly Gly Gly Glu Asp Ile Phe Ala His Tyr Ser
             20                  25                  30

Thr Ile Gln Met Asp Gly Tyr Arg Thr Leu Lys Ala Gly Gln Ser Val
         35                  40                  45

Gln Phe Asp Val His Gln Gly Pro Lys Gly Asn His Ala Ser Val Ile
     50                  55                  60

Val Pro Val Glu Val Glu Ala Ala Val Ala
 65                  70

<210> SEQ ID NO 16
<211> LENGTH: 301
<212> TYPE: DNA
<213> ORGANISM: Escherichia coli
<220> FEATURE:
<221> NAME/KEY: CDS
<222> LOCATION: (62)..(259)
<300> PUBLICATION INFORMATION:
```

<308> DATABASE ACCESSION NUMBER: P39819
<309> DATABASE ENTRY DATE: 1995-02-01
<313> RELEVANT RESIDUES IN SEQ ID NO: (1)..(301)

<400> SEQUENCE: 16

```
tcaggaacgt gtgtatagtg cgccaagtta tcagtattaa ggaatttttt tgtcccgtaa     60 a atg aca gga att gtc aaa acc ttt gac ggc aaa agc ggc aag ggt ctt    109
  Met Thr Gly Ile Val Lys Thr Phe Asp Gly Lys Ser Gly Lys Gly Leu
  1               5                  10                  15 atc acc cca tcc gat ggt cgt atc gat gtc cag ctt cat gtt tca gcg    157
Ile Thr Pro Ser Asp Gly Arg Ile Asp Val Gln Leu His Val Ser Ala
             20                  25                  30 ctc aat ctc cgc gat gca gaa gaa att acc acc gga tta cgc gtg gaa    205
Leu Asn Leu Arg Asp Ala Glu Glu Ile Thr Thr Gly Leu Arg Val Glu
         35                  40                  45 ttt tgc cgg ata aat ggt ctg cgt ggc cct tca gct gcc aat gtt tac    253
Phe Cys Arg Ile Asn Gly Leu Arg Gly Pro Ser Ala Ala Asn Val Tyr
     50                  55                  60 ctt tca tgagctatat taaagcttta atttcaggcc ccatcggatc ac              301
Leu Ser
65
```

<210> SEQ ID NO 17
<211> LENGTH: 66
<212> TYPE: PRT
<213> ORGANISM: Escherichia coli

<400> SEQUENCE: 17

```
Met Thr Gly Ile Val Lys Thr Phe Asp Gly Lys Ser Gly Lys Gly Leu
1               5                  10                  15

Ile Thr Pro Ser Asp Gly Arg Ile Asp Val Gln Leu His Val Ser Ala
             20                  25                  30

Leu Asn Leu Arg Asp Ala Glu Glu Ile Thr Thr Gly Leu Arg Val Glu
         35                  40                  45

Phe Cys Arg Ile Asn Gly Leu Arg Gly Pro Ser Ala Ala Asn Val Tyr
     50                  55                  60

Leu Ser
65
```

<210> SEQ ID NO 18
<211> LENGTH: 994
<212> TYPE: DNA
<213> ORGANISM: Escherichia coli
<220> FEATURE:
<221> NAME/KEY: CDS
<222> LOCATION: (560)..(772)
<300> PUBLICATION INFORMATION:
<308> DATABASE ACCESSION NUMBER: D63344
<309> DATABASE ENTRY DATE: 1999-02-13
<313> RELEVANT RESIDUES IN SEQ ID NO: (1)..(994)

<400> SEQUENCE: 18

```
aaatgtatga tgtgactatt cactatccaa taaaccagtc agcttaaaca agcacgtcat     60
attaagagag ataaacattt gccgctgttg gtcctcgcag gccatttacg cggcaaaatt    120
ccacacgtaa tcctggtata agcacttctg cgtcgcgggg agtgaatgcg gaaatatgga    180
cctgaacttc tttacgaccg tcgggggga taatgaatcc tttgccgctt ttgcgatcaa    240
aggttttgac aattcctgtc attttacggg acaaacaaat tccttactga aaatactgcg    300
ctgcactata cggggttaat aaaataaagc cagcgatatt taagaccgcc ggacggctaa    360
aataaaattt gctaatctct aattatcatg cgttaatagc tgcgtcggtt tgaaagacag    420
```

```
acagcataca aagtagttta ctaaagcagt tctcattatc aggcattatc cccttctttt      480
gagtctctct cctgaacact aagtagtttc tgtattaaag ccctgtttgc cgaaaggccc      540
aaaatgaagg aagtaaaat atg tct aat aaa atg act ggt tta gta aaa tgg      592
              Met Ser Asn Lys Met Thr Gly Leu Val Lys Trp
              1               5                  10 ttt aac gca gat aaa ggt ttt ggc ttt atc act cct gat gat ggc agc      640
Phe Asn Ala Asp Lys Gly Phe Gly Phe Ile Thr Pro Asp Asp Gly Ser
            15                  20                  25 aaa gac gtt ttc gtc cat ttc acc gcc atc cag agc aat gaa ttc cgc      688
Lys Asp Val Phe Val His Phe Thr Ala Ile Gln Ser Asn Glu Phe Arg
        30                  35                  40 acg ctg aac gaa aat cag aaa gtt gaa ttt tct att gag cag ggg caa      736
Thr Leu Asn Glu Asn Gln Lys Val Glu Phe Ser Ile Glu Gln Gly Gln
    45                  50                  55 cgt ggc ccc gcg gca gcg aac gtt gtt acg ctc taa ggttgccatt           782
Arg Gly Pro Ala Ala Ala Asn Val Val Thr Leu
60                  65                  70 attactcaac atctccattt ccgctgtcca tgttgtcatg gttcacagta ccgcacatcg      842
gcattcgatg tgacggagcg aaacccttttg gcgctaagtg tatttttgt aaatcgacga      902 tgatcaccttt tgataacgtc gcgctgcaaa tacgcactga ccatgcgcgc tggatttcac    962
aaataatatc aggctcctcg tggagctttt tt                                    994

<210> SEQ ID NO 19
<211> LENGTH: 70
<212> TYPE: PRT
<213> ORGANISM: Escherichia coli

<400> SEQUENCE: 19

Met Ser Asn Lys Met Thr Gly Leu Val Lys Trp Phe Asn Ala Asp Lys
1               5                  10                  15

Gly Phe Gly Phe Ile Thr Pro Asp Asp Gly Ser Lys Asp Val Phe Val
            20                  25                  30

His Phe Thr Ala Ile Gln Ser Asn Glu Phe Arg Thr Leu Asn Glu Asn
        35                  40                  45

Gln Lys Val Glu Phe Ser Ile Glu Gln Gly Gln Arg Gly Pro Ala Ala
    50                  55                  60

Ala Asn Val Val Thr Leu
65                  70

<210> SEQ ID NO 20
<211> LENGTH: 351
<212> TYPE: DNA
<213> ORGANISM: Agrobacterium tumefaciens
<220> FEATURE:
<221> NAME/KEY: CDS
<222> LOCATION: (125)..(334)
<300> PUBLICATION INFORMATION:
<308> DATABASE ACCESSION NUMBER: AAK90623
<309> DATABASE ENTRY DATE: 2001-12-18
<313> RELEVANT RESIDUES IN SEQ ID NO: (1)..(351)

<400> SEQUENCE: 20
catcgaccat tgcttgtgac gtcgttaccg gaacctcgtg ttccccgtcg gatttcctct      60
caaaaatcga tctaatcccg caaggtatcg cgggaaccac aacgattcta aaaggagat     120 cgtt atg aac act ggt act gta aag tgg ttt aac gcc acc aag ggc ttc      169
     Met Asn Thr Gly Thr Val Lys Trp Phe Asn Ala Thr Lys Gly Phe
     1               5                  10                  15 ggc ttc att cag cct gac aac ggc ggc acg gac gtt ttc gtt cac att      217
Gly Phe Ile Gln Pro Asp Asn Gly Gly Thr Asp Val Phe Val His Ile
```

-continued

```
                         20                  25                  30
tct gct gtt gag cgc gct ggc atg cgt tcg ctg aac gac ggc cag aag      265
Ser Ala Val Glu Arg Ala Gly Met Arg Ser Leu Asn Asp Gly Gln Lys
         35                  40                  45 atc agc tat gag atc gtt cag gac cgc cgg tcc gga aaa agc tct gcc      313
Ile Ser Tyr Glu Ile Val Gln Asp Arg Arg Ser Gly Lys Ser Ser Ala
         50                  55                  60 gat aac ctt cag gca gct tga tattcgtcat tttggcc                       351
Asp Asn Leu Gln Ala Ala
     65

<210> SEQ ID NO 21
<211> LENGTH: 69
<212> TYPE: PRT
<213> ORGANISM: Agrobacterium tumefaciens

<400> SEQUENCE: 21

Met Asn Thr Gly Thr Val Lys Trp Phe Asn Ala Thr Lys Gly Phe Gly
1               5                   10                  15

Phe Ile Gln Pro Asp Asn Gly Gly Thr Asp Val Phe Val His Ile Ser
                20                  25                  30

Ala Val Glu Arg Ala Gly Met Arg Ser Leu Asn Asp Gly Gln Lys Ile
            35                  40                  45

Ser Tyr Glu Ile Val Gln Asp Arg Arg Ser Gly Lys Ser Ser Ala Asp
        50                  55                  60

Asn Leu Gln Ala Ala
65

<210> SEQ ID NO 22
<211> LENGTH: 301
<212> TYPE: DNA
<213> ORGANISM: Agrobacterium tumefaciens
<220> FEATURE:
<221> NAME/KEY: CDS
<222> LOCATION: (59)..(262)
<300> PUBLICATION INFORMATION:
<308> DATABASE ACCESSION NUMBER: AAK89225
<309> DATABASE ENTRY DATE: 2001-12-18
<313> RELEVANT RESIDUES IN SEQ ID NO: (1)..(301)

<400> SEQUENCE: 22
cgtaccgatc aatgatcggt attgcgttga ggtgcactca gcaatcaacg aggacaag       58 atg gca act ggc act gta aaa ttc ttc gct cag gac aag ggc ttt ggc      106
Met Ala Thr Gly Thr Val Lys Phe Phe Ala Gln Asp Lys Gly Phe Gly
1               5                   10                  15 ttc att acc cct gac aat ggc ggt cct gac gta ttc gtt cac atc tcg      154
Phe Ile Thr Pro Asp Asn Gly Gly Pro Asp Val Phe Val His Ile Ser
                20                  25                  30 gca gtc ggt ttc ggc ggc tct ctt cag gat ggt cag aag gtg agc tac      202
Ala Val Gly Phe Gly Gly Ser Leu Gln Asp Gly Gln Lys Val Ser Tyr
            35                  40                  45 gag ttg gga caa gac cgc aag acc ggt aaa tcg aaa gcc gag aac gtc      250
Glu Leu Gly Gln Asp Arg Lys Thr Gly Lys Ser Lys Ala Glu Asn Val
        50                  55                  60 act ctc ctt tga tggcagcgcc gcggcccaac gcacgatagc gcgtgagca            301
Thr Leu Leu
65

<210> SEQ ID NO 23
<211> LENGTH: 67
<212> TYPE: PRT
<213> ORGANISM: Agrobacterium tumefaciens
```

<400> SEQUENCE: 23

Met Ala Thr Gly Thr Val Lys Phe Phe Ala Gln Asp Lys Gly Phe Gly
1               5                   10                  15

Phe Ile Thr Pro Asp Asn Gly Gly Pro Asp Val Phe Val His Ile Ser
            20                  25                  30

Ala Val Gly Phe Gly Gly Ser Leu Gln Asp Gly Gln Lys Val Ser Tyr
        35                  40                  45

Glu Leu Gly Gln Asp Arg Lys Thr Gly Lys Ser Lys Ala Glu Asn Val
    50                  55                  60

Thr Leu Leu
65

<210> SEQ ID NO 24
<211> LENGTH: 251
<212> TYPE: DNA
<213> ORGANISM: Agrobacterium tumefaciens
<220> FEATURE:
<221> NAME/KEY: CDS
<222> LOCATION: (27)..(242)
<300> PUBLICATION INFORMATION:
<308> DATABASE ACCESSION NUMBER: AAK87945
<309> DATABASE ENTRY DATE: 2001-12-18
<313> RELEVANT RESIDUES IN SEQ ID NO: (1)..(251)

<400> SEQUENCE: 24
cgggcagagc gaaaaggacc tgatgc atg gcc gaa act ggc acc gta aaa ttc          53
                             Met Ala Glu Thr Gly Thr Val Lys Phe
                             1               5 ttt aat acc gac aaa ggc ttc ggc ttc atc aag cca gac aat ggt ggc         101
Phe Asn Thr Asp Lys Gly Phe Gly Phe Ile Lys Pro Asp Asn Gly Gly
10                  15                  20                  25 gct gat atc ttt gtt cac atc tct gcc gta cag gct tct ggc ctg tcc         149
Ala Asp Ile Phe Val His Ile Ser Ala Val Gln Ala Ser Gly Leu Ser
                30                  35                  40 gga ctt tca gaa aat cag aaa gtg agc ttc gac acg gaa ccg gat cgt         197
Gly Leu Ser Glu Asn Gln Lys Val Ser Phe Asp Thr Glu Pro Asp Arg
            45                  50                  55 cgc ggc aag ggc ccg aag gca gtc aat ctg cag att gct ggc tga             242
Arg Gly Lys Gly Pro Lys Ala Val Asn Leu Gln Ile Ala Gly
        60                  65                  70 ccctaaaac                                                               251

<210> SEQ ID NO 25
<211> LENGTH: 71
<212> TYPE: PRT
<213> ORGANISM: Agrobacterium tumefaciens

<400> SEQUENCE: 25

Met Ala Glu Thr Gly Thr Val Lys Phe Phe Asn Thr Asp Lys Gly Phe
1               5                   10                  15

Gly Phe Ile Lys Pro Asp Asn Gly Gly Ala Asp Ile Phe Val His Ile
            20                  25                  30

Ser Ala Val Gln Ala Ser Gly Leu Ser Gly Leu Ser Glu Asn Gln Lys
        35                  40                  45

Val Ser Phe Asp Thr Glu Pro Asp Arg Arg Gly Lys Gly Pro Lys Ala
    50                  55                  60

Val Asn Leu Gln Ile Ala Gly
65                  70

<210> SEQ ID NO 26
<211> LENGTH: 651

-continued

```
<212> TYPE: DNA
<213> ORGANISM: Agrobacterium tumefaciens
<220> FEATURE:
<221> NAME/KEY: CDS
<222> LOCATION: (297)..(605)
<300> PUBLICATION INFORMATION:
<308> DATABASE ACCESSION NUMBER: AAK87573
<309> DATABASE ENTRY DATE: 2001-12-18
<313> RELEVANT RESIDUES IN SEQ ID NO: (1)..(651)

<400> SEQUENCE: 26
gcgcgtaatc gaggggttgg caggatatgg ctgataggat gtcatcgaaa acgatagtcg      60
atgtcgagga cctttcgggc gatgccgtcg acctgaccga aatcaccggc gtcgtgaaat     120
ggttcgacgt cgccaagggt ttcggcttca tcgtgcccga taacggtaca caggatgtgc     180
tgctgcacgt ctcgtgcctg cgccgcgacg gctaccagac catccttgaa ggcacgcgca     240
tcgtcgccct catccagcgg cgcgaccgcg gtttccaggt tttccgcatc ctgtcc atg     299
                                                                 Met
                                                                  1 gat cag tcg acc gcc gtt cac ccg tcg cag ctg ccg ccg gtg cgc acc      347
Asp Gln Ser Thr Ala Val His Pro Ser Gln Leu Pro Pro Val Arg Thr
              5                  10                  15 cat gtg cag gtg acg ccg cat agc ggg ctt gag cgt gcc atc gtc aag      395
His Val Gln Val Thr Pro His Ser Gly Leu Glu Arg Ala Ile Val Lys
         20                  25                  30 tgg ttc aac cgc acc aag ggt ttc ggt ttc ctg acg cgt ggc gaa gga      443
Trp Phe Asn Arg Thr Lys Gly Phe Gly Phe Leu Thr Arg Gly Glu Gly
 35                  40                  45 acg gaa gat att ttc gtg cat atg gaa acg ctg cgc cgt ttc ggc ctg      491
Thr Glu Asp Ile Phe Val His Met Glu Thr Leu Arg Arg Phe Gly Leu
50                  55                  60                  65 acg gaa ctg cgc ccc ggc cag gtg gtg ctc gtg cgt tac ggc gat ggc      539
Thr Glu Leu Arg Pro Gly Gln Val Val Leu Val Arg Tyr Gly Asp Gly
                 70                  75                  80 gac aag ggc ctg atg gca gcg gaa atc cat ccc gat aac ccg gtt tcc      587
Asp Lys Gly Leu Met Ala Ala Glu Ile His Pro Asp Asn Pro Val Ser
             85                  90                  95 atc ggg atg tcg cat tga tgtccggcct gcgtcccatg ctgaaaggcg            635
Ile Gly Met Ser His
         100 ccgtcatggc gcttgt                                                     651

<210> SEQ ID NO 27
<211> LENGTH: 102
<212> TYPE: PRT
<213> ORGANISM: Agrobacterium tumefaciens

<400> SEQUENCE: 27

Met Asp Gln Ser Thr Ala Val His Pro Ser Gln Leu Pro Pro Val Arg
 1               5                  10                  15

Thr His Val Gln Val Thr Pro His Ser Gly Leu Glu Arg Ala Ile Val
             20                  25                  30

Lys Trp Phe Asn Arg Thr Lys Gly Phe Gly Phe Leu Thr Arg Gly Glu
         35                  40                  45

Gly Thr Glu Asp Ile Phe Val His Met Glu Thr Leu Arg Arg Phe Gly
     50                  55                  60

Leu Thr Glu Leu Arg Pro Gly Gln Val Val Leu Val Arg Tyr Gly Asp
 65                  70                  75                  80

Gly Asp Lys Gly Leu Met Ala Ala Glu Ile His Pro Asp Asn Pro Val
                 85                  90                  95
```

Ser Ile Gly Met Ser His
        100

<210> SEQ ID NO 28
<211> LENGTH: 301
<212> TYPE: DNA
<213> ORGANISM: Synechocystis PCC6803
<220> FEATURE:
<221> NAME/KEY: CDS
<222> LOCATION: (22)..(273)

<400> SEQUENCE: 28

```
ctctggtttt ggagctaatt t atg tcc att tat gtc ggg aac ctt tct tac      51
                        Met Ser Ile Tyr Val Gly Asn Leu Ser Tyr
                         1               5                  10 caa gcc acc gaa gat gac gtt ttg act gtc ttc tcc gag tat ggc act      99
Gln Ala Thr Glu Asp Asp Val Leu Thr Val Phe Ser Glu Tyr Gly Thr
             15                  20                  25 gtt aag cgg gtt caa ctt ccc act gat cgg gag acc ggt cgt atg cgg    147
Val Lys Arg Val Gln Leu Pro Thr Asp Arg Glu Thr Gly Arg Met Arg
         30                  35                  40 ggt ttt ggt ttc gtt gaa atg tct tcc gat aag gaa gaa gat gcc gcc    195
Gly Phe Gly Phe Val Glu Met Ser Ser Asp Lys Glu Glu Asp Ala Ala
     45                  50                  55 att gaa gct ctg gat gga gcc gaa tgg atg ggg cgg gat ctc aaa gtt    243
Ile Glu Ala Leu Asp Gly Ala Glu Trp Met Gly Arg Asp Leu Lys Val
 60                  65                  70 aat aaa gca aga ccg aga acc cct cgt taa gtttttgcct aattacctga      293
Asn Lys Ala Arg Pro Arg Thr Pro Arg
 75                  80 atttaaga                                                            301
```

<210> SEQ ID NO 29
<211> LENGTH: 83
<212> TYPE: PRT
<213> ORGANISM: Synechocystis PCC6803

<400> SEQUENCE: 29

```
Met Ser Ile Tyr Val Gly Asn Leu Ser Tyr Gln Ala Thr Glu Asp Asp
 1               5                  10                  15

Val Leu Thr Val Phe Ser Glu Tyr Gly Thr Val Lys Arg Val Gln Leu
             20                  25                  30

Pro Thr Asp Arg Glu Thr Gly Arg Met Arg Gly Phe Gly Phe Val Glu
         35                  40                  45

Met Ser Ser Asp Lys Glu Glu Asp Ala Ala Ile Glu Ala Leu Asp Gly
     50                  55                  60

Ala Glu Trp Met Gly Arg Asp Leu Lys Val Asn Lys Ala Arg Pro Arg
 65                  70                  75                  80

Thr Pro Arg
```

<210> SEQ ID NO 30
<211> LENGTH: 401
<212> TYPE: DNA
<213> ORGANISM: Synechocystis PCC6803
<220> FEATURE:
<221> NAME/KEY: CDS
<222> LOCATION: (91)..(396)

<400> SEQUENCE: 30

```
tctagtatta acggttttc gcgttttcc attgacaggc atttctccga aatcaccctc      60
tacatatccc tcagttttg gagaaaatcc atg tca att tat gta ggc aac ctg    114
                                 Met Ser Ile Tyr Val Gly Asn Leu
                                  1               5
```

```
tcc tat gac gtt tca gaa gcc gat tta acc gcg gtt ttt gct gaa tac    162
Ser Tyr Asp Val Ser Glu Ala Asp Leu Thr Ala Val Phe Ala Glu Tyr
     10                  15                  20 ggt tcc gta aag cgg gtt cag ctc ccc acc gac cgg gaa act ggt cgc    210
Gly Ser Val Lys Arg Val Gln Leu Pro Thr Asp Arg Glu Thr Gly Arg
 25                  30                  35                  40 atg cgg ggc ttc ggt ttt gtc gag cta gaa gct gac gcc gaa gaa acg    258
Met Arg Gly Phe Gly Phe Val Glu Leu Glu Ala Asp Ala Glu Glu Thr
                 45                  50                  55 gct gcc att gaa gcc cta gac ggt gca gaa tgg atg ggt cgt gac ctt    306
Ala Ala Ile Glu Ala Leu Asp Gly Ala Glu Trp Met Gly Arg Asp Leu
             60                  65                  70 aaa gtt aac aaa gcc aag ccc cgg gaa aat cgc agt ggc ggt ggt tcc    354
Lys Val Asn Lys Ala Lys Pro Arg Glu Asn Arg Ser Gly Gly Gly Ser
 75                  80                  85 ttt ggt ggc ggt cgt aaa agc tat ggt ggt agc cgc tac tag ggctt      401
Phe Gly Gly Gly Arg Lys Ser Tyr Gly Gly Ser Arg Tyr
 90                  95                 100

<210> SEQ ID NO 31
<211> LENGTH: 101
<212> TYPE: PRT
<213> ORGANISM: Synechocystis PCC6803

<400> SEQUENCE: 31

Met Ser Ile Tyr Val Gly Asn Leu Ser Tyr Asp Val Ser Glu Ala Asp
 1               5                  10                  15

Leu Thr Ala Val Phe Ala Glu Tyr Gly Ser Val Lys Arg Val Gln Leu
             20                  25                  30

Pro Thr Asp Arg Glu Thr Gly Arg Met Arg Gly Phe Gly Phe Val Glu
         35                  40                  45

Leu Glu Ala Asp Ala Glu Glu Thr Ala Ala Ile Glu Ala Leu Asp Gly
     50                  55                  60

Ala Glu Trp Met Gly Arg Asp Leu Lys Val Asn Lys Ala Lys Pro Arg
 65                  70                  75                  80

Glu Asn Arg Ser Gly Gly Gly Ser Phe Gly Gly Gly Arg Lys Ser Tyr
                 85                  90                  95

Gly Gly Ser Arg Tyr
            100

<210> SEQ ID NO 32
<211> LENGTH: 951
<212> TYPE: DNA
<213> ORGANISM: Arabidopsis thaliana
<220> FEATURE:
<221> NAME/KEY: CDS
<222> LOCATION: (46)..(654)

<400> SEQUENCE: 32
aaagatttag agaaaaaagt gagttattaa gagattccaa tcaaa atg agc gga gac    57
                                                Met Ser Gly Asp
                                                 1 aac ggc ggt ggt gag agg cgc aaa ggc tcc gtc aag tgg ttt gat acc    105
Asn Gly Gly Gly Glu Arg Arg Lys Gly Ser Val Lys Trp Phe Asp Thr
 5                  10                  15                  20 cag aag ggt ttc ggc ttc atc act cct gac gac ggt ggc gac gat ctc    153
Gln Lys Gly Phe Gly Phe Ile Thr Pro Asp Asp Gly Gly Asp Asp Leu
                 25                  30                  35 ttc gtt cac cag tcc tcc atc aga tct gag ggt ttc cgt agc ctc gct    201
Phe Val His Gln Ser Ser Ile Arg Ser Glu Gly Phe Arg Ser Leu Ala
             40                  45                  50
```

|  |  |  |  |  |  |  |  |  |  |  |  |  |  |  |  |
|---|---|---|---|---|---|---|---|---|---|---|---|---|---|---|---|
| | | | 40 | | | | 45 | | | | 50 | | | | |
| gcc | gaa | gaa | gcc | gta | gag | ttc | gag | gtt | gag | atc | gac | aac | aac | aac | cgt | 249 |
| Ala | Glu | Glu | Ala | Val | Glu | Phe | Glu | Val | Glu | Ile | Asp | Asn | Asn | Asn | Arg |
| | | | 55 | | | | 60 | | | | 65 | | | | |
| ccc | aag | gcc | atc | gat | gtt | tct | gga | ccc | gac | ggc | gct | ccc | gtc | caa | gga | 297 |
| Pro | Lys | Ala | Ile | Asp | Val | Ser | Gly | Pro | Asp | Gly | Ala | Pro | Val | Gln | Gly |
| | 70 | | | | 75 | | | | 80 | | | | | | |
| aac | agc | ggt | ggt | ggt | tca | tct | ggc | gga | cgc | ggc | ggt | ttc | ggt | gga | gga | 345 |
| Asn | Ser | Gly | Gly | Gly | Ser | Ser | Gly | Gly | Arg | Gly | Gly | Phe | Gly | Gly | Gly |
| 85 | | | | | 90 | | | | | 95 | | | | | 100 |
| aga | gga | ggt | gga | cgc | gga | tct | gga | ggt | gga | tac | ggc | ggt | ggc | ggt | ggt | 393 |
| Arg | Gly | Gly | Gly | Arg | Gly | Ser | Gly | Gly | Gly | Tyr | Gly | Gly | Gly | Gly | Gly |
| | | | 105 | | | | 110 | | | | 115 | | | | |
| gga | tac | gga | gga | aga | gga | ggt | ggt | gga | gga | ggc | agc | gac | tgc | tac | | 441 |
| Gly | Tyr | Gly | Gly | Arg | Gly | Gly | Gly | Arg | Gly | Gly | Ser | Asp | Cys | Tyr |
| | | 120 | | | | 125 | | | | 130 | | | | | |
| aag | tgt | ggt | gag | ccc | ggt | cac | atg | gcg | aga | gac | tgt | tct | gaa | ggc | ggt | 489 |
| Lys | Cys | Gly | Glu | Pro | Gly | His | Met | Ala | Arg | Asp | Cys | Ser | Glu | Gly | Gly |
| | 135 | | | | 140 | | | | 145 | | | | | | |
| gga | ggt | tac | gga | gga | ggc | ggc | ggt | ggc | tac | gga | ggt | gga | ggc | gga | tac | 537 |
| Gly | Gly | Tyr | Gly | Gly | Gly | Gly | Gly | Gly | Tyr | Gly | Gly | Gly | Gly | Gly | Tyr |
| 150 | | | | | 155 | | | | | 160 | | | | | |
| ggc | gga | gga | ggt | ggt | ggt | tac | gga | ggt | ggt | ggc | cgt | gga | ggt | ggt | ggc | 585 |
| Gly | Gly | Gly | Gly | Gly | Gly | Tyr | Gly | Gly | Gly | Gly | Arg | Gly | Gly | Gly | Gly |
| 165 | | | | | 170 | | | | | 175 | | | | | 180 |
| ggc | ggg | gga | agc | tgc | tac | agc | tgt | ggc | gag | tcg | gga | cat | ttc | gcc | agg | 633 |
| Gly | Gly | Gly | Ser | Cys | Tyr | Ser | Cys | Gly | Glu | Ser | Gly | His | Phe | Ala | Arg |
| | | | 185 | | | | 190 | | | | 195 | | | | |
| gat | tgc | acc | agc | ggt | gga | cgt | taaaaccaac gccggttacg cggtggagaa | | | | | | | | 684 |
| Asp | Cys | Thr | Ser | Gly | Gly | Arg |
| | | | 200 |

```
gagtgagttg gttatctcac aagtgatcgg ttctttctcc cgccgccttc tatctctcta    744
ttatccactt tttgcttatt atgatggatc tctatctttg ttagttggtt ttttcttgat    804
ggtttcggat taggactctt cttttggttt tgctacttat ggttggtttt atttctggta    864
cttgtgatat gggtgaaatg ctctacttgt tgctctgttt caagtgttca taatatgcga    924
acaaatattc tgggttttgt ttcagtc                                        951
```

```
<210> SEQ ID NO 33
<211> LENGTH: 203
<212> TYPE: PRT
<213> ORGANISM: Arabidopsis thaliana

<400> SEQUENCE: 33
```

| Met | Ser | Gly | Asp | Asn | Gly | Gly | Glu | Arg | Arg | Lys | Gly | Ser | Val | Lys |
|---|---|---|---|---|---|---|---|---|---|---|---|---|---|---|
| 1 | | | | 5 | | | | | 10 | | | | | 15 |

| Trp | Phe | Asp | Thr | Gln | Lys | Gly | Phe | Gly | Phe | Ile | Thr | Pro | Asp | Gly |
|---|---|---|---|---|---|---|---|---|---|---|---|---|---|---|
| | | | 20 | | | | | 25 | | | | | 30 | |

| Gly | Asp | Asp | Leu | Phe | Val | His | Gln | Ser | Ser | Ile | Arg | Ser | Glu | Gly | Phe |
|---|---|---|---|---|---|---|---|---|---|---|---|---|---|---|---|
| | | 35 | | | | | 40 | | | | | 45 | | | |

| Arg | Ser | Leu | Ala | Ala | Glu | Glu | Ala | Val | Glu | Phe | Glu | Val | Glu | Ile | Asp |
|---|---|---|---|---|---|---|---|---|---|---|---|---|---|---|---|
| | 50 | | | | | 55 | | | | | 60 | | | | |

| Asn | Asn | Asn | Arg | Pro | Lys | Ala | Ile | Asp | Val | Ser | Gly | Pro | Asp | Gly | Ala |
|---|---|---|---|---|---|---|---|---|---|---|---|---|---|---|---|
| 65 | | | | | 70 | | | | | 75 | | | | | 80 |

| Pro | Val | Gln | Gly | Asn | Ser | Gly | Gly | Ser | Ser | Gly | Gly | Arg | Gly | Gly |
|---|---|---|---|---|---|---|---|---|---|---|---|---|---|---|
| | | | | 85 | | | | | 90 | | | | | 95 |

| Phe | Gly | Gly | Gly | Arg | Gly | Gly | Gly | Arg | Gly | Ser | Gly | Gly | Gly | Tyr | Gly |
|---|---|---|---|---|---|---|---|---|---|---|---|---|---|---|---|
| | | | 100 | | | | | 105 | | | | | 110 | | |

```
Gly Gly Gly Gly Gly Tyr Gly Arg Gly Gly Arg Gly Gly
            115                 120                 125

Ser Asp Cys Tyr Lys Cys Gly Glu Pro Gly His Met Ala Arg Asp Cys
    130                 135                 140

Ser Glu Gly Gly Gly Tyr Gly Gly Gly Gly Tyr Gly Gly
145                 150                 155                 160

Gly Gly Gly Tyr Gly Gly Gly Gly Tyr Gly Gly Gly Arg
                165                 170                 175

Gly Gly Gly Gly Gly Gly Ser Cys Tyr Ser Cys Gly Glu Ser Gly
                180                 185                 190

His Phe Ala Arg Asp Cys Thr Ser Gly Gly Arg
        195                 200
```

<210> SEQ ID NO 34
<211> LENGTH: 950
<212> TYPE: DNA
<213> ORGANISM: Gossypium hirsutum
<220> FEATURE:
<221> NAME/KEY: CDS
<222> LOCATION: (58)..(618)

<400> SEQUENCE: 34

```
cccacgcgtc cggagactta tttactttag gaattttcta gaaccttctc gaaggca          57 atg gct gag gcg acc agc acc gag aga tcc act ggc aca gtc aaa tgg       105
Met Ala Glu Ala Thr Ser Thr Glu Arg Ser Thr Gly Thr Val Lys Trp
1               5                   10                  15 ttc agc gcc cag aaa tgt ttt ggt ttc ata gct ccc gac gac gga ggc       153
Phe Ser Ala Gln Lys Cys Phe Gly Phe Ile Ala Pro Asp Asp Gly Gly
            20                  25                  30 gac gac ctt ttc gtc cac caa acc tct att ctt tcc caa ggc ttt cgt       201
Asp Asp Leu Phe Val His Gln Thr Ser Ile Leu Ser Gln Gly Phe Arg
        35                  40                  45 aca ctc tcc gat aac caa ccc gtc gag ttc ttc gtt gat gtc ggt gaa       249
Thr Leu Ser Asp Asn Gln Pro Val Glu Phe Phe Val Asp Val Gly Glu
    50                  55                  60 gat ggc cga gct aag gcc gtt gat gta act cct atg cct cga cct cgc       297
Asp Gly Arg Ala Lys Ala Val Asp Val Thr Pro Met Pro Arg Pro Arg
65                  70                  75                  80 cgt cct tcc cgc ggc ggt gga aga gga gga tat ttt ggc ggc aga ggt       345
Arg Pro Ser Arg Gly Gly Gly Arg Gly Gly Tyr Phe Gly Gly Arg Gly
                85                  90                  95 aga gga ggt ggt ggt tac agg aga gga ggt tat ggt ggt ggc ggt ggc       393
Arg Gly Gly Gly Gly Tyr Arg Arg Gly Gly Tyr Gly Gly Gly Gly Gly
            100                 105                 110 ggt ggc gga ggt agt ggc gct tgt tat aat tgt ggg agg acg ggg cat       441
Gly Gly Gly Gly Ser Gly Ala Cys Tyr Asn Cys Gly Arg Thr Gly His
        115                 120                 125 ata gcc agg gat tgt tat caa ggt ggt gga agt gga agt acg aga tac       489
Ile Ala Arg Asp Cys Tyr Gln Gly Gly Gly Ser Gly Ser Thr Arg Tyr
    130                 135                 140 agt ggc ggc cgt gga gat ggt ggt gga aat aga aga tac ggt ggc gat       537
Ser Gly Gly Arg Gly Asp Gly Gly Gly Asn Arg Arg Tyr Gly Gly Asp
145                 150                 155                 160 agc ggt gat gga cga gga gct ggg gga cga tgt ttt aat tgt gga gat       585
Ser Gly Asp Gly Arg Gly Ala Gly Gly Arg Cys Phe Asn Cys Gly Asp
                165                 170                 175 gaa ggc cat ttt gca agg gat tgc cct aac aaa taattcagaa aacaaaaccg     638
Glu Gly His Phe Ala Arg Asp Cys Pro Asn Lys
            180                 185
```

```
gacatttcct ataatatttt gtgagtataa gtttttcttt tacggtgttt tggaaagggg      698
tttatcagca aaagaagaag aaaccggaaa gttgtctatt ctttccgatc aggcttactt      758
ttcccgattc cgattgatct ggtaacatct ttaaaaaaaa ggtccattgt tttgtataat      818
gtgttgtaat tgttgttatt ctcttaattc ttatcgattc ttctttcttt aatcctctat      878
tcttagtctt tgcattgaca gtatgaacgg gcaatcattt gtcttccttg aagcagattt      938
cttttatttt tc                                                         950

<210> SEQ ID NO 35
<211> LENGTH: 187
<212> TYPE: PRT
<213> ORGANISM: Gossypium hirsutum

<400> SEQUENCE: 35

Met Ala Glu Ala Thr Ser Thr Glu Arg Ser Thr Gly Thr Val Lys Trp
1               5                   10                  15

Phe Ser Ala Gln Lys Cys Phe Gly Phe Ile Ala Pro Asp Asp Gly Gly
            20                  25                  30

Asp Asp Leu Phe Val His Gln Thr Ser Ile Leu Ser Gln Gly Phe Arg
        35                  40                  45

Thr Leu Ser Asp Asn Gln Pro Val Glu Phe Phe Val Asp Val Gly Glu
    50                  55                  60

Asp Gly Arg Ala Lys Ala Val Asp Val Thr Pro Met Pro Arg Pro Arg
65                  70                  75                  80

Arg Pro Ser Arg Gly Gly Gly Arg Gly Gly Tyr Phe Gly Gly Arg Gly
                85                  90                  95

Arg Gly Gly Gly Gly Tyr Arg Arg Gly Gly Tyr Gly Gly Gly Gly Gly
            100                 105                 110

Gly Gly Gly Gly Ser Gly Ala Cys Tyr Asn Cys Gly Arg Thr Gly His
        115                 120                 125

Ile Ala Arg Asp Cys Tyr Gln Gly Gly Ser Gly Ser Thr Arg Tyr
    130                 135                 140

Ser Gly Gly Arg Gly Asp Gly Gly Asn Arg Arg Tyr Gly Gly Asp
145                 150                 155                 160

Ser Gly Asp Gly Arg Gly Ala Gly Gly Arg Cys Phe Asn Cys Gly Asp
                165                 170                 175

Glu Gly His Phe Ala Arg Asp Cys Pro Asn Lys
            180                 185

<210> SEQ ID NO 36
<211> LENGTH: 516
<212> TYPE: DNA
<213> ORGANISM: Gossypium hirsutum
<220> FEATURE:
<221> NAME/KEY: CDS
<222> LOCATION: (42)..(377)
<220> FEATURE:
<221> NAME/KEY: misc_feature
<222> LOCATION: (388)..(388)
<223> OTHER INFORMATION: n = A, G, T, or C

<400> SEQUENCE: 36
cggacgcgtg ggttgggatt ttaaagatgg gtgagaatag g atg acc ggc aag gtg      56
                                             Met Thr Gly Lys Val
                                             1               5 aag tgg ttc gat gac caa aag ggt tat ggc ttc ata tcc cct gac gac       104
Lys Trp Phe Asp Asp Gln Lys Gly Tyr Gly Phe Ile Ser Pro Asp Asp
            10                  15                  20 ggc ggc gac gat ttg ttt gtt cac cag tct tcc atc cgt tcc gag ggt       152
```

```
Gly Gly Asp Asp Leu Phe Val His Gln Ser Ser Ile Arg Ser Glu Gly
            25                  30                  35 ttc cgt agc ctt gct gat ggt gaa gag gtc gag tac gtt gtc gag tct    200
Phe Arg Ser Leu Ala Asp Gly Glu Glu Val Glu Tyr Val Val Glu Ser
        40                  45                  50 tct gaa ggt cgc ccc aag gct gtt gag gtc act ggc ccc aac ggc aac    248
Ser Glu Gly Arg Pro Lys Ala Val Glu Val Thr Gly Pro Asn Gly Asn
55                  60                  65 cct gtt cgt gga tca tct aga tcc gga cgc ggc ggc ggt ggt ggc        296
Pro Val Arg Gly Ser Ser Arg Ser Gly Arg Gly Gly Gly Gly Gly
70                  75                  80                  85 ggt tat ggc ggt gga tcc ggt gga tat ggt gga ggg gga agg aga ggc    344
Gly Tyr Gly Gly Gly Ser Gly Gly Tyr Gly Gly Gly Gly Arg Arg Gly
                90                  95                  100 ggt tat ggt gga gga att gga ggg gga ttt tag ttgcaaaatg ngcatgctta  397
Gly Tyr Gly Gly Gly Ile Gly Gly Gly Phe
            105                 110 aaaatattat aagttgtaag cgtgcatgct aatgcagagt gtggttgact atgacgtatc  457
atactgccat actaattaat attattgagt aaaataaaaa acaatgcttt cttgtttcc   516

<210> SEQ ID NO 37
<211> LENGTH: 111
<212> TYPE: PRT
<213> ORGANISM: Gossypium hirsutum

<400> SEQUENCE: 37

Met Thr Gly Lys Val Lys Trp Phe Asp Asp Gln Lys Gly Tyr Gly Phe
1               5                   10                  15

Ile Ser Pro Asp Asp Gly Gly Asp Leu Phe Val His Gln Ser Ser
            20                  25                  30

Ile Arg Ser Glu Gly Phe Arg Ser Leu Ala Asp Gly Glu Glu Val Glu
        35                  40                  45

Tyr Val Val Glu Ser Ser Glu Gly Arg Pro Lys Ala Val Glu Val Thr
    50                  55                  60

Gly Pro Asn Gly Asn Pro Val Arg Gly Ser Ser Arg Ser Gly Arg Gly
65                  70                  75                  80

Gly Gly Gly Gly Gly Gly Tyr Gly Gly Gly Ser Gly Gly Tyr Gly Gly
                85                  90                  95

Gly Gly Arg Arg Gly Gly Tyr Gly Gly Gly Ile Gly Gly Gly Phe
            100                 105                 110

<210> SEQ ID NO 38
<211> LENGTH: 792
<212> TYPE: DNA
<213> ORGANISM: Glycine max
<220> FEATURE:
<221> NAME/KEY: CDS
<222> LOCATION: (17)..(556)

<400> SEQUENCE: 38
aaaaaagagg cgcaag atg agt ggt agg gtt tct ggg aag gtg aag tgg ttc    52
               Met Ser Gly Arg Val Ser Gly Lys Val Lys Trp Phe
               1               5                   10 aac gat cag aag ggg ttt gga ttc ata acc cct gac gat ggc agc gag    100
Asn Asp Gln Lys Gly Phe Gly Phe Ile Thr Pro Asp Asp Gly Ser Glu
        15                  20                  25 gaa ctc ttc gtt cac caa tct cag atc aaa tct gac ggt ttc cga agc    148
Glu Leu Phe Val His Gln Ser Gln Ile Lys Ser Asp Gly Phe Arg Ser
    30                  35                  40 cta gct gaa gga gag tcc gtt gag ttc gct att gaa tct gaa tct gac    196
Leu Ala Glu Gly Glu Ser Val Glu Phe Ala Ile Glu Ser Glu Ser Asp
```

-continued

```
Leu Ala Glu Gly Glu Ser Val Glu Phe Ala Ile Glu Ser Glu Ser Asp
 45                  50                  55                  60 gga cgc gcc aag gct gtt gat gtc act ggc ccc gac ggc gcc agc gtc      244
Gly Arg Ala Lys Ala Val Asp Val Thr Gly Pro Asp Gly Ala Ser Val
                 65                  70                  75 cag gga acc aga cgc ggc ggt gat ggt ggc cga agc tat ggc ggg gga      292
Gln Gly Thr Arg Arg Gly Gly Asp Gly Gly Arg Ser Tyr Gly Gly Gly
             80                  85                  90 cga gga ggt ggc tac ggt ggt ggg cga ggc ggt ggt ggc ggg gct          340
Arg Gly Gly Gly Tyr Gly Gly Gly Arg Gly Gly Gly Gly Gly Ala
         95                 100                 105 tgc tac aac tgc ggt gaa tcg gga cat ctg gct agg gac tgc agc caa      388
Cys Tyr Asn Cys Gly Glu Ser Gly His Leu Ala Arg Asp Cys Ser Gln
    110                 115                 120 gga ggc ggt gga gac agg tac ggc gga ggc ggt ggt ggt ggc agg          436
Gly Gly Gly Gly Asp Arg Tyr Gly Gly Gly Gly Gly Gly Gly Arg
125                 130                 135                 140 tat gga ggc ggt ggc ggc agg tac ggt ggt ggt gga gga ggt ggt          484
Tyr Gly Gly Gly Gly Gly Arg Tyr Gly Gly Gly Gly Gly Gly
                145                 150                 155 ggc ggc gga gga agc tgc tac agc tgt gga gag tct ggg cat ttc gcc      532
Gly Gly Gly Gly Ser Cys Tyr Ser Cys Gly Glu Ser Gly His Phe Ala
                160                 165                 170 aga gat tgc cca tca agt gct cgt tgaaattact gttatggtgg tttatgttat     586
Arg Asp Cys Pro Ser Ser Ala Arg
            175                 180 gcggattgtt ttaagttttt actttaacat gttgtaggga ttttaatggt ttctgtcaaa    646
gctgtggctt cttataagta gatgcgtgag attttctttt tttttggtta tttaaatgaa    706
agtttctgtg ttatcgttac aatctgcaaa caaaatctgt ttggacctac attttgctat    766
aatgaattgg atgattgtta tcggtt                                         792

<210> SEQ ID NO 39
<211> LENGTH: 180
<212> TYPE: PRT
<213> ORGANISM: Glycine max

<400> SEQUENCE: 39

Met Ser Gly Arg Val Ser Gly Lys Val Lys Trp Phe Asn Asp Gln Lys
 1               5                  10                  15

Gly Phe Gly Phe Ile Thr Pro Asp Asp Gly Ser Glu Glu Leu Phe Val
                 20                  25                  30

His Gln Ser Gln Ile Lys Ser Asp Gly Phe Arg Ser Leu Ala Glu Gly
             35                  40                  45

Glu Ser Val Glu Phe Ala Ile Glu Ser Glu Ser Asp Gly Arg Ala Lys
 50                  55                  60

Ala Val Asp Val Thr Gly Pro Asp Gly Ala Ser Val Gln Gly Thr Arg
 65                  70                  75                  80

Arg Gly Gly Asp Gly Gly Arg Ser Tyr Gly Gly Arg Gly Gly Gly
                 85                  90                  95

Tyr Gly Gly Gly Arg Gly Gly Gly Gly Ala Cys Tyr Asn Cys
                100                 105                 110

Gly Glu Ser Gly His Leu Ala Arg Asp Cys Ser Gln Gly Gly Gly Gly
            115                 120                 125

Asp Arg Tyr Gly Gly Gly Gly Gly Gly Arg Tyr Gly Gly Gly
        130                 135                 140

Gly Gly Gly Arg Tyr Gly Gly Gly Gly Gly Gly Gly Gly Gly
145                 150                 155                 160
```

```
Ser Cys Tyr Ser Cys Gly Glu Ser Gly His Phe Ala Arg Asp Cys Pro
                165                 170                 175
Ser Ser Ala Arg
        180

<210> SEQ ID NO 40
<211> LENGTH: 1245
<212> TYPE: DNA
<213> ORGANISM: Zea mays
<220> FEATURE:
<221> NAME/KEY: CDS
<222> LOCATION: (75)..(806)

<400> SEQUENCE: 40
gcgagagacg ggcaggggag aggaaaaaaa aaatctaacc ctagcatccg cagcgctagg        60 gttcggggt tgcg atg gcg gcg gcg gcg aga cag cgg ggg acg gtg aag         110
             Met Ala Ala Ala Ala Arg Gln Arg Gly Thr Val Lys
              1               5                  10 tgg ttc aac gac acc aag ggc ttc ggg ttc atc tcc ccc gag gac ggc        158
Trp Phe Asn Asp Thr Lys Gly Phe Gly Phe Ile Ser Pro Glu Asp Gly
         15                  20                  25 agc gaa gat ctc ttc gtg cac cag tcg tcg atc aag tcg gag ggc ttc        206
Ser Glu Asp Leu Phe Val His Gln Ser Ser Ile Lys Ser Glu Gly Phe
 30                  35                  40 cgc tcg ctc gcg gag ggc gag gag gtg gag ttt tcc gtc tcg gag ggt        254
Arg Ser Leu Ala Glu Gly Glu Glu Val Glu Phe Ser Val Ser Glu Gly
 45                  50                  55                  60 gac gac ggc cgc act aag gcc gtc gac gtg acc ggc ccc gac gga tcc        302
Asp Asp Gly Arg Thr Lys Ala Val Asp Val Thr Gly Pro Asp Gly Ser
                 65                  70                  75 ttc gtc agg ggc gga ggc gga gga gga ggc ggc ggc ggc tac ggc            350
Phe Val Arg Gly Gly Gly Gly Gly Gly Gly Gly Gly Gly Tyr Gly
             80                  85                  90 tcc cgc ggc ggt ggc gga tct ggc ggc ggc ggt cgc agc tac ggt ggt        398
Ser Arg Gly Gly Gly Gly Ser Gly Gly Gly Gly Arg Ser Tyr Gly Gly
         95                 100                 105 agc tgg ggc ggc ggc cgg aga tcc ggc ggc ggg ggc ggt ccc ggc gcg        446
Ser Trp Gly Gly Gly Arg Arg Ser Gly Gly Gly Gly Pro Gly Ala
 110                 115                 120 tgc tac aag tgc ggc gag ccc ggc cac atg gca agg gac tgc cct agc        494
Cys Tyr Lys Cys Gly Glu Pro Gly His Met Ala Arg Asp Cys Pro Ser
125                 130                 135                 140 gcc gac ggc gga ggc ggc tac ggc gga ggc ggc tac gga gga gga ggc        542
Ala Asp Gly Gly Gly Gly Tyr Gly Gly Gly Gly Tyr Gly Gly Gly Gly
                145                 150                 155 ggc ggc ggc ggt ggc tgc ttc aag tgt ggc gag cct ggc cac atg gcc        590
Gly Gly Gly Gly Gly Cys Phe Lys Cys Gly Glu Pro Gly His Met Ala
                    160                 165                 170 agg gac tgc tcc agc ggc ggc ggc ggc tac ggc ggt ggc ggc ggc ggc        638
Arg Asp Cys Ser Ser Gly Gly Gly Gly Tyr Gly Gly Gly Gly Gly Gly
                175                 180                 185 ggt gga ggc ggc tgc tac aac tgc ggc cag gcc ggc cac atg gcc agg        686
Gly Gly Gly Gly Cys Tyr Asn Cys Gly Gln Ala Gly His Met Ala Arg
                190                 195                 200 gac tgc ccc agc ggt ggc ggc ggt gga ggg agg ttc ggc ggc ggc            734
Asp Cys Pro Ser Gly Gly Gly Gly Gly Gly Arg Phe Gly Gly Gly
205                 210                 215                 220 ggc ggg ggt ggc ggc gac cgc tcc tgc tac aac tgc ggc gag gcc ggc        782
Gly Gly Gly Gly Gly Asp Arg Ser Cys Tyr Asn Cys Gly Glu Ala Gly
                    225                 230                 235
```

| | |
|---|---|
| cac atc gcc cgc gac tgc ccc acg tgaggtgtgt ccgcgtccgt ccgtccagcc<br>His Ile Ala Arg Asp Cys Pro Thr<br>240 | 836 |
| agatcagatc ggatcgctcc accacctgct ggtctgatgg cgccgccccc ttctagatct | 896 |
| cgcttaaaaa aacaccccc tctcgctgtg tgtcggagta ccgctttagt tttgccgatc | 956 |
| cgggcacgag tgcccgctgc ctctttcctc tcatgcgtaa aggaacccg tccgccgttt | 1016 |
| tcagatttcg ttcggtccgt agaagaactc tcaagttaag ttaagttatc atggtgtgtg | 1076 |
| cttggtcgtt gttcgtcgtc gtcgttaagg ttttaagaga tgatttggtc ctgtgttgcc | 1136 |
| gaggggaagt cgaatctgct tttttctttt tttgtggttt gttccaccag actgaggaag | 1196 |
| gagatgagat gattattctc ccaaaaaaaa aaaaaaaaa aaaaaaaaa | 1245 |

<210> SEQ ID NO 41
<211> LENGTH: 244
<212> TYPE: PRT
<213> ORGANISM: Zea mays

<400> SEQUENCE: 41

Met Ala Ala Ala Arg Gln Arg Gly Thr Val Lys Trp Phe Asn Asp
1               5                   10                  15

Thr Lys Gly Phe Gly Phe Ile Ser Pro Glu Asp Gly Ser Glu Asp Leu
            20                  25                  30

Phe Val His Gln Ser Ser Ile Lys Ser Glu Gly Phe Arg Ser Leu Ala
        35                  40                  45

Glu Gly Glu Glu Val Glu Phe Ser Val Ser Gly Asp Asp Gly Arg
    50                  55                  60

Thr Lys Ala Val Asp Val Thr Gly Pro Asp Gly Ser Phe Val Arg Gly
65                  70                  75                  80

Gly Gly Gly Gly Gly Gly Gly Gly Tyr Gly Ser Arg Gly Gly
                85                  90                  95

Gly Gly Ser Gly Gly Gly Gly Arg Ser Tyr Gly Gly Ser Trp Gly Gly
            100                 105                 110

Gly Arg Arg Ser Gly Gly Gly Gly Pro Gly Ala Cys Tyr Lys Cys
        115                 120                 125

Gly Glu Pro Gly His Met Ala Arg Asp Cys Pro Ser Ala Asp Gly Gly
    130                 135                 140

Gly Gly Tyr Gly Gly Gly Gly Tyr Gly Gly Gly Gly Gly Gly Gly Gly
145                 150                 155                 160

Gly Cys Phe Lys Cys Gly Glu Pro Gly His Met Ala Arg Asp Cys Ser
                165                 170                 175

Ser Gly Gly Gly Gly Tyr Gly Gly Gly Gly Gly Gly Gly Gly Gly
            180                 185                 190

Cys Tyr Asn Cys Gly Gln Ala Gly His Met Ala Arg Asp Cys Pro Ser
        195                 200                 205

Gly Gly Gly Gly Gly Gly Gly Arg Phe Gly Gly Gly Gly Gly Gly
    210                 215                 220

Gly Asp Arg Ser Cys Tyr Asn Cys Gly Glu Ala Gly His Ile Ala Arg
225                 230                 235                 240

Asp Cys Pro Thr

<210> SEQ ID NO 42
<211> LENGTH: 1409
<212> TYPE: DNA
<213> ORGANISM: Zea mays
<220> FEATURE:
<221> NAME/KEY: CDS -continued

<222> LOCATION: (27)..(995)

<400> SEQUENCE: 42

```
cgcagcgcta gggttcgggg gttgcg atg gcg gcg gcg gcg agg cag cgg ggg      53
                              Met Ala Ala Ala Ala Arg Gln Arg Gly
                              1               5 acg gtg aag tgg ttc aac gac acc aag ggc ttc ggg ttc atc tcc ccc      101
Thr Val Lys Trp Phe Asn Asp Thr Lys Gly Phe Gly Phe Ile Ser Pro
10              15                  20                  25 gag gac ggc agc gag gat ctc ttc gtg cac cag tcg tcg atc aag tcg      149
Glu Asp Gly Ser Glu Asp Leu Phe Val His Gln Ser Ser Ile Lys Ser
            30                  35                  40 gag ggc ttc cgc tcg ctc gcg gag ggc gag gag gtg gag ttt tcc gtc      197
Glu Gly Phe Arg Ser Leu Ala Glu Gly Glu Glu Val Glu Phe Ser Val
        45                  50                  55 tcg gag ggt gac gac ggc cgc act aag gcc gtc gac gtg acc ggc ccc      245
Ser Glu Gly Asp Asp Gly Arg Thr Lys Ala Val Asp Val Thr Gly Pro
    60                  65                  70 gac gga tcc ttc gtc agg ggc ggc gga ggc gga ggc ggc ggc ggc          293
Asp Gly Ser Phe Val Arg Gly Gly Gly Gly Gly Gly Gly Gly Gly
75                  80                  85 ggc ggc tac ggc tcc cgc ggc ggt ggc gga tct ggc ggc ggc ggt cgc      341
Gly Gly Tyr Gly Ser Arg Gly Gly Gly Gly Ser Gly Gly Gly Gly Arg
90                  95                  100                 105 agc tac ggt ggt agc tgg ggc ggc ggc cgg aga tcc gcg ccc gac gcc      389
Ser Tyr Gly Gly Ser Trp Gly Gly Gly Arg Arg Ser Ala Pro Asp Ala
            110                 115                 120 gct ttc ggc tcc gtc ctc tcc ggc acc gcc ggc gac gcc gcc ccc agc      437
Ala Phe Gly Ser Val Leu Ser Gly Thr Ala Gly Asp Ala Ala Pro Ser
        125                 130                 135 gac cag tgg ttc gtc gac gcg ctc aac gcc ccc gcg ccg cac ccc atc      485
Asp Gln Trp Phe Val Asp Ala Leu Asn Ala Pro Ala Pro His Pro Ile
    140                 145                 150 gag cgc gtc cga tcc gag tcc tcc tcg atc gtc tcc gac gtc ccc gac      533
Glu Arg Val Arg Ser Glu Ser Ser Ser Ile Val Ser Asp Val Pro Asp
155                 160                 165 tac ctc ttc agc ctc gac agc ccg tcc gac gac ccc agc ccc ggc ccc      581
Tyr Leu Phe Ser Leu Asp Ser Pro Ser Asp Asp Pro Ser Pro Gly Pro
170                 175                 180                 185 tcg gcg gct cgc gcc aag tcc gac ccc gcg gag act ccg cac cac cac      629
Ser Ala Ala Arg Ala Lys Ser Asp Pro Ala Glu Thr Pro His His His
            190                 195                 200 ggc gac gac gtg ccg cct tcc gct cga cag ata ccg cac gtc gca gga      677
Gly Asp Asp Val Pro Pro Ser Ala Arg Gln Ile Pro His Val Ala Gly
        205                 210                 215 gga gcg tca tcg tgg ccc gcc ccg ccg ccg tac atg gcg cag cct          725
Gly Ala Ser Ser Trp Pro Ala Pro Pro Pro Pro Tyr Met Ala Gln Pro
    220                 225                 230 atg tac tac ttc ccc gtg ccg cca ccg gtc cac tac ctc gac cag tct      773
Met Tyr Tyr Phe Pro Val Pro Pro Pro Val His Tyr Leu Asp Gln Ser
235                 240                 245 gcg cag agt ggc tac atg cct cgc ccg atc tac cac att gtc ggt ggc      821
Ala Gln Ser Gly Tyr Met Pro Arg Pro Ile Tyr His Ile Val Gly Gly
250                 255                 260                 265 gga gga agc gag gcg cct ggc gga gat ctt cac gcg gcc gga gta          869
Gly Gly Ser Glu Ala Pro Gly Gly Asp Leu His Ala Ala Gly Gly Val
            270                 275                 280 tac ggc gtc tcg cac cac atg cag ggg ttc ccg ccg atg atg tac gcg      917
Tyr Gly Val Ser His His Met Gln Gly Phe Pro Pro Met Met Tyr Ala
        285                 290                 295
```

```
ccg ccg cgc gcg gtc atc tac aac tac aag tcg gag ggg atg cca tcg    965
Pro Pro Arg Ala Val Ile Tyr Asn Tyr Lys Ser Glu Gly Met Pro Ser
        300                 305                 310 ctg cct ccg gaa ggt ggg gca cac tct tcc taggtgcatc ggctacttca     1015
Leu Pro Pro Glu Gly Gly Ala His Ser Ser
    315                 320 catctctgaa tcctgattat tgttgcagat gcctaagcta aggagttttg cgtggtaatt  1075
tttttatcga ttcgtctaga gtcttgttcg ttgttttgta tagatggagg ggttgatggt  1135
gatggataga tattaatgca gttttcgtct agtggaaata tattcgtgaa atgtatatca  1195
tactaaatag tatagtattt ggtgtgatta attaatattc tagttaatgt aatgtgggat  1255
tcatataatc taggtggttc tggtcttata gaaaccattt ttgggcattt tatatttaca  1315
taaactggat gttgggtgaa tgttctaagc agtatgtgct gtgttgaacc tcaatcactt  1375
atgagtggtt actaaatttg aatttgatgt cttc                              1409
```

<210> SEQ ID NO 43
<211> LENGTH: 323
<212> TYPE: PRT
<213> ORGANISM: Zea mays

<400> SEQUENCE: 43

```
Met Ala Ala Ala Arg Gln Arg Gly Thr Val Lys Trp Phe Asn Asp
1               5                   10                  15

Thr Lys Gly Phe Gly Phe Ile Ser Pro Glu Asp Gly Ser Glu Asp Leu
                20                  25                  30

Phe Val His Gln Ser Ser Ile Lys Ser Glu Gly Phe Arg Ser Leu Ala
            35                  40                  45

Glu Gly Glu Glu Val Glu Phe Ser Val Ser Gly Asp Asp Gly Arg
    50                  55                  60

Thr Lys Ala Val Asp Val Thr Gly Pro Asp Gly Ser Phe Val Arg Gly
65                  70                  75                  80

Gly Gly Gly Gly Gly Gly Gly Gly Tyr Gly Ser Arg Gly
                    85                  90                  95

Gly Gly Gly Ser Gly Gly Gly Arg Ser Tyr Gly Ser Trp Gly
                100                 105                 110

Gly Gly Arg Arg Ser Ala Pro Asp Ala Ala Phe Gly Ser Val Leu Ser
            115                 120                 125

Gly Thr Ala Gly Asp Ala Ala Pro Ser Asp Gln Trp Phe Val Asp Ala
    130                 135                 140

Leu Asn Ala Pro Ala His Pro Ile Glu Arg Val Arg Ser Glu Ser
145                 150                 155                 160

Ser Ser Ile Val Ser Asp Val Pro Asp Tyr Leu Phe Ser Leu Asp Ser
                165                 170                 175

Pro Ser Asp Asp Pro Ser Pro Gly Pro Ser Ala Ala Arg Ala Lys Ser
            180                 185                 190

Asp Pro Ala Glu Thr Pro His His His Gly Asp Asp Val Pro Pro Ser
    195                 200                 205

Ala Arg Gln Ile Pro His Val Ala Gly Gly Ala Ser Ser Trp Pro Ala
    210                 215                 220

Pro Pro Pro Pro Tyr Met Ala Gln Pro Met Tyr Tyr Phe Pro Val Pro
225                 230                 235                 240

Pro Pro Val His Tyr Leu Asp Gln Ser Ala Gln Ser Gly Tyr Met Pro
                245                 250                 255

Arg Pro Ile Tyr His Ile Val Gly Gly Gly Ser Glu Ala Pro Gly
            260                 265                 270
```

```
Gly Asp Leu His Ala Ala Gly Gly Val Tyr Gly Val Ser His His Met
        275                 280                 285

Gln Gly Phe Pro Pro Met Met Tyr Ala Pro Pro Arg Ala Val Ile Tyr
        290                 295                 300

Asn Tyr Lys Ser Glu Gly Met Pro Ser Leu Pro Pro Glu Gly Gly Ala
305                 310                 315                 320

His Ser Ser

<210> SEQ ID NO 44
<211> LENGTH: 215
<212> TYPE: DNA
<213> ORGANISM: Bacillus subtilis
<220> FEATURE:
<221> NAME/KEY: CDS
<222> LOCATION: (15)..(215)
<300> PUBLICATION INFORMATION:
<308> DATABASE ACCESSION NUMBER: AB001488
<309> DATABASE ENTRY DATE: 1999-02-13
<313> RELEVANT RESIDUES IN SEQ ID NO: (1)..(215)

<400> SEQUENCE: 44
aggaggcaac aaaa atg gaa caa ggt aca gtt aaa tgg ttt aat gca gaa       50
              Met Glu Gln Gly Thr Val Lys Trp Phe Asn Ala Glu
                1               5                  10 aaa ggt ttt ggc ttt atc gaa cgc gaa aat gga gac gat gta ttc gta      98
Lys Gly Phe Gly Phe Ile Glu Arg Glu Asn Gly Asp Asp Val Phe Val
         15                  20                  25 cac ttt tct gca atc caa agt gac gga ttc aaa tct tta gac gaa ggt    146
His Phe Ser Ala Ile Gln Ser Asp Gly Phe Lys Ser Leu Asp Glu Gly
     30                  35                  40 caa aaa gta tcg ttt gac gtt gag caa ggt gct cgt gga gct caa gct    194
Gln Lys Val Ser Phe Asp Val Glu Gln Gly Ala Arg Gly Ala Gln Ala
45                  50                  55                  60 gct aac gtt caa aaa gct taa                                          215
Ala Asn Val Gln Lys Ala
                65

<210> SEQ ID NO 45
<211> LENGTH: 66
<212> TYPE: PRT
<213> ORGANISM: Bacillus subtilis

<400> SEQUENCE: 45

Met Glu Gln Gly Thr Val Lys Trp Phe Asn Ala Glu Lys Gly Phe Gly
1               5                   10                  15

Phe Ile Glu Arg Glu Asn Gly Asp Asp Val Phe Val His Phe Ser Ala
            20                  25                  30

Ile Gln Ser Asp Gly Phe Lys Ser Leu Asp Glu Gly Gln Lys Val Ser
        35                  40                  45

Phe Asp Val Glu Gln Gly Ala Arg Gly Ala Gln Ala Ala Asn Val Gln
    50                  55                  60

Lys Ala
65

<210> SEQ ID NO 46
<211> LENGTH: 201
<212> TYPE: DNA
<213> ORGANISM: Bacillus subtilis
<220> FEATURE:
<221> NAME/KEY: CDS
<222> LOCATION: (1)..(201)
<300> PUBLICATION INFORMATION:
<308> DATABASE ACCESSION NUMBER: L77246
```

```
<309> DATABASE ENTRY DATE: 2001-12-14
<313> RELEVANT RESIDUES IN SEQ ID NO: (1)..(201)

<400> SEQUENCE: 46 atg caa aac ggt aaa gta aaa tgg ttc aac aac gaa aaa gga ttc ggc      48
Met Gln Asn Gly Lys Val Lys Trp Phe Asn Asn Glu Lys Gly Phe Gly
 1               5                  10                  15 ttc att gaa gtt gaa ggc gga gac gat gta ttt gtt cac ttc aca gct      96
Phe Ile Glu Val Glu Gly Gly Asp Asp Val Phe Val His Phe Thr Ala
                20                  25                  30 atc gaa gga gat gga tac aaa tca tta gaa gaa gga caa gaa gtt tct     144
Ile Glu Gly Asp Gly Tyr Lys Ser Leu Glu Glu Gly Gln Glu Val Ser
            35                  40                  45 ttt gaa att gtc gaa ggt aat cgt gga cct caa gct tct aat gtt gta     192
Phe Glu Ile Val Glu Gly Asn Arg Gly Pro Gln Ala Ser Asn Val Val
        50                  55                  60 aaa ctc taa                                                          201
Lys Leu
65

<210> SEQ ID NO 47
<211> LENGTH: 66
<212> TYPE: PRT
<213> ORGANISM: Bacillus subtilis

<400> SEQUENCE: 47

Met Gln Asn Gly Lys Val Lys Trp Phe Asn Asn Glu Lys Gly Phe Gly
 1               5                  10                  15

Phe Ile Glu Val Glu Gly Gly Asp Asp Val Phe Val His Phe Thr Ala
                20                  25                  30

Ile Glu Gly Asp Gly Tyr Lys Ser Leu Glu Glu Gly Gln Glu Val Ser
            35                  40                  45

Phe Glu Ile Val Glu Gly Asn Arg Gly Pro Gln Ala Ser Asn Val Val
        50                  55                  60

Lys Leu
65

<210> SEQ ID NO 48
<211> LENGTH: 198
<212> TYPE: DNA
<213> ORGANISM: Bacillus halodurans
<220> FEATURE:
<221> NAME/KEY: CDS
<222> LOCATION: (1)..(198)
<300> PUBLICATION INFORMATION:
<308> DATABASE ACCESSION NUMBER: AP001519
<309> DATABASE ENTRY DATE: 2001-01-10
<313> RELEVANT RESIDUES IN SEQ ID NO: (1)..(198)

<400> SEQUENCE: 48 atg caa gga aaa gta aaa tgg ttt aac gca gaa aaa ggt ttc ggt ttt      48
Met Gln Gly Lys Val Lys Trp Phe Asn Ala Glu Lys Gly Phe Gly Phe
 1               5                  10                  15 atc gag cgc gaa gat ggt gac gat gta ttt gtt cat ttc tct gcc att      96
Ile Glu Arg Glu Asp Gly Asp Asp Val Phe Val His Phe Ser Ala Ile
                20                  25                  30 aac aca gac ggt ttc aaa aca tta gac gaa ggt caa tct gtt gag ttt     144
Asn Thr Asp Gly Phe Lys Thr Leu Asp Glu Gly Gln Ser Val Glu Phe
            35                  40                  45 gat atc gtt gaa gga gct cgc gga cct caa gct gcg aac gtc act aag     192
Asp Ile Val Glu Gly Ala Arg Gly Pro Gln Ala Ala Asn Val Thr Lys
        50                  55                  60 ctt taa                                                              198
```

Leu
65

<210> SEQ ID NO 49
<211> LENGTH: 65
<212> TYPE: PRT
<213> ORGANISM: Bacillus halodurans

<400> SEQUENCE: 49

Met Gln Gly Lys Val Lys Trp Phe Asn Ala Glu Lys Gly Phe Gly Phe
1               5                   10                  15

Ile Glu Arg Glu Asp Gly Asp Val Phe Val His Phe Ser Ala Ile
            20                  25                  30

Asn Thr Asp Gly Phe Lys Thr Leu Asp Glu Gly Gln Ser Val Glu Phe
                35                  40                  45

Asp Ile Val Glu Gly Ala Arg Gly Pro Gln Ala Ala Asn Val Thr Lys
        50                  55                  60

Leu
65

<210> SEQ ID NO 50
<211> LENGTH: 204
<212> TYPE: DNA
<213> ORGANISM: Corynebacterium glutamicum
<220> FEATURE:
<221> NAME/KEY: CDS
<222> LOCATION: (1)..(204)

<400> SEQUENCE: 50 atg gca cag ggt act gtg aaa tgg ttc aac ggc gaa aag gga ttt ggt      48
Met Ala Gln Gly Thr Val Lys Trp Phe Asn Gly Glu Lys Gly Phe Gly
1               5                   10                  15 ttc atc gct ccc aac gat ggc tcc gca gat ctc ttc gtc cac tac tct      96
Phe Ile Ala Pro Asn Asp Gly Ser Ala Asp Leu Phe Val His Tyr Ser
            20                  25                  30 gag att cag ggc tcc ggt ttc cgt aat ctt gag gaa aac cag cca gtt     144
Glu Ile Gln Gly Ser Gly Phe Arg Asn Leu Glu Glu Asn Gln Pro Val
                35                  40                  45 gaa ttt gag gtc ggc gag ggc gcc aag ggc cca cag gct cag cag gtt     192
Glu Phe Glu Val Gly Glu Gly Ala Lys Gly Pro Gln Ala Gln Gln Val
        50                  55                  60 cgt gct ctc taa                                                      204
Arg Ala Leu
65

<210> SEQ ID NO 51
<211> LENGTH: 67
<212> TYPE: PRT
<213> ORGANISM: Corynebacterium glutamicum

<400> SEQUENCE: 51

Met Ala Gln Gly Thr Val Lys Trp Phe Asn Gly Glu Lys Gly Phe Gly
1               5                   10                  15

Phe Ile Ala Pro Asn Asp Gly Ser Ala Asp Leu Phe Val His Tyr Ser
            20                  25                  30

Glu Ile Gln Gly Ser Gly Phe Arg Asn Leu Glu Glu Asn Gln Pro Val
                35                  40                  45

Glu Phe Glu Val Gly Glu Gly Ala Lys Gly Pro Gln Ala Gln Gln Val
        50                  55                  60

Arg Ala Leu
65

```
<210> SEQ ID NO 52
<211> LENGTH: 384
<212> TYPE: DNA
<213> ORGANISM: Corynebacterium glutamicum
<220> FEATURE:
<221> NAME/KEY: CDS
<222> LOCATION: (1)..(384)

<400> SEQUENCE: 52 atg cct gtc gga aca gtg aag tgg tac gac gcg gag cgt ggt ttc ggc      48
Met Pro Val Gly Thr Val Lys Trp Tyr Asp Ala Glu Arg Gly Phe Gly
 1               5                  10                  15 ttt gtc tcc aat cca ggt ggt gaa gat tgc ttc gta ggt aag caa gta      96
Phe Val Ser Asn Pro Gly Gly Glu Asp Cys Phe Val Gly Lys Gln Val
             20                  25                  30 ctt ccc aag gga gtc acc gaa ttg cac aag gga cag cga atc gat ttt     144
Leu Pro Lys Gly Val Thr Glu Leu His Lys Gly Gln Arg Ile Asp Phe
         35                  40                  45 gac ttc gcc gca ggc cgt aag ggc cct caa gca ctt cga ata aag att     192
Asp Phe Ala Ala Gly Arg Lys Gly Pro Gln Ala Leu Arg Ile Lys Ile
     50                  55                  60 ctt gaa act cca cgc agg cgt cca cag cac aaa tac aag cca gaa gag     240
Leu Glu Thr Pro Arg Arg Arg Pro Gln His Lys Tyr Lys Pro Glu Glu
 65                  70                  75                  80 ctc aac gga atg atc tct gac ctc atc acg ctt cta gaa agt gga gtg     288
Leu Asn Gly Met Ile Ser Asp Leu Ile Thr Leu Leu Glu Ser Gly Val
                 85                  90                  95 caa cca ggc ctt gcc aaa ggg caa tac ccg gag cac aaa gct gga gcg     336
Gln Pro Gly Leu Ala Lys Gly Gln Tyr Pro Glu His Lys Ala Gly Ala
            100                 105                 110 cag gta gca gaa att ctt cgc gtt gtt gcg aag gag ctt gag tct taa     384
Gln Val Ala Glu Ile Leu Arg Val Val Ala Lys Glu Leu Glu Ser
        115                 120                 125

<210> SEQ ID NO 53
<211> LENGTH: 127
<212> TYPE: PRT
<213> ORGANISM: Corynebacterium glutamicum

<400> SEQUENCE: 53

Met Pro Val Gly Thr Val Lys Trp Tyr Asp Ala Glu Arg Gly Phe Gly
 1               5                  10                  15

Phe Val Ser Asn Pro Gly Gly Glu Asp Cys Phe Val Gly Lys Gln Val
             20                  25                  30

Leu Pro Lys Gly Val Thr Glu Leu His Lys Gly Gln Arg Ile Asp Phe
         35                  40                  45

Asp Phe Ala Ala Gly Arg Lys Gly Pro Gln Ala Leu Arg Ile Lys Ile
     50                  55                  60

Leu Glu Thr Pro Arg Arg Arg Pro Gln His Lys Tyr Lys Pro Glu Glu
 65                  70                  75                  80

Leu Asn Gly Met Ile Ser Asp Leu Ile Thr Leu Leu Glu Ser Gly Val
                 85                  90                  95

Gln Pro Gly Leu Ala Lys Gly Gln Tyr Pro Glu His Lys Ala Gly Ala
            100                 105                 110

Gln Val Ala Glu Ile Leu Arg Val Val Ala Lys Glu Leu Glu Ser
        115                 120                 125

<210> SEQ ID NO 54
<211> LENGTH: 249
<212> TYPE: DNA
<213> ORGANISM: Artificial sequence
```

<220> FEATURE:
<223> OTHER INFORMATION: somewhat like E. coli CspA

<400> SEQUENCE: 54

```
atggccggta aaatgactgg tatcgtaaaa tggttcaacg ctgacaaagg cttcggcttc      60
atcactcctg acgatggctc taaagatgtg ttcgtacact tctctgctat ccagaacgat     120
ggttacaaat ctctggacga aggtcagaaa gtgtccttca ccatcgaaag cggcgctaaa     180
ggcccggcag ctggtaacgt aaccagcctg aattcctcga gcgattacaa ggatgatgat     240
gataagtaa                                                             249
```

<210> SEQ ID NO 55
<211> LENGTH: 82
<212> TYPE: PRT
<213> ORGANISM: Artificial sequence
<220> FEATURE:
<223> OTHER INFORMATION: E. coli CspA-like

<400> SEQUENCE: 55

```
Met Ala Gly Lys Met Thr Gly Ile Val Lys Trp Phe Asn Ala Asp Lys
1               5                  10                  15

Gly Phe Gly Phe Ile Thr Pro Asp Asp Gly Ser Lys Asp Val Phe Val
            20                  25                  30

His Phe Ser Ala Ile Gln Asn Asp Gly Tyr Lys Ser Leu Asp Glu Gly
        35                  40                  45

Gln Lys Val Ser Phe Thr Ile Glu Ser Gly Ala Lys Gly Pro Ala Ala
    50                  55                  60

Gly Asn Val Thr Ser Leu Asn Ser Ser Asp Tyr Lys Asp Asp Asp
65                  70                  75                  80

Asp Lys
```

<210> SEQ ID NO 56
<211> LENGTH: 225
<212> TYPE: DNA
<213> ORGANISM: Artificial sequence
<220> FEATURE:
<223> OTHER INFORMATION: E. coli CspA-like

<400> SEQUENCE: 56

```
atggccggta aaatgactgg tatcgtaaaa tggttcaacg ctgacaaagg cttcggcttc      60
atcactcctg acgatggctc taaagatgtg ttcgtacact tctctgctat ccagaacgat     120
ggttacaaat ctctggacga aggtcagaaa gtgtccttca ccatcgaaag cggcgctaaa     180
ggcccggcag ctggtaacgt aaccagcctg aattcctcga cctag                    225
```

<210> SEQ ID NO 57
<211> LENGTH: 74
<212> TYPE: PRT
<213> ORGANISM: Artificial sequence
<220> FEATURE:
<223> OTHER INFORMATION: E. coli CspA-like protien

<400> SEQUENCE: 57

```
Met Ala Gly Lys Met Thr Gly Ile Val Lys Trp Phe Asn Ala Asp Lys
1               5                  10                  15

Gly Phe Gly Phe Ile Thr Pro Asp Asp Gly Ser Lys Asp Val Phe Val
            20                  25                  30

His Phe Ser Ala Ile Gln Asn Asp Gly Tyr Lys Ser Leu Asp Glu Gly
        35                  40                  45

Gln Lys Val Ser Phe Thr Ile Glu Ser Gly Ala Lys Gly Pro Ala Ala
```

```
                    50                  55                  60

Gly Asn Val Thr Ser Leu Asn Ser Ser Thr
 65                  70
```

<210> SEQ ID NO 58
<211> LENGTH: 240
<212> TYPE: DNA
<213> ORGANISM: Artificial sequence
<220> FEATURE:
<223> OTHER INFORMATION: B. subtilis CspB-like

<400> SEQUENCE: 58

```
atggtagaag gtaaagtaaa atggttcaac tctgaaaaag gtttcggatt catcgaagta      60
gaaggtcaag acgatgtatt cgttcatttc tctgctattc aaggcgaagg cttcaaaact     120
ttagaagaag gccaagctgt ttcttttgaa atcgttgaag aaaccgcgg accacaagct      180 gctaacgtta ctaaagaagc gaattcctcg agcgattaca aggatgatga tgataagtaa    240
```

<210> SEQ ID NO 59
<211> LENGTH: 79
<212> TYPE: PRT
<213> ORGANISM: Artificial sequence
<220> FEATURE:
<223> OTHER INFORMATION: B. subtilis CspB-like

<400> SEQUENCE: 59

```
Met Val Glu Gly Lys Val Lys Trp Phe Asn Ser Glu Lys Gly Phe Gly
  1               5                  10                  15

Phe Ile Glu Val Glu Gly Gln Asp Asp Val Phe Val His Phe Ser Ala
                 20                  25                  30

Ile Gln Gly Glu Gly Phe Lys Thr Leu Glu Glu Gly Gln Ala Val Ser
             35                  40                  45

Phe Glu Ile Val Glu Gly Asn Arg Gly Pro Gln Ala Ala Asn Val Thr
         50                  55                  60

Lys Glu Ala Asn Ser Ser Ser Asp Tyr Lys Asp Asp Asp Lys
 65                  70                  75
```

<210> SEQ ID NO 60
<211> LENGTH: 216
<212> TYPE: DNA
<213> ORGANISM: Artificial sequence
<220> FEATURE:
<223> OTHER INFORMATION: B. subtilis CspB-like

<400> SEQUENCE: 60

```
atggtagaag gtaaagtaaa atggttcaac tctgaaaaag gtttcggatt catcgaagta      60
gaaggtcaag acgatgtatt cgttcatttc tctgctattc aaggcgaagg cttcaaaact     120
ttagaagaag gccaagctgt ttcttttgaa atcgttgaag aaaccgcgg accacaagct      180 gctaacgtta ctaaagaagc gaattcctcg acctag                                216
```

<210> SEQ ID NO 61
<211> LENGTH: 71
<212> TYPE: PRT
<213> ORGANISM: Artificial sequence
<220> FEATURE:
<223> OTHER INFORMATION: B. subtilis CspB-like

<400> SEQUENCE: 61

```
Met Val Glu Gly Lys Val Lys Trp Phe Asn Ser Glu Lys Gly Phe Gly
  1               5                  10                  15

Phe Ile Glu Val Glu Gly Gln Asp Asp Val Phe Val His Phe Ser Ala
```

```
                    20                  25                  30
Ile Gln Gly Glu Gly Phe Lys Thr Leu Glu Glu Gly Gln Ala Val Ser
                35                  40                  45

Phe Glu Ile Val Glu Gly Asn Arg Gly Pro Gln Ala Ala Asn Val Thr
            50                  55                  60

Lys Glu Ala Asn Ser Ser Thr
65                  70

<210> SEQ ID NO 62
<211> LENGTH: 213
<212> TYPE: DNA
<213> ORGANISM: Artificial sequence
<220> FEATURE:
<223> OTHER INFORMATION: E. coli CspA-like

<400> SEQUENCE: 62
atggccggta aaatgactgg tatcgtaaaa tggttcaacg ctgacaaagg cttcggcttc      60
atcactcctg acgatggctc taaagatgtg ttcgtacact ctctgctat ccagaacgat     120 ggttacaaat ctctggacga aggtcagaaa gtgtccttca ccatcgaaag cggcgctaaa    180
ggcccggcag ctggtaacgt aaccagcctg tga                                 213

<210> SEQ ID NO 63
<211> LENGTH: 70
<212> TYPE: PRT
<213> ORGANISM: Artificial sequence
<220> FEATURE:
<223> OTHER INFORMATION: CspA-like protein

<400> SEQUENCE: 63

Met Ala Gly Lys Met Thr Gly Ile Val Lys Trp Phe Asn Ala Asp Lys
1               5                   10                  15

Gly Phe Gly Phe Ile Thr Pro Asp Asp Gly Ser Lys Asp Val Phe Val
                20                  25                  30

His Phe Ser Ala Ile Gln Asn Asp Gly Tyr Lys Ser Leu Asp Glu Gly
            35                  40                  45

Gln Lys Val Ser Phe Thr Ile Glu Ser Gly Ala Lys Gly Pro Ala Ala
        50                  55                  60

Gly Asn Val Thr Ser Leu
65                  70

<210> SEQ ID NO 64
<211> LENGTH: 204
<212> TYPE: DNA
<213> ORGANISM: Artificial sequence
<220> FEATURE:
<223> OTHER INFORMATION: B. subtilis CspB-like

<400> SEQUENCE: 64
atggtagaag gtaaagtaaa atggttcaac tctgaaaaag gtttcggatt catcgaagta     60
gaaggtcaag acgatgtatt cgttcatttc tctgctattc aaggcgaagg cttcaaaact   120
ttagaagaag gccaagctgt ttctttttgaa atcgttgaag aaaccgcgg accacaagct   180 gctaacgtta ctaaagaagc gtga                                           204

<210> SEQ ID NO 65
<211> LENGTH: 67
<212> TYPE: PRT
<213> ORGANISM: Artificial sequence
<220> FEATURE:
<223> OTHER INFORMATION: B. subtilis CspB-like
```

-continued

```
<400> SEQUENCE: 65

Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
            20                  25                  30

Ile Gln Gly Glu Gly Phe Lys Thr Leu Glu Glu Gly Gln Ala Val Ser
        35                  40                  45

Phe Glu Ile Val Glu Gly Asn Arg Gly Pro Gln Ala Ala Asn Val Thr
    50                  55                  60

Lys Glu Ala
65

<210> SEQ ID NO 66
<211> LENGTH: 23
<212> TYPE: DNA
<213> ORGANISM: Artificial sequence
<220> FEATURE:
<223> OTHER INFORMATION: Primer for PCR

<400> SEQUENCE: 66
aggtaataca ccatggccgg taa                                          23

<210> SEQ ID NO 67
<211> LENGTH: 24
<212> TYPE: DNA
<213> ORGANISM: Artificial sequence
<220> FEATURE:
<223> OTHER INFORMATION: Primer for PCR

<400> SEQUENCE: 67
ttaagcagag aattcaggct ggtt                                         24

<210> SEQ ID NO 68
<211> LENGTH: 7
<212> TYPE: PRT
<213> ORGANISM: Artificial sequence
<220> FEATURE:
<223> OTHER INFORMATION: Flag tag for epitope tagging

<400> SEQUENCE: 68

Asp Tyr Lys Asp Asp Asp Lys
1               5

<210> SEQ ID NO 69
<211> LENGTH: 23
<212> TYPE: DNA
<213> ORGANISM: Artificial sequence
<220> FEATURE:
<223> OTHER INFORMATION: PCR primer

<400> SEQUENCE: 69
aggaggaaat tccatggtag aag                                          23

<210> SEQ ID NO 70
<211> LENGTH: 26
<212> TYPE: DNA
<213> ORGANISM: Artificial sequence
<220> FEATURE:
<223> OTHER INFORMATION: PCR primer

<400> SEQUENCE: 70
tcaatttatg aattcgcttc tttagt                                       26

<210> SEQ ID NO 71
```

```
<211> LENGTH: 27
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (27)..(27)
<223> OTHER INFORMATION: n=a,c,t, or g

<400> SEQUENCE: 71
gggcactttg tacaagaaag ctgggtn                                      27

<210> SEQ ID NO 72
<211> LENGTH: 28
<212> TYPE: DNA
<213> ORGANISM: Artificial sequence
<220> FEATURE:
<223> OTHER INFORMATION: PCR primer
<220> FEATURE:
<221> NAME/KEY: misc_feature
<222> LOCATION: (28)..(28)
<223> OTHER INFORMATION: n=a,c,t, or g

<400> SEQUENCE: 72
ggggcacttt gtacaagaaa gctgggtn                                     28

<210> SEQ ID NO 73
<211> LENGTH: 14
<212> TYPE: DNA
<213> ORGANISM: Artificial sequence
<220> FEATURE:
<223> OTHER INFORMATION: PCR primer

<400> SEQUENCE: 73
cctgcaggac catg                                                    14

<210> SEQ ID NO 74
<211> LENGTH: 17
<212> TYPE: DNA
<213> ORGANISM: Artificial sequence
<220> FEATURE:
<223> OTHER INFORMATION: PCR primer

<400> SEQUENCE: 74
cctgcaggct cgagcta                                                 17

<210> SEQ ID NO 75
<211> LENGTH: 43
<212> TYPE: DNA
<213> ORGANISM: Artificial sequence
<220> FEATURE:
<223> OTHER INFORMATION: PCR primer

<400> SEQUENCE: 75
ggggacaagt ttgtacaaaa aagcaggctc ctgcaggacc atg                    43

<210> SEQ ID NO 76
<211> LENGTH: 47
<212> TYPE: DNA
<213> ORGANISM: Artificial sequence
<220> FEATURE:
<223> OTHER INFORMATION: PCR primer

<400> SEQUENCE: 76
ggggaccact ttgtacaaga aagctgggtc cctgcaggct cgagcta                47

<210> SEQ ID NO 77
```

```
<211> LENGTH: 18
<212> TYPE: DNA
<213> ORGANISM: Artificial sequence
<220> FEATURE:
<223> OTHER INFORMATION: PCR primer

<400> SEQUENCE: 77
ccccaccctg caatgtga                                                   18

<210> SEQ ID NO 78
<211> LENGTH: 31
<212> TYPE: DNA
<213> ORGANISM: Artificial sequence
<220> FEATURE:
<223> OTHER INFORMATION: PCR primer

<400> SEQUENCE: 78
tgtgcatcct tttatttcat acattaatta a                                    31

<210> SEQ ID NO 79
<211> LENGTH: 30
<212> TYPE: DNA
<213> ORGANISM: Artificial sequence
<220> FEATURE:
<223> OTHER INFORMATION: PCR primer

<400> SEQUENCE: 79
cctagacttg tccatcttct ggattggcca                                      30

<210> SEQ ID NO 80
<211> LENGTH: 16
<212> TYPE: DNA
<213> ORGANISM: Artificial sequence
<220> FEATURE:
<223> OTHER INFORMATION: PCR primer

<400> SEQUENCE: 80
gcctgccgca gaccaa                                                     16

<210> SEQ ID NO 81
<211> LENGTH: 20
<212> TYPE: DNA
<213> ORGANISM: Artificial sequence
<220> FEATURE:
<223> OTHER INFORMATION: PCR primer

<400> SEQUENCE: 81
atgcagagct cagcttcatc                                                 20

<210> SEQ ID NO 82
<211> LENGTH: 24
<212> TYPE: DNA
<213> ORGANISM: Artificial sequence
<220> FEATURE:
<223> OTHER INFORMATION: PCR primer

<400> SEQUENCE: 82
tccagtacgt gcagtccctc ctcc                                            24

<210> SEQ ID NO 83
<211> LENGTH: 24
<212> TYPE: DNA
<213> ORGANISM: Artificial sequence
<220> FEATURE:
<223> OTHER INFORMATION: PCR primer

<400> SEQUENCE: 83
```

```
cgtctacaat cagaaggcgt aatc                                            24
```

<210> SEQ ID NO 84
<211> LENGTH: 23
<212> TYPE: DNA
<213> ORGANISM: Artificial sequence
<220> FEATURE:
<223> OTHER INFORMATION: PCR primer

<400> SEQUENCE: 84

```
ccaacaggtg aatgcttgat agg                                             23
```

<210> SEQ ID NO 85
<211> LENGTH: 18
<212> TYPE: DNA
<213> ORGANISM: Artificial sequence
<220> FEATURE:
<223> OTHER INFORMATION: PCR primer

<400> SEQUENCE: 85

```
catgcgccgc tttgcttc                                                   18
```

<210> SEQ ID NO 86
<211> LENGTH: 52
<212> TYPE: DNA
<213> ORGANISM: Artificial sequence
<220> FEATURE:
<223> OTHER INFORMATION: PCR primer

<400> SEQUENCE: 86

```
gcgcaggcct agatgtacca tgtccggtaa aatgactggt atcgtaaaat gg             52
```

<210> SEQ ID NO 87
<211> LENGTH: 46
<212> TYPE: DNA
<213> ORGANISM: Artificial sequence
<220> FEATURE:
<223> OTHER INFORMATION: PCR primer

<400> SEQUENCE: 87

```
cgcgaattcg gatccttatt acaggctggt tacgttacca gctgcc                    46
```

<210> SEQ ID NO 88
<211> LENGTH: 53
<212> TYPE: DNA
<213> ORGANISM: Artificial sequence
<220> FEATURE:
<223> OTHER INFORMATION: PCR primer

<400> SEQUENCE: 88

```
gcgcaggcct agatgtacca tgttagaagg taaagtaaaa tggttcaact ctg            53
```

<210> SEQ ID NO 89
<211> LENGTH: 51
<212> TYPE: DNA
<213> ORGANISM: Artificial sequence
<220> FEATURE:
<223> OTHER INFORMATION: PCR primer

<400> SEQUENCE: 89

```
cgcgaattcg gatccttatt acgcttcttt agtaacgtta gcagcttgtg g              51
```

<210> SEQ ID NO 90
<211> LENGTH: 204
<212> TYPE: DNA
<213> ORGANISM: Artificial sequence
<220> FEATURE:

<223> OTHER INFORMATION: Synthetic codons optimizing CspB for plant
      expression
<220> FEATURE:
<221> NAME/KEY: CDS
<222> LOCATION: (1)..(204)

<400> SEQUENCE: 90

```
atg gtg gag ggc aag gtg aag tgg ttc aac tcc gag aag ggc ttc ggc        48
Met Val Glu Gly Lys Val Lys Trp Phe Asn Ser Glu Lys Gly Phe Gly
1               5                   10                  15 ttc atc gag gtg gag ggt caa gac gat gtg ttc gtc cac ttc tcc gcc        96
Phe Ile Glu Val Glu Gly Gln Asp Asp Val Phe Val His Phe Ser Ala
                20                  25                  30 atc cag ggc gaa ggg ttc aag acc ctg gaa gag ggg cag gcc gtc tcc       144
Ile Gln Gly Glu Gly Phe Lys Thr Leu Glu Glu Gly Gln Ala Val Ser
            35                  40                  45 ttc gag atc gtc gag gga aac cgc ggt ccg cag gcc gcg aac gtc acg       192
Phe Glu Ile Val Glu Gly Asn Arg Gly Pro Gln Ala Ala Asn Val Thr
        50                  55                  60 aag gaa gcg tga                                                       204
Lys Glu Ala
65
```

<210> SEQ ID NO 91
<211> LENGTH: 67
<212> TYPE: PRT
<213> ORGANISM: Artificial sequence
<220> FEATURE:
<223> OTHER INFORMATION: Synthetic Construct

<400> SEQUENCE: 91

```
Met Val Glu Gly Lys Val Lys Trp Phe Asn Ser Glu Lys Gly Phe Gly
1               5                   10                  15

Phe Ile Glu Val Glu Gly Gln Asp Asp Val Phe Val His Phe Ser Ala
                20                  25                  30

Ile Gln Gly Glu Gly Phe Lys Thr Leu Glu Glu Gly Gln Ala Val Ser
            35                  40                  45

Phe Glu Ile Val Glu Gly Asn Arg Gly Pro Gln Ala Ala Asn Val Thr
        50                  55                  60

Lys Glu Ala
65
```

<210> SEQ ID NO 92
<211> LENGTH: 213
<212> TYPE: DNA
<213> ORGANISM: Artificial sequence
<220> FEATURE:
<223> OTHER INFORMATION: Synthetic codons encoding CspA
<220> FEATURE:
<221> NAME/KEY: CDS
<222> LOCATION: (1)..(213)

<400> SEQUENCE: 92

```
atg gcc ggc aag atg acc ggc atc gtg aag tgg ttc aac gct gac aag        48
Met Ala Gly Lys Met Thr Gly Ile Val Lys Trp Phe Asn Ala Asp Lys
1               5                   10                  15 ggc ttc ggc ttc atc acg ccg gac gac ggc agc aag gat gtc ttc gtg        96
Gly Phe Gly Phe Ile Thr Pro Asp Asp Gly Ser Lys Asp Val Phe Val
                20                  25                  30 cac ttc tcc gcc atc cag aac gac ggc tac aag tcc ctc gac gag ggc       144
His Phe Ser Ala Ile Gln Asn Asp Gly Tyr Lys Ser Leu Asp Glu Gly
            35                  40                  45 cag aag gtc agc ttc acc atc gag agc ggc gcc aaa ggc ccg gcc gcc       192
Gln Lys Val Ser Phe Thr Ile Glu Ser Gly Ala Lys Gly Pro Ala Ala
```

```
                    50                  55                  60
ggt aac gtc acg tcg ctg tga                                              213
Gly Asn Val Thr Ser Leu
 65                  70

<210> SEQ ID NO 93
<211> LENGTH: 70
<212> TYPE: PRT
<213> ORGANISM: Artificial sequence
<220> FEATURE:
<223> OTHER INFORMATION: Synthetic Construct

<400> SEQUENCE: 93

Met Ala Gly Lys Met Thr Gly Ile Val Lys Trp Phe Asn Ala Asp Lys
 1               5                  10                  15

Gly Phe Gly Phe Ile Thr Pro Asp Asp Gly Ser Lys Asp Val Phe Val
                20                  25                  30

His Phe Ser Ala Ile Gln Asn Asp Gly Tyr Lys Ser Leu Asp Glu Gly
            35                  40                  45

Gln Lys Val Ser Phe Thr Ile Glu Ser Gly Ala Lys Gly Pro Ala Ala
        50                  55                  60

Gly Asn Val Thr Ser Leu
 65                  70

<210> SEQ ID NO 94
<211> LENGTH: 201
<212> TYPE: DNA
<213> ORGANISM: Bacillus thuringiensis
<220> FEATURE:
<221> NAME/KEY: CDS
<222> LOCATION: (1)..(201)

<400> SEQUENCE: 94 atg caa aca ggt aaa gtt aaa tgg ttc aac agc gaa aaa ggt ttc ggt        48
Met Gln Thr Gly Lys Val Lys Trp Phe Asn Ser Glu Lys Gly Phe Gly
 1               5                  10                  15 ttc atc gaa gtt gaa ggt gga gac gat gta ttc gtt cac ttc tca gct        96
Phe Ile Glu Val Glu Gly Gly Asp Asp Val Phe Val His Phe Ser Ala
                20                  25                  30 atc caa ggt gac gga ttc aaa act tta gaa gaa ggt caa gaa gtt tct       144
Ile Gln Gly Asp Gly Phe Lys Thr Leu Glu Glu Gly Gln Glu Val Ser
            35                  40                  45 ttc gaa atc gtt gaa ggt aac cgt gga cca caa gct gct aac gtt aca       192
Phe Glu Ile Val Glu Gly Asn Arg Gly Pro Gln Ala Ala Asn Val Thr
        50                  55                  60 aaa aac taa                                                            201
Lys Asn
 65

<210> SEQ ID NO 95
<211> LENGTH: 66
<212> TYPE: PRT
<213> ORGANISM: Bacillus thuringiensis

<400> SEQUENCE: 95

Met Gln Thr Gly Lys Val Lys Trp Phe Asn Ser Glu Lys Gly Phe Gly
 1               5                  10                  15
```

-continued

```
Phe Ile Glu Val Glu Gly Gly Asp Asp Val Phe Val His Phe Ser Ala
            20              25              30

Ile Gln Gly Asp Gly Phe Lys Thr Leu Glu Glu Gly Gln Glu Val Ser
        35              40              45

Phe Glu Ile Val Glu Gly Asn Arg Gly Pro Gln Ala Ala Asn Val Thr
    50              55              60

Lys Asn
65
```